(12) United States Patent
Sundermann et al.

(10) Patent No.: US 7,560,468 B2
(45) Date of Patent: Jul. 14, 2009

(54) SUBSTITUTED 1,4,8-TRIAZASPIRO[4,5]DECAN-2-ONE COMPOUNDS

(75) Inventors: Corinna Sundermann, Aachen (DE); Bernd Sundermann, Aachen (DE); Stefan Ober-Boersch, Aachen (DE); Werner Englberger, Stolberg (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 119 days.

(21) Appl. No.: 11/525,052

(22) Filed: Sep. 22, 2006

(65) Prior Publication Data
US 2007/0015783 A1     Jan. 18, 2007

Related U.S. Application Data

(63) Continuation of application No. PCT/EP2005/003051, filed on Mar. 22, 2005.

(30) Foreign Application Priority Data
Mar. 22, 2004 (DE) .................. 10 2004 014 304

(51) Int. Cl.
*A61K 31/438* (2006.01)
*C07D 471/10* (2006.01)
(52) U.S. Cl. ........................... 514/278; 546/20
(58) Field of Classification Search ................ 514/278; 546/20
See application file for complete search history.

(56) References Cited

U.S. PATENT DOCUMENTS 3,725,389 A     4/1973     McCaully et al.

FOREIGN PATENT DOCUMENTS

| EP | 1 420 020 A1 | 5/2004 |
|---|---|---|
| JP | 01207291 A | 8/1989 |
| WO | WO 94/10171 A1 | 5/1994 |
| WO | WO 94/21619 A1 | 9/1994 |

OTHER PUBLICATIONS

Tzschentke, Thomas M., "NA and 5-HT Reuptake Inhibitors and α2 agonists", Analgesics: From Chemistry and Pharmacology to Clinical Application, pp. 265-284, Wiley 2002.
Berard, RMF, "The Appropriate Use of Antidepressants in the Cancer Setting: A Review", IMJ, Dec. 1996, pp. 257-259, vol. 3, No. 4.
Baker, David et al., "Cannabinoids control spasticity and tremor in a multiple sclerosis model", Nature, Mar. 2, 2000, pp. 84-87, vol. 404, Macmillian Magazines Ltd.
Sánchez, Cristina et al., "Inhibition of Glioma Growth in Vivo by Selective Activation of the $CB_2$ Cannabinoid Receptor", Antitumoral Action of Cannabinoids, Aug. 1, 2001, pp. 5784-5789, vol. 61 Cancer Research.
Malan Jr., T. P. et al., "$CB_2$ cannabinoid receptor-mediated peripheral antinociception", Pain, 2001, pp. 239-245, vol. 93, Elsevier Science B.V.
Recht, Lawrence D. et al., "Antitumor effects of ajulemic acid (CT3), a synthetic non-psychoactive cannabinoid", Biochemical Pharmacology, 2001, pp. 755-763, vol. 62, Elsevier Science Inc.
Gennaro, A. R., "Reminton's Pharmaceutical Sciences", particularly in Section 8, Chapter from 76 to 93, 17th Edition, 1985, Mack Publishing Company, Easton, Pa.
Gray, E. G. et al., "The Isolation of Nerve Endings From Brain: An Electron-Microscopic Study Of Cell Fragments Derived By Homogenization And Centrifugation", 1962, pp. 79-88, Anatomy, vol. 96.
Lowry, Oliver H. et al., "Protein Measurement With The Folin Phenol Reagent", J. Biol. Chem., May 28, 1951, pp. 265-275.
Frink, Martin CH. et al., "Influence of Tramadol on Neurotransmitter Systems of the Rat Brain", Arzneim.-Forsch/Drug Res., 1996, pp. 1029-1036, vol. 11.
Cheng, Yung-Chi et al., "Relationship Between The Inhibition Constant ($K_1$) And The Concentration Of Inhibitor Which Causes 50 Per Cent Inhibition ($I_{50}$) Of An Enzymatic Reaction", Biochemical Pharmacology, 1973, pp. 3099-3108, vol. 22, Pergamon Press.

*Primary Examiner*—Charanjit S Aulakh
(74) *Attorney, Agent, or Firm*—Crowell & Moring LLP

(57) ABSTRACT

Novel 1,4,8-triazaspiro[4,5]decan-2-one compounds corresponding to formula I

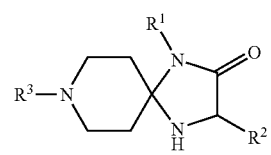

processes for the preparation thereof, related methods of treatment and pharmaceutical formulations containing such compounds.

19 Claims, No Drawings

SUBSTITUTED 1,4,8-TRIAZASPIRO[4,5]DECAN-2-ONE COMPOUNDS

CROSS-REFERENCE TO RELATED APPLICATIONS

This application is a continuation of International patent application Ser. No. PCT/EP2005/003051 filed Mar. 22, 2005 which claims benefit to German patent application Serial No. 10 2004 014 304.8 filed Mar. 22, 2004, the entire disclosures of which are hereby incorporated in their entirety.

FIELD OF THE INVENTION

The present invention relates to substituted 1,4,8-triazaspiro[4,5]decan-2-one compounds, to a process for the preparation thereof, to a medicinal drug containing this compound and to the use of these compounds for the production of medicinal drugs.

BACKGROUND OF THE INVENTION

Depression is an affectivity disorder in which a depressive syndrome is conspicuous, "depressive" being understood to refer to a state of dejection or melancholia. The antidepressants used for therapy are also important adjuvants for pain therapy (as is described in the publication by Tzschentke, Na and 5-hT Reuptake inhibitor and $\alpha_2$ agonists, in Analgesics: From Chemistry and Pharmacology to Clinical Application, Page 265-284, Wiley 2002), particularly in the case of chronic states of pain, since the continuous pain stress can cause a depressive mod in the patients. This is very frequently the case with cancer patients suffering pain (Berard, INT. MED—J. 1996, 3/4, 257-259). Treatment of depression is therefore highly significant in the field of medicine and there is a world-wide need for effective antidepressant therapies. The basis for such an antidepressant action in a pharmacological active substance is its capability to inhibit the reuptake of serotonin.

SUMMARY OF THE INVENTION

It is thus an object of the present invention to provide compounds which are particularly suitable for use as pharmaceutically active substances in medicinal drugs, preferably in medicinal drugs for prophylaxis and/or treatment of depression.

It has now been found, surprisingly, that substituted 1,4,8-triazaspiro[4,5]decan-2-one compounds of the general formula I given below are suitable for regulation, preferably inhibition, of reuptake of serotonin (5-hydroxytryptophane). Furthermore, it has been found that the compounds of the invention are also suitable for regulation, preferably inhibition, of noradrenalin reuptake and also exhibit a high affinity to batrachotoxin (BTX) receptors and/or cannabinoid receptors CB2 (CB2 receptors) and are therefore particularly suitable for use as pharmaceutically active substances in medicinal drugs for the inhibition and/or treatment of disorders associated with these receptors or processes. For purposes of this disclosure, inhibit and the forms thereof mean to lessen or limit. In certain embodiments the compounds may also be useful in the prophylaxis of certain disorders or conditions.

An object of the present invention is thus the provision of substituted 1,4,8-triazaspiro[4,5]decan-2-one compounds of the general formula I,

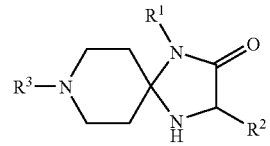

in which
R$^1$ stands for a hydrogen radical, or for a linear or branched unsubstituted or at least monosubstituted alkyl radical optionally comprising at least one heteroatom as a link, or for a linear or branched unsubstituted or at least monosubstituted alkenyl radical optionally comprising at least one heteroatom as a link, or for a linear or branched unsubstituted or at least monosubstituted alkynyl radical optionally comprising at least one heteroatom as a link, or for an unsubstituted or at least monosubstituted aryl radical or an unsubstituted or at least monosubstituted heteroaryl radical, which aryl and heteroaryl radicals are can be bonded via a linear or branched alkylene group optionally comprising at least one heteroatom as a link, or for a —C(=O)OR$^7$ radical can be bonded via a linear or branched alkylene group, R$^2$ stands for a hydrogen radical, or for a linear or branched unsubstituted or at least monosubstituted alkyl radical optionally comprising at least one heteroatom as a link, or for a linear or branched unsubstituted or at least monosubstituted alkenyl radical optionally comprising at least one heteroatom as a link, or for a linear or branched unsubstituted or at least monosubstituted alkynyl radical optionally comprising at least one heteroatom as a link, or for an unsubstituted or at least monosubstituted aryl radical or an unsubstituted or at least monosubstituted heteroaryl radical, which aryl and heteroaryl radicals can be bonded via a linear or branched alkylene group optionally comprising at least one heteroatom as a link, R$^3$ stands or for a —S(=O)$_2$—R$^4$ group, or for a —C(=S)NH—R$^5$ group or for a —C(=O)NH—R$^6$ group, R$^4$ stands for an —NR$^{10}$R$^{11}$ radical, or for a linear or branched unsubstituted or at least monosubstituted alkyl radical optionally comprising at least one heteroatom as a link, or for a linear or branched unsubstituted or at least monosubstituted alkenyl radical optionally comprising at least one heteroatom as a link, or for a linear or branched unsubstituted or at least monosubstituted alkynyl radical optionally comprising at least one heteroatom as a link, or for an unsubstituted or at least monosubstituted aryl radical or an unsubstituted or at least monosubstituted heteroaryl radical, which latter radicals can be bonded via a linear or branched unsubstituted or at least monosubstituted alkylene group optionally comprising at least one heteroatom as a link and/or condensed with an unsubstituted or at least monosubstituted monocyclic ring system, or for an unsubstituted or at least monosubstituted cycloaliphatic radical, which optionally comprises at least one heteroatom as a ring member and which can be bonded via a linear or branched unsubstituted or at least monosubstituted alkylene group optionally comprising at least one heteroatom as a link and/or bridged by a linear or branched unsubstituted or at least monosubstituted alkylene group, R$^5$ stands for a linear or branched unsubstituted or at least monosubstituted alkyl radical optionally comprising at least one heteroatom as a link, or for a linear or branched unsubstituted or at least monosubstituted alkenyl radical optionally comprising at least one heteroatom as a link, or for a linear or branched unsubstituted or at least monosubstituted alkynyl radical optionally comprising at least one heteroatom as a link, or for an unsubstituted or at least monosubstituted aryl radical or an unsubstituted or at least monosubstituted heteroaryl radical, which radical can be bonded via a linear or branched unsubstituted or at least monosubstituted alkylene group optionally comprising at least one heteroatom as a link, or for an unsubstituted or at least monosubstituted cycloaliphatic radical, which optionally comprises at least one heteroatom as a ring member or which can be bonded via a linear or branched unsubstituted or at least monosubstituted alkylene group optionally comprising at least one heteroatom as a link, or for a —C(=O)OR$^8$ radical or for a —C(=O)OR$^9$ radical can be bonded via a linear or branched alkylene group, R$^6$ stands for an unsubstituted or at least monosubstituted aryl radical or an unsubstituted or at least monosubstituted heteroaryl radical, which aryl and heteroaryl radicals can be bonded via a linear or branched unsubstituted or at least monosubstituted alkylene group optionally comprising at least one heteroatom as a link, or for an unsubstituted or at least monosubstituted cycloaliphatic radical, which optionally comprises at least one heteroatom as a ring member or which can be bonded via a linear or branched unsubstituted or at least monosubstituted alkylene group optionally comprising at least one heteroatom as a link, R$^7$, R$^8$, R$^9$, R$^{10}$, and R$^{11}$, each independently stand for a linear or branched alkyl radical, a linear or branched alkenyl radical, or a linear or branched alkynyl radical, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

If one of the radicals R$^1$ to R$^{18}$ stands for an alkyl radical, an alkenyl radical or an alkynyl radical or comprises such a radical, this radical can—unless otherwise stated—be unsubstituted or monosubstituted or polysubstituted, preferably by 1, 2, 3, 4, or 5 substituents, and the substituents can be preferably independently selected from the group consisting of F, Cl, Br, C$_{1-6}$ alkoxy, hydroxy, SH, CN, CF$_3$, CHF$_2$, CH$_2$F, —NO$_2$, unsubstituted phenyl and —NR$^a$R$^b$, in which R$^a$ and R$^b$ can be independently selected from the group consisting of H, methyl, ethyl, n-propyl, isopropyl, and unsubstituted phenyl.

Alkenyl radicals exhibit at least one carbon-carbon double—and alkynyl radicals at least one carbon-carbon triple bond.

Suitable alkyl, alkenyl, and alkynyl radicals, which can be monosubstituted or polysubstituted, preferably substituted by 1, 2, 3, 4, or 5 substituents, can, for example, be selected from the group consisting of methyl, ethyl, n-propyl, isopropyl, n-butyl, isobutyl, sec-butyl, tert-butyl, n-pentyl, isopentyl, neopentyl, 2-pentyl, 3-pentyl, —(CH$_2$)C(CH$_3$)$_3$, 2,2-dimethylpropyl, penta-1,3-dienyl, n-hexyl, 2-hexyl, 3-hexyl, —(CH$_2$)(CH$_2$)C(CH$_3$)$_3$, n-heptyl, 3-heptyl, 4-heptyl, n-octyl, —(CH$_2$)(CH)(C$_2$H$_5$)(CH$_2$)(CH$_2$)(CH$_2$)(CH$_3$), n-nonyl, n-decyl, vinyl, ethynyl, propenyl, 1-propenyl, 2-propenyl, allyl, propynyl, 1-propynyl, 2-propynyl, butenyl, 1-butenyl, 2-butenyl, 3-butenyl, butynyl, 1-butynyl, 2-butynyl, 3-butynyl, pentenyl, pentynyl, hexenyl, and hexynyl.

The alkyl, alkenyl, and alkynyl radicals used in the present invention can—unless otherwise stated—also comprise one or more heteroatoms, preferably one or more oxygen atoms and/or one or more sulfur atoms, more preferably 1 or 2 oxygen atoms and/or sulfur atoms, as a link(s). Preferably, these heteroatoms are located in a non-terminal position of the respective radical. Mention may be made, for example, of radicals such as —CH$_2$—CH$_2$—S—CH$_3$ or —CH$_2$—CH$_2$—O—CH$_3$.

If one of the radicals R$^1$ to R$^{18}$ stands for a cycloaliphatic radical or comprises a cycloaliphatic radical, this radical can—unless otherwise stated—be unsubstituted or monosubstituted or polysubstituted, preferably by 1, 2, 3, 4, or 5 substituents, while the substituents can be preferably independently selected from the group consisting of F, Cl, Br, C$_{1-6}$ alkoxy, C$_{1-6}$ alkyl, hydroxy, CN, CF$_3$, CHF$_2$, CH$_2$F, unsubstituted phenyl, —NR$^a$R$^b$, in which R$^a$ and R$^b$ can be independently selected from the group consisting of H, methyl, ethyl, n-propyl, isopropyl, and unsubstituted phenyl, oxo (=O), thioxo (=S), I, —SF$_5$, —NO$_2$, —O—CF$_3$, —S—CF$_3$, —SH, —S—C$_{1-5}$ alkyl, —C(=O)H, —C(=O)C$_{1-5}$ alkyl, —C(=O)C$_{1-5}$ perflouroalkyl, —C(=O)OH, —C(=O)O—C$_{1-5}$ alkyl, —(CH$_2$)C(=O)OH, —(CH$_2$)C(=O)O—C$_{1-5}$ alkyl, —(CH$_2$)benzo[b]furanyl, —O-phenyl, —O-benzyl, phenyl, benzyl, naphthyl, and —(CH$_2$) naphthyl, while in each case the cyclic moiety of the radicals —O-phenyl, —O-benzyl, phenyl, —(CH$_2$)benzo[b]furanyl, benzyl, naphthyl, and —(CH$_2$) naphthyl can be substituted by 1, 2, 3, 4, or 5 substituents independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl, and —O-benzyl.

For the purposes of the present invention cycloaliphatic radicals are taken to mean both saturated and unsaturated radicals. The cycloaliphatic radicals can optionally comprise one or more heteroatoms, preferably 1, 2, 3, 4, or 5 heteroatom(s), preferably independently selected from the group consisting of nitrogen, oxygen, and sulfur, as ring members.

Suitable cycloaliphatic radicals, which can be monosubstituted or polysubstituted, can, for example, be selected from the group consisting of cyclopropyl, cyclobutyl, cyclopentyl, cyclohexyl, cycloheptyl, cycloctyl, cyclopentenyl, cyclohexenyl, cycloheptenyl, cyclooctenyl, tetrahydrofuryl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, and dithiolanyl.

Furthermore, the cycloaliphatic radicals can be at least singly bridged by a linear or branched alkylene group, preferably by one or two linear or branched C$_{1-5}$ alkylene groups. The 4,7,7-dimethyl-2-oxobicyclo[2.2.1]heptyl radical or the adamantyl radical may be mentioned as an example of such a cycloaliphatic radical.

If one of the radicals R$^1$ to R$^{18}$ stands for an aryl radical or heteroaryl radical or comprises an aryl radical or heteroaryl radical, this aryl radical or heteroaryl radical can—unless otherwise stated—be monosubstituted or polysubstituted, preferably by 1, 2, 3, 4, or 5 substituents, while the substituents can be independently preferably selected from the group consisting of F, Cl, Br, CN, NO$_2$, C$_{1-5}$ alkyl, C$_{1-5}$ alkoxy, —S—C$_{1-5}$ alkyl, OH, phenoxy, CHO, —C(=O)C$_{1-5}$ alkyl, —C(=S)C$_{1-5}$ alkyl, —COOH, —C(=O)NH$_2$, —C(=O)NH—C$_{1-5}$ alkyl, —C(=O)N(C$_{1-5}$ alkyl)$_2$, —C(=O)O—C$_{1-5}$ alkyl, —S(=O)C$_{1-6}$ alkyl, —S(=O)$_2$—C$_{1-6}$ alkyl, —S(=O)₂—NH₂, —C(=O)C$_{1-5}$ perfluoroalkyl, —CF₃, —CHF₂, —CH₂F, and —NR$^a$R$^b$, in which R$^a$ and R$^b$ can be independently selected from the group consisting of H, methyl, ethyl, n-propyl, isopropyl, and unsubstituted phenyl, I, —CF₃, —SF₅, —O—C$_{2-5}$ alkenyl, —O—CF₃, —O—CHF₂, —O—CH₂F, —S—CF₃, —S—CHF₂, —S—CH₂F, —SH, —C$_{1-5}$ alkyl, —O—C(=O)C$_{1-5}$ alkyl, —O—C(=O)phenyl, —(CH₂)O—C(=O)C$_{1-5}$ alkyl, —(CH₂)O—C(=O)phenyl, —NH—C(=O)O—C$_{1-5}$ alkyl, —NH—C(=O)C$_{1-5}$ alkyl, —C(=O)C$_{1-5}$ perflouroalkyl, —S(=O)₂—NH₂, —S(=O)₂—NH—C$_{1-5}$ alkyl, —S(=O)₂—NH-phenyl, —S(=O)₂—C$_{1-5}$ alkyl, —(CH₂)benzo[b]furanyl, —O-phenyl, —S-phenyl, —S-benzyl, —O-benzyl, phenyl, and benzyl, wherein each of the cyclic moieties of the radicals —O—C(=O)phenyl, —(CH₂)O—C(=O)phenyl, —S(=O)₂—NH-phenyl, phenoxy, phenyl, —S-phenyl, —S-benzyl, —O-benzyl, phenyl, —(CH₂)benzo[b]furanyl, and benzyl can be substituted by 1, 2, 3, 4, or 5 substituents independently selected from the group consisting of F, Cl, Br, —OH, —CF₃, —SF₅, —CN, —NO₂, —O—C$_{1-5}$ alkyl, —C$_{1-5}$ alkyl, —O—CF₃, —S—CF₃, phenyl, and —O-benzyl.

The heteroatoms of the heteroaryl radical can be selected preferably from the group consisting of oxygen, nitrogen, and sulfur. Preferably, each of the heteroaryl radicals comprises 1, 2, 3, 4, or 5 heteroatom(s) as a ring member(s), which are independently selected from the group consisting of oxygen, nitrogen, and sulfur.

Suitable aryl radicals can be selected preferably from the group consisting of phenyl, 1-naphthyl, and 2-naphthyl.

Suitable heteroaryl radicals can be preferably selected from the group consisting of pyrrolyl, indolyl, furyl (furanyl), benzofuranyl, thienyl (thiophenyl), benzothienyl, pyrazolyl, imidazolyl, thiazolyl, oxazolyl, isoxazolyl, pyridynyl, pyridazynyl, pyrimidynyl, pyrazynyl, indazolyl, purynyl, indolizynyl, quinolynyl, isoquinolynyl, quinazolynyl, carbazolyl, phenazynyl, phenothiazynyl, oxadiazolyl, pyranyl, triazolyl, isoindolyl, thiadiazolyl, and benzo[1,2,5]oxadiazolyl.

For the purposes of the present invention, a monocyclic ring system is taken to mean a monocyclic hydrocarbon group, which can be saturated, unsaturated, or aromatic and optionally have one or more heteroatoms as ring members. Such a monocyclic ring system can, for example, be condensed, ie anellated, or can be bonded with an aryl radical or a heteroaryl radical. The heteroatoms of such a monocyclic ring system can in each case be preferably selected from the group consisting of oxygen, nitrogen, and sulfur. The ring of the aforementioned monocyclic ring systems more preferably has in each case 1, 2, 3, 4, or 5 heteroatom(s) as a ring member(s), which are independently selected from the group consisting of oxygen, nitrogen, and sulfur. Preferably, the ring of the ring system is five-membered, six-membered, or seven-membered.

The ring system can be monosubstituted or polysubstituted and is preferably substituted by 1, 2, 3, 4, or 5 substituents, while the substituents can be preferably selected from the group consisting of F, Cl, Br, CN, NO₂, C$_{1-5}$ alkyl, C$_{1-5}$ alkoxy, —C(=O)C$_{1-5}$ alkyl, —C(=O)O—C$_{1-5}$ alkyl, —S(=O)₂—C$_{1-6}$ alkyl, —C(=O)C$_{1-5}$ perfluoroalkyl, —CF₃, CHF₂, CH₂F, and —NR$^a$R$^b$, in which R$^a$ and R$^b$ can be independently selected from the group consisting of H, methyl, ethyl, n-propyl, isopropyl, and unsubstituted phenyl, oxo (=O), thioxo (=S), I, —SF₅, —OH, —O—C$_{2-5}$ alkenyl, —O—CF₃, —O—CHF₂, —O—CH₂F, —S—CF₃, —S—CHF₂, —S—CH₂F, —SH, —S—C$_{1-5}$ alkyl, —C$_{1-5}$ alkyl, —C(=O)OH, —O—C(=O)C$_{1-5}$ alkyl, —O—C(=O)phenyl, —(CH₂)O—C(=O)C$_{1-5}$ alkyl, —(CH₂)O—C(=O)phenyl, —NH—C(=O)O—C$_{1-5}$ alkyl, —NH—C(=O)C$_{1-5}$ alkyl, —C(=O)H, —C(=O)NH₂, —C(=O)NH—C$_{1-5}$ alkyl, C(=O)N—(C$_{1-5}$ alkyl)₂, —S(=O)₂—NH₂, —S(=O)₂—NH—C$_{1-5}$ alkyl, —S(=O)₂—NH-phenyl, —(CH₂)benzo[b]furanyl, —O-phenyl, —S-phenyl, —S-benzyl, —O-benzyl, phenyl, and benzyl, wherein each of the cyclic moieties of the radicals —O—C(=O)phenyl, —(CH₂)O—C(=O)phenyl, —S(=O)₂—NH-phenyl, —O-phenyl, —S-phenyl, —S-benzyl, —O-benzyl, phenyl, —(CH₂)benzo[b]furanyl, and benzyl can be substituted by 1, 2, 3, 4, or 5 substituents independently selected from the group consisting of F, Cl, Br, —OH, —CF₃, —SF₅, —CN, —NO₂, —O—C$_{1-5}$ alkyl, —C$_{1-5}$ alkyl, —O—CF₃, —S—CF₃, phenyl, and —O-benzyl.

If one of the radicals R$^1$ to R$^{18}$ comprises a linear or branched alkylene group, these radicals can—unless otherwise stated—be unsubstituted or monosubstituted or polysubstituted, and are preferably substituted by 1, 2, 3, 4, or 5 substituents, while the substituents can be preferably independently selected from the group consisting of F, Cl, Br, C$_{1-6}$ alkoxy, hydroxy, CN, CF₃, CHF₃, CH₂F, —SH, —NO₂, unsubstituted phenyl and —NR$^a$R$^b$, in which R$^a$ and R$^b$ can be independently selected from the group consisting of H, C$_{1-3}$ alkyl, and unsubstituted phenyl. The alkylene group can also comprise one or more heteroatoms, preferably at least one oxygen atom and/or at least one sulfur atom, as a link(s).

The respective alkylene groups can—unless otherwise stated—also comprise one or more heteroatoms, preferably one or more oxygen atoms and/or one or more sulfur atoms and more preferably 1 or 2 oxygen atoms and/or sulfur atoms, as a link(s).

Mention may be made, for example, of alkylene groups such as —(CH₂)—, —(CH(CH₃))—, —(CH₂)₂—, and —(CH₂)₂—O—, —(CH₂)₃—, —(CH₂)₄—, —(CH₂)₅—, —(CH₂)₆—, —(CH₂)₇—, —(CH₂)₈—, —(CH₂)₉—, or —(CH₂)₁₀—.

Preference is given to substituted 1,4,8-triazaspiro[4,5]decan-2-one compounds of the above general formula I, in which R$^1$ stands for a hydrogen radical, for a linear or branched unsubstituted or at least monosubstituted C$_{1-10}$ alkyl radical optionally comprising at least one heteroatom as a link, for a linear or branched unsubstituted or at least monosubstituted C$_{2-10}$ alkenyl radical optionally comprising at least one heteroatom as a link, for a linear or branched unsubstituted or at least monosubstituted C$_{2-10}$ alkynyl radical optionally comprising at least one heteroatom as a link, for an unsubstituted or at least monosubstituted five-membered to fourteen-membered aryl radical or heteroaryl radical, which is can be bonded via a linear or branched C$_{1-5}$ alkylene group optionally comprising at least one heteroatom as a link, or for a —C(=O)OR$^7$ radical can be bonded via a linear or branched C$_{1-5}$ alkylene group, preferably for a hydrogen radical, or for a linear or branched unsubstituted C$_{1-5}$ alkyl radical, or for a linear or branched unsubstituted C$_{2-5}$ alkenyl radical, or for a linear or branched unsubstituted C$_{2-5}$ alkynyl radical, or for an unsubstituted or at least monosubstituted phenyl radical or an unsubstituted or at least monosubstituted naphthyl radical, which is can be bonded via a linear or branched C$_{1-5}$ alkylene group optionally comprising at least one oxygen atom as a link, or for a —C(=O)OR$^7$ radical can be bonded via a linear or branched C$_{1-3}$ alkylene group, more preferably for a hydrogen radical, or for a linear or branched unsubstituted C$_{1-4}$ alkyl radical, or for a linear or branched unsubstituted $C_{2-3}$ alkenyl radical, or for a linear or branched unsubstituted $C_{2-3}$ alkynyl radical, or for a phenyl radical or naphthyl radical, which is can be bonded via a —(CH$_2$) bridge, a —(CH$_2$)$_2$— bridge, a —(CH$_2$)$_3$— bridge or a —(CH$_2$)$_2$—O— bridge and is monosubstituted or polysubstituted by the same or different substituents selected from the group consisting of F, Cl, Br, CN, NO$_2$, $C_{1-5}$ alkyl, $C_{1-5}$ alkoxy, —C(═O)$C_{1-5}$ alkyl, —C(═O)O—$C_{1-5}$ alkyl, —S(═O)$_2$—$C_{1-6}$ alkyl, —C(═O)$C_{1-5}$ perfluoroalkyl, —CF$_3$, CHF$_2$, and CH$_2$F, or stands for a —C(═O)OR$^7$ radical can be bonded via a —(CH$_2$) group, and in each case the remaining radicals R$^2$-R$^{11}$ have the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Preference is also given to substituted 1,4,8-triazaspiro[4,5]decan-2-one compounds of the above general formula I, in which the radical R$^2$ stands for a hydrogen radical, or for a linear or branched unsubstituted or at least monosubstituted $C_{1-10}$ alkyl radical optionally comprising at least one heteroatom as a link, or for a linear or branched unsubstituted or at least monosubstituted $C_{2-10}$ alkenyl radical optionally comprising at least one heteroatom as a link, or for a linear or branched unsubstituted or at least monosubstituted $C_{2-10}$ alkynyl radical optionally comprising at least one heteroatom as a link, or for an unsubstituted or at least monosubstituted five-membered to fourteen-membered aryl or heteroaryl radical, which can be bonded via a linear or branched $C_{1-5}$ alkylene group optionally comprising at least one heteroatom as a link, preferably for a hydrogen radical, or for a linear or branched unsubstituted $C_{1-5}$ alkyl radical optionally comprising at least one oxygen atom and/or at least one sulfur atom as a link or for a phenyl or naphthyl radical, which can be monosubstituted or polysubstituted by the same or different substituents selected from the group consisting of F, Cl, Br, CN, NO$_2$, $C_{1-5}$ alkyl, $C_{1-5}$ alkoxy, —C(═O)$C_{1-5}$ alkyl, —C(═O)O—$C_{1-5}$ alkyl, —S(═O)$_2$—$C_{1-6}$ alkyl, —C(═O)$C_{1-5}$ perfluoroalkyl, —CF$_3$, CHF$_2$, and CH$_2$F and/or can be bonded via a —(CH$_2$) bridge, a —(CH$_2$)$_2$— bridge, a —(CH$_2$)$_3$— bridge or a —(CH$_2$)$_2$—O— bridge, more preferably for a hydrogen radical, or for a linear or branched unsubstituted $C_{1-5}$ alkyl radical optionally comprising at least one sulfur atom as a link or for a phenyl radical, wherein the phenyl radical can be monosubstituted or polysubstituted by the same or different substituents selected from the group consisting of F, Cl, Br, CN, NO$_2$, $C_{1-5}$ alkyl, $C_{1-5}$ alkoxy, —C(═O)$C_{1-5}$ alkyl, —C(═O)O—$C_{1-5}$ alkyl, —S(═O)$_2$—$C_{1-6}$ alkyl, —C(═O) $C_{1-5}$ perfluoroalkyl, —CF$_3$, CHF$_2$, and CH$_2$F and/or can be bonded via a —(CH$_2$) bridge, and in each case the remaining radicals R$^1$ and R$^3$ to R$^{11}$ have the meanings stated above, in each case optionally in the form one of the pure stereoisomers thereof, preferably enantiomers or diastereoisomers thereof, the racemates thereof or in the form of a mixture of stereoisomers and particularly of the enantiomers and/or diastereoisomers thereof in an arbitrary blending ratio, or in each case in the form of an appropriate salt, or in each case in the form of an appropriate solvate.

Preference is also given to substituted 1,4,8-triazaspiro[4,5]decan-2-one compounds of the above general formula I, in which the radical R$^4$ stands for an NR$^{10}$R$^{11}$ radical, or for a linear or branched unsubstituted or at least monosubstituted $C_{1-10}$ alkyl radical optionally comprising at least one heteroatom as a link, or for a linear or branched unsubstituted or at least monosubstituted $C_{2-10}$ alkenyl radical optionally comprising at least one heteroatom as a link, or for a linear or branched unsubstituted or at least monosubstituted $C_{2-10}$ alkynyl radical optionally comprising at least one heteroatom as a link, or for an unsubstituted or at least monosubstituted five-membered to fourteen-membered aryl radical or heteroaryl radical, which can be bonded via a linear or branched unsubstituted or at least monosubstituted $C_{1-5}$ alkylene group optionally comprising at least one heteroatom as a link and/or condensed with a five-membered or six-membered monocyclic ring system, or for an unsubstituted or at least monosubstituted $C_{3-8}$-cycloaliphatic radical, which optionally comprises at least one heteroatom as a ring member or which can be bonded via a linear or branched unsubstituted or at least monosubstituted $C_{1-5}$ alkylene group optionally comprising at least one heteroatom as a link and/or bridged by a linear or branched unsubstituted or at least monosubstituted $C_{1-5}$ alkylene group, preferably for an —NR$^{10}$R$^{11}$ radical, or for a linear or branched unsubstituted $C_{1-4}$ alkyl radical optionally comprising at least one oxygen atom and/or at least one sulfur atom as a link, or for a furyl (furanyl) radical, thienyl (thiophenyl) radical, phenyl radical, naphthyl radical, or 1,2,3,4-tetrahydroisoquinoline radical, while the cyclic radical can in each case be monosubstituted or polysubstituted by the same or different substituents selected from the group consisting of F, Cl, Br, CN, NO$_2$, $C_{1-5}$ alkyl, $C_{1-5}$ alkoxy, —C(═O)$C_{1-5}$ alkyl, —C(═O)O—$C_{1-5}$ alkyl, —S(═O)$_2$—$C_{1-6}$ alkyl, —C(═O)$C_{1-5}$ perfluoroalkyl, —CF$_3$, CHF$_2$, and CH$_2$F and/or be can be bonded via a —(CH$_2$)$_2$— or —(CH$_2$)$_3$ bridge, or for an unsubstituted C$_5$ or C$_3$ cycloaliphatic radical or one which is at least monosubstituted by an oxo group and which optionally comprises at least one heteroatom as a ring member, which can be bonded via a —(CH$_2$) bridge, a —(CH$_2$)$_2$— bridge, or a —(CH$_2$)$_3$— bridge and/or can be bridged ■ a —(C(CH$_3$)$_2$) group, more preferably for an —N(CH$_3$)$_2$ radical, or for a linear or branched unsubstituted $C_{1-4}$ alkyl radical, or for a thienyl (thiophenyl) radical, phenyl radical, or 1,2,3,4-tetrahydroisochinoline radical, and the cyclic radical can in each case be monosubstituted or polysubstituted by the same or different substituents selected from the group consisting of F, Cl, Br, CN, NO$_2$, $C_{1-5}$ alkyl, $C_{1-5}$ alkoxy, —C(═O)$C_{1-5}$ alkyl, —C(═O)O—$C_{1-5}$ alkyl, —S(═O)$_2$—$C_{1-6}$ alkyl, —C(═O)$C_{1-5}$ perfluoroalkyl, —CF$_3$, CHF$_2$, and CH$_2$F and/or be can be bonded over a —(CH$_2$) bridge, or for an unsubstituted C$_5$ or $C_{1-6}$ cycloaliphatic radical or one which is at least monosubstituted by an oxo group and which can be bonded via a —(CH$_2$) bridge and/or can be bridged by a —(C(CH$_3$)$_2$) group, and in each case the radicals R$^1$ to R$^3$ and R$^5$ to R$^{11}$ have the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Preference is also given to substituted 1,4,8-triazaspiro[4,5]decan-2-one compounds of the above general formula I in which the radical $R^5$ stands for a linear or branched unsubstituted or at least monosubstituted $C_{1-10}$ alkyl radical optionally comprising at least one heteroatom as a link, or for a linear or branched unsubstituted or at least monosubstituted $C_{2-10}$ alkenyl radical optionally comprising at least one heteroatom as a link, or for a linear or branched unsubstituted or at least monosubstituted $C_{2-10}$ alkynyl radical optionally comprising at least one heteroatom as a link, or for an unsubstituted or at least monosubstituted five-membered to fourteen-membered aryl or heteroaryl radical, which radicals can be bonded via a linear or branched unsubstituted or at least monosubstituted $C_{1-5}$ alkylene group optionally comprising at least one heteroatom as a link, for an unsubstituted or at least monosubstituted $C_{3-8}$ cycloaliphatic radical optionally comprising at least one heteroatom as a ring member and which can be bonded via a linear or branched unsubstituted or at least monosubstituted $C_{1-5}$ alkylene group optionally comprising at least one heteroatom as a link, or for a —C(=O)$OR^8$ radical or for a —C(=O)$OR^9$ radical can be bonded via a linear or branched $C_{1-5}$ alkylene group, preferably for a linear or branched $C_{1-5}$ alkyl radical optionally comprising at least one oxygen atom and/or at least one sulfur atom as a link, or for a linear or branched $C_{2-5}$ alkenyl radical optionally comprising at least one oxygen atom and/or at least one sulfur atom as a link, or for a linear or branched $C_{2-5}$ alkynyl radical optionally comprising at least one oxygen atom and/or at least one sulfur atom as a link, or for a furyl (furanyl) radical, thienyl (thiophenyl) radical, phenyl, or naphthyl radical, and the cyclic radical can in each case be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and/or can be bonded via a —($CH_2$) bridge, a —(CH($CH_3$)) bridge, a —($CH_2$)$_2$— bridge or a —($CH_2$)$_3$ bridge, or for an unsubstituted $C_4$, $C_5$ or $C_6$ cycloaliphatic radical optionally comprising at least one oxygen atom as a ring member, which can be bonded over a —($CH_2$) bridge, a —(CH($CH_3$)) bridge, a —($CH_2$)$_2$— bridge or a —($CH_2$)$_3$ bridge, or for a —C(=O)O—$R^8$ radical or a —C(=O)$OR^9$ radical can be bonded via a —($CH_2$) bridge, a —(CH($CH_3$)) bridge, a —($CH_2$)$_2$— bridge or a —($CH_2$)$_3$— bridge, more preferably for a linear or branched unsubstituted $C_{1-3}$ alkyl radical optionally comprising at least one oxygen atom as a link, or for a linear or branched unsubstituted $C_{2-3}$ alkenyl radical, or for a linear or branched unsubstituted $C_{2-3}$ alkynyl radical, or for a phenyl radical, while the phenyl radical can be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and/or can be bonded via a ($CH_2$) bridge, a —(CH($CH_3$)) bridge, a —($CH_2$)$_2$— bridge or a —($CH_2$)$_3$ bridge, or for an unsubstituted $C_5$ or $C_6$ cycloaliphatic radical which optionally comprises at least one oxygen atom as a ring member and which can be bonded via a —($CH_2$) bridge, a —(CH($CH_3$)) bridge, a —($CH_2$)$_2$— bridge or a —($CH_2$)$_3$ bridge, or for a C(=O)O—$C_2H_5$ radical or for a —C(=O)O—$R^9$ radical can be bonded via a —($CH_2$) bridge, a —(CH($CH_3$)) bridge, a —($CH_2$)$_2$— bridge or a —($CH_2$)$_3$ bridge, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Preference is also given to substituted 1,4,8-triazaspiro[4,5]decan-2-one compounds of the above general formula I, in which the radical $R^6$ stands for an unsubstituted or at least monosubstituted five-membered to fourteen-membered aryl or heteroaryl radical, which aryl or heteroaryl radical can be bonded via a linear or branched unsubstituted or at least monosubstituted $C_{1-5}$ alkylene group optionally comprising at least one heteroatom as a link, or for an unsubstituted or at least monosubstituted $C_{3-8}$ cycloaliphatic radical which optionally comprises at least one heteroatom as a ring member, or which can be bonded via a linear or branched unsubstituted or at least monosubstituted $C_{1-5}$ alkylene group optionally comprising at least one heteroatom as a link, preferably for a phenyl radical, which phenyl radical can be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and/or can be bonded via a —($CH_2$) bridge, a —(CH($CH_3$)) bridge, a —($CH_2$)$_2$— bridge, or a —($CH_2$)$_3$— bridge, or for an unsubstituted $C_5$- or $C_6$-cycloaliphatic radical, which can be bonded via a ($CH_2$) bridge, a —(CH($CH_3$)) bridge, a —($CH_2$)$_2$— bridge, or a —($CH_2$)$_3$— bridge, more preferably for a phenyl radical, which phenyl radical can be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and/or can be bonded via a ($CH_2$) bridge or a —($CH_2$)$_2$— bridge, or for a cyclohexyl radical, which can be bonded via a ($CH_2$) bridge or a —($CH_2$)$_2$ bridge, and in each case the radicals $R^1$ to $R^5$ and $R^7$ to $R^{11}$ have the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Furthermore, those substituted 1,4,8-triazaspiro[4,5]decan-2-one compounds of the above general formula I are preferred, in which the radicals $R^7$, $R^8$, $R^9$, and $R^{10}$, $R^{11}$, independently stand for a linear or branched $C_{1-5}$ alkyl radical, a linear or branched $C_{2-5}$ alkenyl radical, or a linear or branched $C_{2-5}$ alkynyl radical, preferably for a linear or optionally branched methyl radical, ethyl radical, n-propyl radical or isopropyl radical, and in each case the remaining radicals $R^1$ to $R^6$ have the meanings stated above, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Special preference is given to substituted 1,4,8-triazaspiro[4,5]decan-2-one compounds of the general formula I,

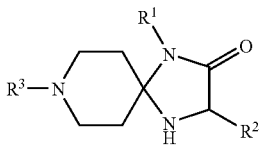

in which $R^1$ stands for a hydrogen radical, or for an alkyl radical selected from the group consisting of methyl, ethyl, n-propyl, isopropyl, n-butyl, isobutyl, sec-butyl, and tert-butyl, or for an alkenyl radical selected from the group consisting of vinyl and allyl, or for a propynyl radical, or for a phenyl radical a 1-naphthyl radical, or a 2-naphthyl radical, while the cyclic radical is can be bonded via a —$(CH_2)$ bridge, a —$(CH_2)_2$— bridge, a —$(CH_2)_2$— bridge, or a —$(CH_2)_2$—O— bridge and is optionally monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$, or for a —C(=O)O$R^7$ radical can be bonded via a $(CH_2)$ group, $R^2$ stands for a hydrogen radical, or for a linear or branched unsubstituted alkyl radical optionally comprising at least one sulfur atom as a link selected from the group consisting of methyl, ethyl, n-propyl, isopropyl, n-butyl, isobutyl, sec-butyl, tert-butyl, and 2-methylsulfanylethyl or for a phenyl radical or benzyl radical, each of which can be unsubstituted or monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$, $R^3$ stands for an S(=O)$_2$—$R^4$ group, or for a —C(=S)NH—$R^5$ group or for a —C(=O)NH—$R^6$ group, $R^4$ stands for a N—$(CH_3)_2$ radical, or for an alkyl radical selected from the group consisting of methyl, ethyl, n-propyl, isopropyl, n-butyl, isobutyl, sec-butyl, tert-butyl, or for a thienyl (thiophenyl) radical, phenyl radical, or 1,2,3,4-tetrahydroisoquinoline radical, and each cyclic radical can be unsubstituted or monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-15}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and/or can be bonded via a ($CH_2$) bridge, or for a 7,7-dimethyl-2-oxobicyclo[2.2.1]hept-1-ylmethyl radical, $R^5$ stands for an alkyl radical selected from the group consisting of methyl, ethyl, n-propyl, isopropyl, n-butyl, isobutyl, sec-butyl, tert-butyl, and 2-methoxyethyl, or for an alkenyl radical selected from the group consisting of vinyl and allyl, or for a propynyl radical, or for a phenyl radical, and the phenyl radical can be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O) $C_{1-5}$ perfluoroalkyl, —$CF_3$, $CHF_2$, and $CH_2F$ and/or can be bonded via a —$(CH_2)$— bridge, a —$(CH(CH_3))$— bridge, a —$(CH_2)_2$— bridge, or a —$(CH_2)_3$— bridge, or for a cyclohexyl or tetrahydrofuryl radical, which can be bonded via a —$(CH_2)$— bridge, or for a C(=O)O—$C_2H_5$ radical or for a —C(=O)O—$C_2H_5$ radical can be bonded via a —$(CH_2)$— bridge, a —$(CH(CH_3))$— bridge, a —$(CH_2)_2$— bridge, or a —$(CH_2)_3$— bridge, $R^6$ stands for a phenyl radical, which can be unsubstituted or monosubstituted or polysubstituted by the same or different substituents selected from the group consisting of F, Cl, Br, CN, $NO_2$, $C_{1-5}$ alkyl, $C_{1-5}$ alkoxy, —C(=O) $C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and/or be can be bonded via a —$(CH_2)$— bridge or a —$(CH_2)_2$— bridge, or for a cyclohexyl radical, which can be bonded via a —$(CH_2)$— bridge or a —$(CH_2)_2$— bridge, $R^7$, $R^8$, $R^9$, $R^{10}$, and $R^{11}$, each independently stand for a linear or branched $C_{1-5}$ alkyl radical, a linear or optionally branched $C_{2-5}$ alkenyl radical or a linear or branched $C_{2-5}$ alkynyl radical, preferably for a linear or branched methyl radical, ethyl radical, n-propyl radical or isopropyl radical.

in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Very special preference is given to substituted 1,4,8-triazaspiro[4,5]decan-2-one compounds of the above general formula I selected from the group consisting of

[1] 3-Isopropyl-8-(4-nitrobenzolsulfonyl)-1,4,8-triazaspiro[4,5]decan-2-one,

[2] 8-(2-Chlorobenzolsulfonyl)-3-isobutyl-1,4,8-triazaspiro[4,5]decan-2-one,

[3] 3-Benzyl-8-[2-(2,2,2-trifluoroacetyl)-1,2,3,4-tetrahydroisoquinolin-7-sulfonyl]-1,4,8-triazaspiro[4,5]decan-2-one,

[4] 3-Benzyl-8-(4-methoxy-2,3,6-trimethylbenzolsulfonyl)-1,4,8-triazaspiro[4,5]decan-2-one,

[5] 2-[8-(4-Butoxy-benzolsulfonyl)-2-oxo-1,4,8-triazaspiro[4,5]dec-1-ylmethyl]-benzonitrile,

[6] 2-{8-[4-(1,1-Dimethylpropyl)benzolesulfonyl]-2-oxo-1,4,8-triazaspiro[4,5]dec-1-ylmethyl}-benzonitrile,

[7] 3-Benzyl-8-(2-fluorobenzolsulfonyl)-1,4,8-triazaspiro[4,5]decan-2-one,

[8] 8-(2-Chlorobenzolsulfonyl)-3-isopropyl-1,4,8-triazaspiro[4,5]decan-2-one,

[9] 1-Benzyl-2-oxo-1,4,8-triazaspiro[4,5]decan-8-sulfonic acid dimethylamide,

[10] 3-[8-(4-Acetylbenzolsulfonyl)-3-(2-methylsulfanylethyl)-2-oxo-1,4,8-triazaspiro[4,5]dec-1-ylmethyl]-benzonitrile,
[11] 1-(2-Fluorobenzyl)-3-isopropyl-8-(4-methoxy-2,3,6-trimethylbenzolsulfonyl)-1,4,8-triazaspiro[4,5]decan-2-one,
[12] 1-Butyl-8-(5-chlorothiophen-2-sulfonyl)-3-(2-methylsulfanylethyl)-1,4,8-triazaspiro[4,5]decan-2-one,
[13] 8-(4-Acetylbenzolsulfonyl)-1-butyl-3-(2-methylsulfanylethyl)-1,4,8-triazaspiro[4,5]decan-2-one,
[14] 1-Benzyl-3-isopropyl-8-(2,4,6-trimethylbenzolsulfonyl)-1,4,8-triazaspiro[4,5]decan-2-one,
[15] Methyl 2-(1-butyl-3-isopropyl-2-oxo-1,4,8-triazaspiro[4,5]decan-8-sulfonyl)benzoate,
[16] 1,3-Dibenzyl-8-(thiophen-2-sulfonyl)-1,4,8-triazaspiro[4,5]decan-2-one,
[17] 8-(3-Chloro-4-fluorobenzolsulfonyl)-3-isopropyl-1-(2-phenoxy-ethyl)-1,4,8-triazaspiro[4,5]decan-2-one,
[18] 1-Butyl-3-(2-methylsulfanylethyl)-8-(toluol-3-sulfonyl)-1,4,8-triazaspiro[4,5]decan-2-one,
[19] 1-Butyl-8-(2,4-difluorobenzolsulfonyl)-3-isopropyl-1,4,8-triazaspiro[4,5]decan-2-one,
[20] 1,3-Dibenzyl-8-(2,5-dichlorothiophen-3-sulfonyl)-1,4,8-triazaspiro[4,5]decan-2-one,
[21] 3-Isopropyl-1-(2-phenoxy-ethyl)-8-(toluol-4-sulfonyl)-1,4,8-triazaspiro[4,5]decan-2-one,
[22] 3-Benzyl-1-butyl-8-(2-trifluoromethylbenzolsulfonyl)-1,4,8-triazaspiro[4,5]decan-2-one,
[23] Methyl 2-[1-(4-fluorobenzyl)-3-(2-methylsulfanylethyl)-2-oxo-1,4,8-triazaspiro[4,5]decan-8-sulfonyl]-benzoate,
[24] 1,3-Dibenzyl-8-(2,3,5,6-tetramethylbenzolsulfonyl)-1,4,8-triazaspiro[4,5]decan-2-one,
[25] 1-(4-Fluorobenzyl)-3-(2-methylsulfanylethyl)-8-(2-trifluoromethylbenzolsulfonyl)-1,4,8-triazaspiro[4,5]decan-2-one,
[26] 8-(4-Chloro-2,5-dimethylbenzolsulfonyl)-1-(4-fluorobenzyl)-3-(2-methylsulfanylethyl)-1,4,8-triazaspiro[4,5]decan-2-one,
[27] 1-Benzyl-8-(4-chloro-2,5-dimethylbenzolsulfonyl)-3-isobutyl-1,4,8-triazaspiro[4,5]decan-2-one,
[28] 3-Benzyl-1-butyl-8-[4-(1,1-dimethylpropyl)benzolesulfonyl]-1,4,8-triazaspiro[4,5]decan-2-one,
[29] 1,3-Dibenzyl-8-(3,4-dimethoxy-benzolsulfonyl)-1,4,8-triazaspiro[4,5]decan-2-one,
[30] 1-Butyl-8-(3,4-dimethoxy-benzolsulfonyl)-3-(2-methylsulfanylethyl)-1,4,8-triazaspiro[4,5]decan-2-one,
[31] 1,3-Dibenzyl-8-(4-methoxy-2,3,6-trimethylbenzolsulfonyl)-1,4,8-triazaspiro[4,5]decan-2-one,
[32] 1-Benzyl-8-ethanesulfonyl-3-(2-methylsulfanylethyl)-1,4,8-triazaspiro[4,5]decan-2-one,
[33] 3-Benzyl-1-butyl-8-(4-ethylbenzolsulfonyl)-1,4,8-triazaspiro[4,5]decan-2-one,
[34] 3-(2-Methylsulfanylethyl)-1-prop-2-ynyl-8-(3-trifluoromethylbenzolsulfonyl)-1,4,8-triazaspiro[4,5]decan-2-one,
[35] 1,3-Dibenzyl-8-(4-ethylbenzolsulfonyl)-1,4,8-triazaspiro[4,5]decan-2-one,
[36] 3-Benzyl-1-butyl-8-(3-chlorobenzolsulfonyl)-1,4,8-triazaspiro[4,5]decan-2-one,
[37] 1,3-Dibenzyl-8-(2-fluorobenzolsulfonyl)-1,4,8-triazaspiro[4,5]decan-2-one,
[38] Methyl 2-[1-(2-cyanobenzyl)-3-(2-methylsulfanylethyl)-2-oxo-1,4,8-triazaspiro[4,5]decan-8-sulfonyl]-benzoate,
[39] 3-Benzyl-1-prop-2-ynyl-8-(2-trifluoromethylbenzolsulfonyl)-1,4,8-triazaspiro[4,5]decan-2-one,
[40] 3-Benzyl-8-(3-chlorobenzolsulfonyl)-1-methyl-1,4,8-triazaspiro[4,5]decan-2-one,
[41] 1-Benzyl-8-[4-(1,1-dimethylpropyl)benzolesulfonyl]-3-(2-methylsulfanylethyl)-1,4,8-triazaspiro[4,5]decan-2-one,
[42] 8-(2,4-Difluorobenzolsulfonyl)-1-(3,5-dimethylbenzyl)-3-(2-methylsulfanylethyl)-1,4,8-triazaspiro[4,5]decan-2-one,
[43] 1,3-Dibenzyl-8-(4-nitrobenzolsulfonyl)-1,4,8-triazaspiro[4,5]decan-2-one,
[44] 1-(4-Fluorobenzyl)-3-(2-methylsulfanylethyl)-8-(toluol-4-sulfonyl)-1,4,8-triazaspiro[4,5]decan-2-one,
[45] 1,3-Dibenzyl-8-(toluol-4-sulfonyl)-1,4,8-triazaspiro[4,5]decan-2-one,
[46] Ethyl[3-benzyl-8-(2-methyl-5-nitrobenzolsulfonyl)-2-oxo-1,4,8-triazaspiro[4,5]dec-1-yl]-acetate,
[47] Ethyl[3-benzyl-8-(2-methansulfonylbenzolsulfonyl)-2-oxo-1,4,8-triazaspiro[4,5]dec-1-yl]-acetate,
[48] 3 Ethyl-benzyl-2-oxo-8-(thiophen-2-sulfonyl)-1,4,8-triazaspiro[4,5]dec-1-yl]-acetate,
[49] Methyl 4-(8-ethanesulfonyl-2-oxo-1,4,8-triazaspiro[4,5]dec-1-ylmethyl)benzoate,
[50] Ethyl[3-benzyl-8-(4-methoxy-benzolsulfonyl)-2-oxo-1,4,8-triazaspiro[4,5]dec-1-yl]-acetate,
[51] Methyl 4-(2-Oxo-8-benzolmethansulfonyl-1,4,8-triazaspiro[4,5]dec-1-ylmethyl)benzoate,
[52] 3-[3-Isopropyl-8-(4-nitrobenzolsulfonyl)-2-oxo-1,4,8-triazaspiro[4,5]dec-1-ylmethyl]-benzonitrile,
[53] Methyl 4-[8-(butan-1-sulfonyl)-2-oxo-1,4,8-triazaspiro[4,5]dec-1-ylmethyl]-benzoate,
[54] 1-Allyl-8-(2-methansulfonylbenzolsulfonyl)-3-(2-methylsulfanylethyl)-1,4,8-triazaspiro[4,5]decan-2-one,
[55] 1-(2-Fluorobenzyl)-2-oxo-1,4,8-triazaspiro[4,5]decan-8-sulfonic acid dimethylamide,
[56] 8-(7,7-Dimethyl-2-oxobicyclo[2.2.1]hept-1-ylmethansulfonyl)-1-(2-fluorobenzyl)-1,4,8-triazaspiro[4,5]decan-2-one,
[57] Ethyl[3-(2-methylsulfanylethyl)-2-oxo-8-benzolmethansulfonyl-1,4,8-triazaspiro[4,5]dec-1-yl]-acetate,
[58] 1-Allyl-3-(2-methylsulfanylethyl)-8-benzolmethansulfonyl-1,4,8-triazaspiro[4,5]decan-2-one,
[59] 3-[2-Oxo-8-(2,4,6-trimethylbenzolsulfonyl)-1,4,8-triazaspiro[4,5]dec-1-ylmethyl]-benzonitrile,
[60] Methyl 4-[2-oxo-8-(2,4,6-trimethylbenzolsulfonyl)-1,4,8-triazaspiro[4,5]dec-1-ylmethyl]-benzoate,
[61] Ethyl[3-benzyl-8-(5-chlorothiophen-2-sulfonyl)-2-oxo-1,4,8-triazaspiro[4,5]dec-1-yl]-acetate,
[62] Ethyl[3-benzyl-8-(butan-1-sulfonyl)-2-oxo-1,4,8-triazaspiro[4,5]dec-1-yl]-acetate,
[63] Ethyl[3-benzyl-2-oxo-8-(toluol-3-sulfonyl)-1,4,8-triazaspiro[4,5]dec-1-yl]-acetate,
[64] 1-(2-Fluorobenzyl)-8-(4-methoxy-benzolsulfonyl)-1,4,8-triazaspiro[4,5]decan-2-one,
[65] Ethyl[3-benzyl-2-oxo-8-(2-trifluoromethylbenzolsulfonyl)-1,4,8-triazaspiro[4,5]dec-1-yl]-acetate,
[66] Ethyl(8-benzolsulfonyl-3-benzyl-2-oxo-1,4,8-triazaspiro[4,5]dec-1-yl)acetate,
[67] Ethyl[3-benzyl-2-oxo-8-(4-propylbenzolsulfonyl)-1,4,8-triazaspiro[4,5]dec-1-yl]-acetate,
[68] Ethyl(3-benzyl-2-oxo-8-benzolmethansulfonyl-1,4,8-triazaspiro[4,5]dec-1-yl)acetate,
[69] Ethyl[3-benzyl-8-(3-chloro-4-fluorobenzolsulfonyl)-2-oxo-1,4,8-triazaspiro[4,5]dec-1-yl]-acetate,
[70] 1-Allyl-3-isopropyl-8-(2,4,6-trimethylbenzolsulfonyl)-1,4,8-triazaspiro[4,5]decan-2-one,
[71] 8-Benzolsulfonyl-3-benzyl-1-(2-fluorobenzyl)-1,4,8-triazaspiro[4,5]decan-2-one,

[72] Ethyl[3-benzyl-2-oxo-8-(2,4,6-trimethylbenzolsulfonyl)-1,4,8-triazaspiro[4,5]dec-1-yl]-acetate,
[73] Ethyl[3-benzyl-8-(4-butoxy-benzolsulfonyl)-2-oxo-1,4,8-triazaspiro[4,5]dec-1-yl]-acetate,
[74] Ethyl[3-benzyl-8-(2,5-dimethoxy-benzolsulfonyl)-2-oxo-1,4,8-triazaspiro[4,5]dec-1-yl]-acetate,
[75] 3-(2-Methylsulfanylethyl)-1-naphthalin-2-ylmethyl-2-oxo-1,4,8-triazaspiro[4,5]decan-8-sulfonic acid dimethylamide,
[76] 1-(3-Cyanobenzyl)-3-isopropyl-2-oxo-1,4,8-triazaspiro[4,5]decan-8-sulfonic acid dimethylamide,
[77] 3-{3-Isopropyl-2-oxo-8-[2-(2,2,2-trifluoroacetyl)-1,2,3,4-tetrahydroisoquinolin-7-sulfonyl]-1,4,8-triazaspiro[4,5]dec-1-ylmethyl}-benzonitrile,
[78] 1-Allyl-3-(2-methylsulfanylethyl)-8-[2-(2,2,2-trifluoroacetyl)-1,2,3,4-tetrahydroisoquinolin-7-sulfonyl]-1,4,8-triazaspiro[4,5]decan-2-one,
[79] 1-Allyl-8-(4-methoxy-2,3,6-trimethylbenzolsulfonyl)-3-(2-methylsulfanylethyl)-1,4,8-triazaspiro[4,5]decan-2-one,
[80] Methyl 2-(3-benzyl-1-ethoxycarbonylmethyl-2-oxo-1,4,8-triazaspiro[4,5]decan-8-sulfonyl)benzoate,
[81] 3-Benzyl-1-(2-fluorobenzyl)-8-(2-trifluoromethylbenzolsulfonyl)-1,4,8-triazaspiro[4,5]decan-2-one,
[82] 8-(2-Chlorobenzolsulfonyl)-3-(2-methylsulfanylethyl)-1-(2-nitrobenzyl)-1,4,8-triazaspiro[4,5]decan-2-one,
[83] 1-Allyl-3-(2-methylsulfanylethyl)-8-(toluol-3-sulfonyl)-1,4,8-triazaspiro[4,5]decan-2-one,
[84] Ethyl[8-(2-chlorobenzolsulfonyl)-3-(2-methylsulfanylethyl)-2-oxo-1,4,8-triazaspiro[4,5]dec-1-yl]-acetate,
[85] 3-benzyl-1-(2-fluorobenzyl)-8-(toluol-4-sulfonyl)-1,4,8-triazaspiro[4,5]decan-2-one,
[86] Methyl 4-[8-(2,5-dichlorothiophen-3-sulfonyl)-2-oxo-1,4,8-triazaspiro[4,5]dec-1-ylmethyl]-benzoate,
[87] 3-[8-(4-Fluorobenzolsulfonyl)-3-isopropyl-2-oxo-1,4,8-triazaspiro[4,5]dec-1-ylmethyl]-benzonitrile,
[88] 8-(2,5-Dimethoxy-benzolsulfonyl)-3-(2-methylsulfanylethyl)-1-(2-nitrobenzyl)-1,4,8-triazaspiro[4,5]decan-2-one,
[89] 8-(3-Chloro-4-fluorobenzolsulfonyl)-1-(2-fluorobenzyl)-1,4,8-triazaspiro[4,5]decan-2-one,
[90] 1-(2-Fluorobenzyl)-8-(toluol-3-sulfonyl)-1,4,8-triazaspiro[4,5]decan-2-one,
[91] 1-(2,6-Dichlorobenzyl)-8-(4,5-dichlorothiophen-2-sulfonyl)-3-isobutyl-1,4,8-triazaspiro[4,5]decan-2-one,
[92] 8-(5-Chlorothiophen-2-sulfonyl)-1-(2-fluorobenzyl)-1,4,8-triazaspiro[4,5]decan-2-one,
[93] 3-Benzyl-1-(2-fluorobenzyl)-8-(4-propylbenzolsulfonyl)-1,4,8-triazaspiro[4,5]decan-2-one,
[94] 3-[8-(Butan-1-sulfonyl)-3-isopropyl-2-oxo-1,4,8-triazaspiro[4,5]dec-1-ylmethyl]-benzonitrile,
[95] 3-[8-(2-Methansulfonylbenzolsulfonyl)-2-oxo-1,4,8-triazaspiro[4,5]dec-1-ylmethyl]-benzonitrile,
[96] 8-(2-Fluorobenzolsulfonyl)-1-(2-fluorobenzyl)-1,4,8-triazaspiro[4,5]decan-2-one,
[97] Methyl 2-[1-(3-cyanobenzyl)-3-isopropyl-2-oxo-1,4,8-triazaspiro[4,5]decan-8-sulfonyl]-benzoate,
[98] 3-Benzyl-1-(2-fluorobenzyl)-8-(5-fluoro-2-methylbenzolsulfonyl)-1,4,8-triazaspiro[4,5]decan-2-one,
[99] 1-Allyl-8-(4-methoxy-benzolsulfonyl)-3-(2-methylsulfanylethyl)-1,4,8-triazaspiro[4,5]decan-2-one,
[100] 1-(3,5-Dimethylbenzyl)-3-isobutyl-8-(thiophen-2-sulfonyl)-1,4,8-triazaspiro[4,5]decan-2-one,
[101] 3-(2-Methylsulfanylethyl)-8-(4-nitrobenzolsulfonyl)-1-(2-nitrobenzyl)-1,4,8-triazaspiro[4,5]decan-2-one,
[102] 2-Isobutyl-3-oxo-1,4,8-triazaspiro[4,5]decan-8-thiocarboxylic acid o-tolylamide,
[103] 2-Benzyl-3-oxo-1,4,8-triazaspiro[4,5]decan-8-thiocarboxylic acid isopropylamide,
[104] 1-Butyl-3-isopropyl-2-oxo-1,4,8-triazaspiro[4,5]decan-8-thiocarboxylic acid (tetrahydrofuran-2-ylmethyl)amide,
[105] Ethyl 3-{[1-methyl-3-(2-methylsulfanylethyl)-2-oxo-1,4,8-triazaspiro[4,5]decan-8-carbothioyl]-amino}-butyrate,
[106] 1-Allyl-3-isopropyl-2-oxo-1,4,8-triazaspiro[4,5]decan-8-thiocarboxylic acid isopropylamide,
[107] 1-Butyl-3-isopropyl-2-oxo-1,4,8-triazaspiro[4,5]decan-8-thiocarboxylic acid isopropylamide
[108] 3-Benzyl-1-(2-fluorobenzyl)-2-oxo-1,4,8-triazaspiro[4,5]decan-8-thiocarboxylic acid (2-methoxy-benzol)amide,
[109] Ethyl[8-Isopropylthiocarbamoyl-3-(2-methylsulfanylethyl)-2-oxo-1,4,8-triazaspiro[4,5]dec-1-yl]-4acetate,
[110] 1-Methyl-3-(2-methylsulfanylethyl)-2-oxo-1,4,8-triazaspiro[4,5]decan-8-thiocarboxylic acid m-tolylamide,
[111] 1-Methyl-3-(2-methylsulfanylethyl)-2-oxo-1,4,8-triazaspiro[4,5]decan-8-thiocarboxylic acid 4-methoxy-benzylamide,
[112] 2-Isobutyl-3-oxo-1,4,8-triazaspiro[4,5]decan-8-thiocarboxylic acid (4-fluorobenzol)amide,
[113] Ethyl[8-ethoxycarbonylaminocarbothioyl-3-(2-methylsulfanylethyl)-2-oxo-1,4,8-triazaspiro[4,5]dec-1-yl]-acetate
[114] Ethyl 3-{[1-ethoxycarbonylmethyl-3-(2-methylsulfanylethyl)-2-oxo-1,4,8-triazaspiro[4,5]decan-8-carbothioyl]-amino}-butyrate,
[115] 1-Allyl-3-isopropyl-2-oxo-1,4,8-triazaspiro[4,5]decan-8-thiocarboxylic acid (2-methoxy-benzol)amide,
[116] 1-Butyl-3-isopropyl-2-oxo-1,4,8-triazaspiro[4,5]decan-8-thiocarboxylic acid benzolamide,
[117] 1-Butyl-3-isopropyl-2-oxo-1,4,8-triazaspiro[4,5]decan-8-thiocarboxylic acid (2,5-dichlorobenzol)amide,
[118] 3-Benzyl-1-methyl-2-oxo-1,4,8-triazaspiro[4,5]decan-8-thiocarboxylic acid (2,5-difluorobenzol)amide,
[119] 1-Methyl-3-(2-methylsulfanylethyl)-2-oxo-1,4,8-triazaspiro[4,5]decan-8-thiocarboxylic acid (2-bromobenzol)amide,
[120] 1-Butyl-3-(2-methylsulfanylethyl)-2-oxo-1,4,8-triazaspiro[4,5]decan-8-thiocarboxylic acid (2,5-dichlorobenzol)amide,
[121] 3-(2-Methylsulfanylethyl)-1-naphthalin-2-ylmethyl-2-oxo-1,4,8-triazaspiro[4,5]decan-8-thiocarboxylic acid (2-methoxy-ethyl)amide,
[122] 1-Butyl-3-isopropyl-2-oxo-1,4,8-triazaspiro[4,5]decan-8-thiocarboxylic acid (2-fluorobenzol)amide,
[123] 3-Isobutyl-2-oxo-1-prop-2-ynyl-1,4,8-triazaspiro[4,5]decan-8-thiocarboxylic acid allylamide,
[124] 1-Butyl-3-isopropyl-2-oxo-1,4,8-triazaspiro[4,5]decan-8-thiocarboxylic acid m-tolylamide,
[125] 1-Allyl-3-isopropyl-2-oxo-1,4,8-triazaspiro[4,5]decan-8-thiocarboxylic acid (4-fluorobenzol)amide,
[126] Methyl 4-(8-allylthiocarbamoyl-3-isopropyl-2-oxo-1,4,8-triazaspiro[4,5]dec-1-ylmethyl)benzoate,
[127] 1-Butyl-3-(2-methylsulfanylethyl)-2-oxo-1,4,8-triazaspiro[4,5]decan-8-thiocarboxylic acid (2-methoxy-benzol)amide,
[128] 1-Allyl-3-isopropyl-2-oxo-1,4,8-triazaspiro[4,5]decan-8-thiocarboxylic acid (2,5-difluorobenzol)amide,
[129] 1-(2-Cyanobenzyl)-3-(2-methylsulfanylethyl)-2-oxo-1,4,8-triazaspiro[4,5]decan-8-thiocarboxylic acid allylamide,

[130] 1-(3-Cyanobenzyl)-3-(2-methylsulfanylethyl)-2-oxo-1,4,8-triazaspiro[4,5]decan-8-thiocarboxylic acid allylamide,

[131] Ethyl 3-[(3-benzyl-1-methyl-2-oxo-1,4,8-triazaspiro[4,5]decan-8-carbothioyl)amino]-butyrate,

[132] 1-Butyl-3-(2-methylsulfanylethyl)-2-oxo-1,4,8-triazaspiro[4,5]decan-8-thiocarboxylic acid cyclohexylmethylamide,

[133] 1-Methyl-3-(2-methylsulfanylethyl)-2-oxo-1,4,8-triazaspiro[4,5]decan-8-thiocarboxylic acid (4-chlorobenzol)amide,

[134] 1-Methyl-3-(2-methylsulfanylethyl)-2-oxo-1,4,8-triazaspiro[4,5]decan-8-thiocarboxylic acid 4-fluorobenzylamide,

[135] Methyl 4-[8-(2,6-dichlorobenzolthiocarbamoyl)-3-isopropyl-2-oxo-1,4,8-triazaspiro[4,5]dec-1-ylmethyl]-benzoate,

[136] 1-Benzyl-3-isopropyl-2-oxo-1,4,8-triazaspiro[4,5]decan-8-thiocarboxylic acid (2,5-dichlorobenzol)amide,

[137] Methyl 4-{3-isopropyl-2-oxo-8-[(tetrahydrofuran-2-ylmethyl)thiocarbamoyl]-1,4,8-triazaspiro[4,5]dec-1-ylmethyl}-benzoate,

[138] 1-Methyl-3-(2-methylsulfanylethyl)-2-oxo-1,4,8-triazaspiro[4,5]decan-8-thiocarboxylic acid (2,5-difluorobenzol)amide,

[139] 1-Benzyl-3-(2-methylsulfanylethyl)-2-oxo-1,4,8-triazaspiro[4,5]decan-8-thiocarboxylic acid (4-isopropylbenzol)amide,

[140] 1-Benzyl-3-(2-methylsulfanylethyl)-2-oxo-1,4,8-triazaspiro[4,5]decan-8-thiocarboxylic acid (2,5-difluorobenzol)amide,

[141] 1-(2-Cyanobenzyl)-3-isobutyl-2-oxo-1,4,8-triazaspiro[4,5]decan-8-thiocarboxylic acid (3-acetylbenzol)amide,

[142] 1-Butyl-3-isopropyl-2-oxo-1,4,8-triazaspiro[4,5]decan-8-thiocarboxylic acid (3-chlorobenzol)amide,

[143] Methyl 2-[(1-butyl-3-isopropyl-2-oxo-1,4,8-triazaspiro[4,5]decan-8-carbothioyl)amino]-benzoate,

[144] Ethyl(3-benzyl-8-ethoxycarbonylaminocarbothioyl-2-oxo-1,4,8-triazaspiro[4,5]dec-1-yl)acetate,

[145] Methyl 2-[(3-benzyl-1-ethoxycarbonylmethyl-2-oxo-1,4,8-triazaspiro[4,5]decan-8-carbothioyl)amino]-benzoate,

[146] Ethyl[1-(2-cyanobenzyl)-3-(2-methylsulfanylethyl)-2-oxo-1,4,8-triazaspiro[4,5]decan-8-carbothioyl]-carbamate,

[147] 1-(2-Cyanobenzyl)-3-(2-methylsulfanylethyl)-2-oxo-1,4,8-triazaspiro[4,5]decan-8-thiocarboxylic acid (2-chloro-5-trifluoromethylbenzol)amide,

[148] 3-(2-Methylsulfanylethyl)-1-naphthalin-2-ylmethyl-2-oxo-1,4,8-triazaspiro[4,5]decan-8-thiocarboxylic acid (1-benzol-ethyl)amide,

[149] 1-Allyl-3-isopropyl-2-oxo-1,4,8-triazaspiro[4,5]decan-8-thiocarboxylic acid pentafluorobenzolamide-amide,

[150] 1-Butyl-3-isopropyl-2-oxo-1,4,8-triazaspiro[4,5]decan-8-thiocarboxylic acid 4-chlorobenzylamide,

[151] 3-(2-Methylsulfanylethyl)-1-naphthalin-2-ylmethyl-2-oxo-1,4,8-triazaspiro[4,5]decan-8-thiocarboxylic acid o-tolylamide,

[152] 1-Butyl-3-isopropyl-2-oxo-1,4,8-triazaspiro[4,5]decan-8-thiocarboxylic acid pentafluorobenzolamide-amide,

[153] Methyl 2-{[1-(2-cyanobenzyl)-3-(2-methylsulfanylethyl)-2-oxo-1,4,8-triazaspiro[4,5]decan-8-carbothioyl]-amino}-benzoate,

[154] 1-Benzyl-3-isopropyl-2-oxo-1,4,8-triazaspiro[4,5]decan-8-thiocarboxylic acid pentafluorobenzolamide-amide,

[155] 1-Benzyl-3-isopropyl-2-oxo-1,4,8-triazaspiro[4,5]decan-8-thiocarboxylic acid (2-methoxy-benzol)amide,

[156] 1-Benzyl-3-isopropyl-2-oxo-1,4,8-triazaspiro[4,5]decan-8-thiocarboxylic acid benzolamide,

[157] 1-Benzyl-3-isopropyl-2-oxo-1,4,8-triazaspiro[4,5]decan-8-thiocarboxylic acid (2,5-difluorobenzol)amide,

[158] 1-Butyl-3-(2-methylsulfanylethyl)-2-oxo-1,4,8-triazaspiro[4,5]decan-8-thiocarboxylic acid (4-ethoxy-benzol)amide,

[159] Ethyl[3-benzyl-8-(cyclohexylmethylthiocarbamoyl)-2-oxo-1,4,8-triazaspiro[4,5]dec-1-yl]-acetate,

[160] 1-Butyl-3-(2-methylsulfanylethyl)-2-oxo-1,4,8-triazaspiro[4,5]decan-8-thiocarboxylic acid benzylamide,

[161] 1-(2-Cyanobenzyl)-3-(2-methylsulfanylethyl)-2-oxo-1,4,8-triazaspiro[4,5]decan-8-thiocarboxylic acid m-tolylamide,

[162] 1-Allyl-3-isopropyl-2-oxo-1,4,8-triazaspiro[4,5]decan-8-thiocarboxylic acid 4-fluorobenzylamide,

[163] 3-Isobutyl-2-oxo-1-prop-2-ynyl-1,4,8-triazaspiro[4,5]decan-8-thiocarboxylic acid (3-acetylbenzol)amide,

[164] Methyl 4-(3-isopropyl-2-oxo-8-pentafluorobenzolthiocarbamoyl-1,4,8-triazaspiro[4,5]dec-1-ylmethyl)benzoate,

[165] 3-(2-Methylsulfanylethyl)-1-naphthalin-2-ylmethyl-2-oxo-1,4,8-triazaspiro[4,5]decan-8-thiocarboxylic acid (3-acetylbenzol)amide,

[166] 3-Benzyl-1-(2-fluorobenzyl)-2-oxo-1,4,8-triazaspiro[4,5]decan-8-thiocarboxylic acid m-tolylamid

[167] Methyl 4-(8-ethoxycarbonylaminocarbothioyl-3-isopropyl-2-oxo-1,4,8-triazaspiro[4,5]dec-1-ylmethyl)benzoate,

[168] 1-(4-Fluorobenzyl)-3-(2-methylsulfanylethyl)-2-oxo-1,4,8-triazaspiro[4,5]decan-8-thiocarboxylic acid (tetrahydrofuran-2-ylmethyl)amide,

[169] 1-(2-Cyanobenzyl)-3-isobutyl-2-oxo-1,4,8-triazaspiro[4,5]decan-8-thiocarboxylic acid (3,5-bis-trifluoromethylbenzol)amide,

[170] 1-(2-Cyanobenzyl)-3-isobutyl-2-oxo-1,4,8-triazaspiro[4,5]decan-8-thiocarboxylic acid benzylamide,

[171] 3-Benzyl-1-(2-fluorobenzyl)-2-oxo-1,4,8-triazaspiro[4,5]decan-8-thiocarboxylic acid cyclohexylmethylamide,

[172] 1-(3-Cyanobenzyl)-3-(2-methylsulfanylethyl)-2-oxo-1,4,8-triazaspiro[4,5]decan-8-thiocarboxylic acid (4-chlorobenzol)amide,

[173] 1-Butyl-3-(2-methylsulfanylethyl)-2-oxo-1,4,8-triazaspiro[4,5]decan-8-thiocarboxylic acid pentafluorobenzolamide-amide,

[174] Ethyl[3-benzyl-1-(2-fluorobenzyl)-2-oxo-1,4,8-triazaspiro[4,5]decan-8-carbothioyl]-carbamate,

[175] 3-Benzyl-1-methyl-2-oxo-1,4,8-triazaspiro[4,5]decan-8-thiocarboxylic acid 4-chlorobenzylamide,

[176] 1-(4-Fluorobenzyl)-3-(2-methylsulfanylethyl)-2-oxo-1,4,8-triazaspiro[4,5]decan-8-thiocarboxylic acid isopropylamide,

[177] 1-Benzyl-3-isopropyl-2-oxo-1,4,8-triazaspiro[4,5]decan-8-thiocarboxylic acid (3,5-dichlorobenzol)amide,

[178] Ethyl[1-(3-cyanobenzyl)-3-(2-methylsulfanylethyl)-2-oxo-1,4,8-triazaspiro[4,5]decan-8-carbothioyl]-carbamate,

[179] 1-Benzyl-3-isopropyl-2-oxo-1,4,8-triazaspiro[4,5]decan-8-thiocarboxylic acid 4-fluorobenzylamide,

[180] 1-Allyl-3-isopropyl-2-oxo-1,4,8-triazaspiro[4,5]decan-8-thiocarboxylic acid (3,5-dichlorobenzol)amide,

[181] 1-(3-Cyanobenzyl)-3-(2-methylsulfanylethyl)-2-oxo-1,4,8-triazaspiro[4,5]decan-8-thiocarboxylic acid (1-benzol-ethyl)amide,

[182] 1-(4-Fluorobenzyl)-3-(2-methylsulfanylethyl)-2-oxo-1,4,8-triazaspiro[4,5]decan-8-thiocarboxylic acid 4-fluorobenzylamide,

[183] 1-(2-Cyanobenzyl)-3-(2-methylsulfanylethyl)-2-oxo-1,4,8-triazaspiro[4,5]decan-8-thiocarboxylic acid (2-methoxy-benzol)amide,
[184] 1-(3-Cyanobenzyl)-3-(2-methylsulfanylethyl)-2-oxo-1,4,8-triazaspiro[4,5]decan-8-thiocarboxylic acid (2-methoxy-benzol)amide,
[185] 1-(3-Cyanobenzyl)-3-(2-methylsulfanylethyl)-2-oxo-1,4,8-triazaspiro[4,5]decan-8-thiocarboxylic acid 4-chlorobenzylamide,
[186] 1-(4-Fluorobenzyl)-3-(2-methylsulfanylethyl)-2-oxo-1,4,8-triazaspiro[4,5]decan-8-thiocarboxylic acid o-tolylamide,
[187] 3-Benzyl-1-(2-fluorobenzyl)-2-oxo-1,4,8-triazaspiro[4,5]decan-8-thiocarboxylic acid (2,6-dichlorobenzol)amide,
[188] 3-Benzyl-1-(2-fluorobenzyl)-2-oxo-1,4,8-triazaspiro[4,5]decan-8-thiocarboxylic acid (2-chloro-5-trifluoromethylbenzol)amide,
[189] 1-Butyl-3-(2-methylsulfanylethyl)-2-oxo-1,4,8-triazaspiro[4,5]decan-8-thiocarboxylic acid (4-fluorobenzol)amide,
[190] 3-Isobutyl-2-oxo-1-prop-2-ynyl-1,4,8-triazaspiro[4,5]decan-8-thiocarboxylic acid (2,6-dichlorobenzol)amide,
[191] Methyl 4-[8-(4-chlorobenzylthiocarbamoyl)-3-isopropyl-2-oxo-1,4,8-triazaspiro[4,5]dec-1-ylmethyl]-benzoate,
[192] 1-(4-Fluorobenzyl)-3-(2-methylsulfanylethyl)-2-oxo-1,4,8-triazaspiro[4,5]decan-8-thiocarboxylic acid (3-cyanobenzol)amide,
[193] 1-(2-Cyanobenzyl)-3-(2-methylsulfanylethyl)-2-oxo-1,4,8-triazaspiro[4,5]decan-8-thiocarboxylic acid 4-chlorobenzylamide,
[194] 1-Methyl-3-(2-methylsulfanylethyl)-2-oxo-1,4,8-triazaspiro[4,5]decan-8-thiocarboxylic acid (3-trifluoromethylbenzol)amide,
[195] 3-Isobutyl-2-oxo-1-prop-2-ynyl-1,4,8-triazaspiro[4,5]decan-8-thiocarboxylic acid (3,5-dichlorobenzol)amide,
[196] 1-(4-Fluorobenzyl)-3-(2-methylsulfanylethyl)-2-oxo-1,4,8-triazaspiro[4,5]decan-8-thiocarboxylic acid (1-benzol-ethyl)amide,
[197] 3-Benzyl-1-(2-fluorobenzyl)-2-oxo-1,4,8-triazaspiro[4,5]decan-8-thiocarboxylic acid 4-chlorobenzylamide,
[198] 2-Isopropyl-3-oxo-1,4,8-triazaspiro[4,5]decan-8-thiocarboxylic acid (4-fluorobenzol)amide,
[199] 1-Benzyl-3-isopropyl-2-oxo-1,4,8-triazaspiro[4,5]decan-8-thiocarboxylic acid benzylamide,
[200] 1-(4-Fluorobenzyl)-3-(2-methylsulfanylethyl)-2-oxo-1,4,8-triazaspiro[4,5]decan-8-thiocarboxylic acid (4-ethoxy-benzol)amide,
[201] 3-Benzyl-1-(2-fluorobenzyl)-2-oxo-1,4,8-triazaspiro[4,5]decan-8-thiocarboxylic acid (3-acetylbenzol)amide,
[202] 3-Benzyl-1-methyl-2-oxo-1,4,8-triazaspiro[4,5]decan-8-carboxylic acid cyclohexylamide,
[203] Ethyl[3-(2-methylsulfanylethyl)-2-oxo-8-benzolcarbamoyl-1,4,8-triazaspiro[4,5]dec-1-yl]-acetate,
[204] 1-Allyl-3-isopropyl-2-oxo-1,4,8-triazaspiro[4,5]decan-8-carboxylic acid (2,5-dimethoxy-benzol)amide,
[205] 1-Methyl-3-(2-methylsulfanylethyl)-2-oxo-1,4,8-triazaspiro[4,5]decan-8-carboxylic acid (3-fluorobenzol)amide,
[206] Methyl 4-(8-cyclohexylcarbamoyl-3-isopropyl-2-oxo-1,4,8-triazaspiro[4,5]dec-1-ylmethyl)benzoate,
[207] 1-Butyl-3-(2-methylsulfanylethyl)-2-oxo-1,4,8-triazaspiro[4,5]decan-8-carboxylic acid benzolamide,
[208] 1-Benzyl-3-(2-methylsulfanylethyl)-2-oxo-1,4,8-triazaspiro[4,5]decan-8-carboxylic acid (3-cyanobenzol)amide,
[209] 1-Allyl-3-isopropyl-2-oxo-1,4,8-triazaspiro[4,5]decan-8-carboxylic acid (2,5-difluorobenzol)amide,
[210] 1-Butyl-3-(2-methylsulfanylethyl)-2-oxo-1,4,8-triazaspiro[4,5]decan-8-carboxylic acid (3,4,5-trimethoxy-benzol)amide,
[211] 1-Benzyl-3-(2-methylsulfanylethyl)-2-oxo-1,4,8-triazaspiro[4,5]decan-8-carboxylic acid (4-chloro-3-trifluoromethylbenzol)amide,
[212] 1-Methyl-3-(2-methylsulfanylethyl)-2-oxo-1,4,8-triazaspiro[4,5]decan-8-carboxylic acid (5-chloro-2-methoxy-benzol)amide,
[213] 1-Benzyl-3-(2-methylsulfanylethyl)-2-oxo-1,4,8-triazaspiro[4,5]decan-8-carboxylic acid (4-ethoxy-benzol)amide,
[214] 1-Benzyl-3-(2-methylsulfanylethyl)-2-oxo-1,4,8-triazaspiro[4,5]decan-8-carboxylic acid (3-acetylbenzol)amide,
[215] Ethyl 3-[(1-butyl-3-isopropyl-2-oxo-1,4,8-triazaspiro[4,5]decan-8-carbonyl)amino]-benzoate,
[216] 1-Butyl-3-isopropyl-2-oxo-1,4,8-triazaspiro[4,5]decan-8-carboxylic acid (2,5-dimethoxy-benzol)amide,
[217] 1-(2-Cyanobenzyl)-3-isobutyl-2-oxo-1,4,8-triazaspiro[4,5]decan-8-carboxylic acid 3,4-dichlorobenzylamide,
[218] 1-(2-Cyanobenzyl)-3-isobutyl-2-oxo-1,4,8-triazaspiro[4,5]decan-8-carboxylic acid (2,5-difluorobenzol)amide,
[219] 1-Butyl-3-(2-methylsulfanylethyl)-2-oxo-1,4,8-triazaspiro[4,5]decan-8-carboxylic acid 3,4-dichlorobenzylamide,
[220] 1-Allyl-3-isopropyl-2-oxo-1,4,8-triazaspiro[4,5]decan-8-carboxylic acid (4-trifluoromethoxy-benzol)amide,
[221] 1-Butyl-3-(2-methylsulfanylethyl)-2-oxo-1,4,8-triazaspiro[4,5]decan-8-carboxylic acid (4-ethoxy-benzol)amide,
[222] 1-Methyl-3-(2-methylsulfanylethyl)-2-oxo-1,4,8-triazaspiro[4,5]decan-8-carboxylic acid (4-trifluoromethoxy-benzol)amide,
[223] Methyl 4-[3-isopropyl-8-(3-methoxy-benzolcarbamoyl)-2-oxo-1,4,8-triazaspiro[4,5]dec-1-ylmethyl]-benzoate,
[224] 1-(2-Cyanobenzyl)-3-(2-methylsulfanylethyl)-2-oxo-1,4,8-triazaspiro[4,5]decan-8-carboxylic acid benzolamide,
[225] Ethyl[3-benzyl-8-(3,4-dichlorobenzylcarbamoyl)-2-oxo-1,4,8-triazaspiro[4,5]dec-1-yl]-acetate,
[226] 1-(2-Cyanobenzyl)-3-(2-methylsulfanylethyl)-2-oxo-1,4,8-triazaspiro[4,5]decan-8-carboxylic acid (3-fluorobenzol)amide,
[227] 1-Butyl-3-(2-methylsulfanylethyl)-2-oxo-1,4,8-triazaspiro[4,5]decan-8-carboxylic acid (4-chloro-3-trifluoromethylbenzol)amide,
[228] 1-(4-Fluorobenzyl)-3-(2-methylsulfanylethyl)-2-oxo-1,4,8-triazaspiro[4,5]decan-8-carboxylic acid 3,4-dichlorobenzylamide,
[229] 1-(2-Cyanobenzyl)-3-(2-methylsulfanylethyl)-2-oxo-1,4,8-triazaspiro[4,5]decan-8-carboxylic acid 3,4-dichlorobenzylamide,
[230] 3-Benzyl-1-(2-fluorobenzyl)-2-oxo-1,4,8-triazaspiro[4,5]decan-8-carboxylic acid (2,5-difluorobenzol)amide,
[231] 3-(2-Methylsulfanylethyl)-1-naphthalin-2-ylmethyl-2-oxo-1,4,8-triazaspiro[4,5]decan-8-carboxylic acid (4-ethoxy-benzol)amide,
[232] Methyl 4-[8-(3,4-dichlorobenzylcarbamoyl)-3-isopropyl-2-oxo-1,4,8-triazaspiro[4,5]dec-1-ylmethyl]-benzoate,
[233] 3-Benzyl-1-(2-fluorobenzyl)-2-oxo-1,4,8-triazaspiro[4,5]decan-8-carboxylic acid 3,4-dichlorobenzylamide,

[234] 1-(2-Cyanobenzyl)-3-(2-methylsulfanylethyl)-2-oxo-1,4,8-triazaspiro[4,5]decan-8-carboxylic acid (3-acetyl-benzol)amide,

[235] Ethyl 4-{[3-benzyl-1-(2-fluorobenzyl)-2-oxo-1,4,8-triazaspiro[4,5]decan-8-carbonyl]-amino}-benzoate,

[236] 1-(3-Cyanobenzyl)-3-(2-methylsulfanylethyl)-2-oxo-1,4,8-triazaspiro[4,5]decan-8-carboxylic acid (3-methoxy-benzol)amide,

[237] 1-(4-Fluorobenzyl)-3-(2-methylsulfanylethyl)-2-oxo-1,4,8-triazaspiro[4,5]decan-8-carboxylic acid (4-trifluoromethoxy-benzol)amide,

[238] 3-Benzyl-1-(2-fluorobenzyl)-2-oxo-1,4,8-triazaspiro[4,5]decan-8-carboxylic acid cyclohexylamide,

[239] 1-(4-Fluorobenzyl)-3-(2-methylsulfanylethyl)-2-oxo-1,4,8-triazaspiro[4,5]decan-8-carboxylic acid phenethylamide,

[240] 3-(2-Methylsulfanylethyl)-1-naphthalin-2-ylmethyl-2-oxo-1,4,8-triazaspiro[4,5]decan-8-carboxylic acid (3-fluorobenzol)amide,

[241] Methyl 4-[8-(4-chloro-3-trifluoromethylbenzolcarbamoyl)-3-isopropyl-2-oxo-1,4,8-triazaspiro[4,5]dec-1-ylmethyl]-benzoate,

[242] 1-(3-Cyanobenzyl)-3-(2-methylsulfanylethyl)-2-oxo-1,4,8-triazaspiro[4,5]decan-8-carboxylic acid (2,5-dimethoxy-benzol)amide,

[243] 1-(4-Fluorobenzyl)-3-(2-methylsulfanylethyl)-2-oxo-1,4,8-triazaspiro[4,5]decan-8-carboxylic acid (4-ethoxy-benzol)amide,

[244] 1-(4-Fluorobenzyl)-3-(2-methylsulfanylethyl)-2-oxo-1,4,8-triazaspiro[4,5]decan-8-carboxylic acid (3-cyanobenzol)amide, and

[245] Ethyl[3-b-8-(3-fluorobenzolcarbamoyl)-2-oxo-1,4,8-triazaspiro[4,5]dec-1-yl]-acetate,

[246] 1,3-Dibenzyl-8-methansulfonyl-1,4,8-triazaspiro[4,5]decan-2-one,

[247] 8-Benzolsulfonyl-1,3-dibenzyl-1,4,8-triazaspiro[4,5]decan-2-one,

[248] 1,3-Dibenzyl-8-(4-chlorobenzolsulfonyl)-1,4,8-triazaspiro[4,5]decan-2-one,

[249] 1,3-Dibenzyl-8-(4-methoxy-benzolsulfonyl)-1,4,8-triazaspiro[4,5]decan-2-one,

[250] 1,3-Dibenzyl-2-oxo-1,4,8-triazaspiro[4,5]decan-8-carboxylic acid phenylamide,

[251] 1,3-Dibenzyl-2-oxo-1,4,8-triazaspiro[4,5]decan-8-carboxylic acid (4-methoxy-phenyl)amide,

[252] 1,3-Dibenzyl-2-oxo-1,4,8-triazaspiro[4,5]decan-8-thiocarboxylic acid phenylamide,

[253] 1,3-Dibenzyl-2-oxo-1,4,8-triazaspiro[4,5]decan-8-thiocarboxylic acid (2,4-difluorophenyl)amide, in each case optionally in the form of one of the pure stereoisomers thereof particularly enantiomers or diastereoisomers thereof, the racemates thereof or in the form of a mixture of stereoisomers, particularly the enantiomers and/or diastereoisomers thereof, in an arbitrary blending ratio, or in each case in the form of an appropriate salt, or in each case in the form of an appropriate solvate.

Another object of the present invention is the provision of a process for the production of substituted 1,4,8-triazaspiro[4,5]decan-2-one compounds of the invention of the above general formula I, according to which a protected piperidin-4-one of the general formula II,

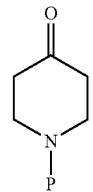

in which P stands for a protective group,
is converted, by reaction with at least one amino-acid amide compound of the general formula III,

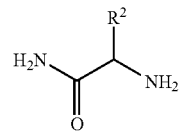

in which $R^2$ has the aforementioned meaning,
to at least one compound of the general formula IV,

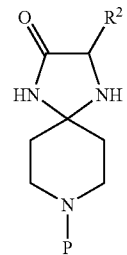

in which P and $R^2$ have the aforementioned meanings,
which is optionally purified and/or optionally isolated, and optionally converted
by reaction with at least one compound of the general formula $R^1$—$X^1$, in which $R^1$ has the aforementioned meaning and $X^1$ stands for a suitable leaving group, preferably for a halogen radical,
optionally in the presence of at least one base,
to at least one compound of the general formula V,

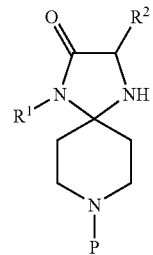

in which $R^1$, $R^2$ and P have the aforementioned meanings,
and this is optionally purified and/or optionally isolated, and optionally converted by splitting-off the protective group P
to at least one compound of the general formula VI,

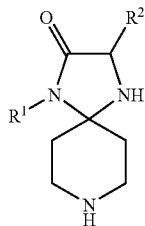

VI which is optionally purified and/or optionally isolated,
and at least one compound of the general formula IV, V or VI is converted,
by reaction with a sulfonyl compound of the general formula $R^4$—$SO_2$—$X^2$ optionally in the presence of at least one base, or by reaction with an isothiocyanate compound of the general formula $R^5$—NCS
or by reaction with an isocyanate compound of the general formula $R^6$—NCO in which the radicals $R^4$, $R^5$ and $R^6$ each have the aforementioned meanings and $X^2$ stands for a suitable leaving group, preferably for a halogen radical,
to at least one compound of the above general formula I in which each of the radicals $R^1$ to $R^3$ has the aforementioned meanings,
and this compound is optionally purified and/or optionally isolated.

The N-protected piperidin-4-one compounds of the general formula II are commercially available or can be prepared by conventional methods known to the person skilled in the art. Suitable protective groups are, for example, trifluoroacetamide, methoxycarbonyl, ethoxycarbonyl, tert-butoxycarbonyl, carbobenzoxy, allyloxycarbonyl, or 9-fluorenylmethoxycarbonyl.

The amino-acid amides of the general formula III, which can be used in the process of the invention also in the form of the appropriate salt thereof, are likewise commercially available or can be prepared by conventional methods known to the person skilled in the art. The respective amino-acid amides can be used in the process of the invention either in enantiomerically pure form, ie in (S) or (R) configuration, or in the form of a racemic mixture showing an (S,R) configuration.

The reaction of compounds of the general formula II with compounds of the general formula III to produce optionally 3-substituted N-protected 1,4,8-triazaspiro[4,5]decan-2-one compounds of the general formula IV, can be carried out under conventional conditions known to the person skilled in the art.

Preferably, the conversion is carried out in a suitable reaction medium, for example, in one or more dry organic solvents. Suitable solvents are, for example, alcohols, such as ethanol, or chlorinated hydrocarbons such as dichloromethane or chloroform. The temperature employed while combining and reacting the reactants can vary over a wide range.

The reaction of an optionally 3-substituted N-protected 1,4,8-triazaspiro[4,5]decan-2-one compound of the general formula IV, with a compound of the general formula $R^1$—$X^1$ to form compounds of the general formula V is preferably carried out in a reaction medium in the presence of at least one organic base and/or in the presence of at least one inorganic base under conventional conditions known to the person skilled in the art. The reaction may be advantageously carried out in a microwave oven.

Suitable inorganic bases are, for example, metal alcoholates such as sodium methanolate, sodium ethanolate, potassium tert-butylate, lithium or sodium bases such as lithium diisopropylamide, butyllithium, tert-butyllithium, sodium methoxide or metal hydrides such as potassium hydride, lithium hydride, sodium hydride. Suitable organic bases are, for example, diisopropylethylamine or triethylamine. Suitable reaction media are organic solvents such as tetrahydrofuran.

Elimination of the protective group (P) for the production of non-N-protected optionally 1-substituted and/or 3-substituted 1,4,8-triazaspiro[4,5]decan-2-one compounds of the general formula VI, can likewise be carried out under conventional conditions known to the person skilled in the art, which vary according to the protective group used. Mention may be made, for example, of elimination in the presence of an inorganic base, or acid, or Lewis acid, such as potassium carbonate, lithium hydroxide, potassium hydroxide, sulfuric acid, hydrobromic acid, hydrofluoric acid, hydrochloric acid, boron trifluoride etherate, boron trichloride, or of an organic acid such as trifluoroacetic acid, trifluoromethanesulfonic acid, acetic acid, elimination in the presence of an organic base, such as morpholine, triethylamine, diethylamine, diisopropylethylamine, pyridine, or hydrogenation.

The respective compounds of the general formula IV, V, or VI, particularly the respective compound of the general formula VI, can then be converted, by sulfonylation with a sulfonyl compound of the general formula $R^4$—$SO_2$—$X^2$, preferably in the presence of at least one organic base and/or at least one inorganic base such as sodium hydrogencarbonate, diisopropylethylamine, triethylamine, pyridine or diethylamine or with thiourea formation with isothiocyanates of the general formula $R^5$—NCS or with urea formation with isocyanates of the general formula $R^5$—NCO using conventional methods known to the person skilled in the art, to the respective substituted 1,4,8-triazaspiro[4,5]decan-2-one compound of the general formula I of the invention, including appropriate stereoisomers.

The conversion of compounds of the general formula IV, V, or VI, particularly compounds of the general formula VI, to a substituted 1,4,8-triazaspiro[4,5]decan-2-one compound of the general formula I of the invention is preferably carried out in a suitable reaction medium, for example, in one or more dry organic solvents. Suitable solvents are, for example, optionally chlorinated and optionally aromatic hydrocarbons such as toluene, dichloromethane, or chloroform. The temperature employed while combining and reacting the reactants can vary over a wide range.

The compounds of the general formulas $R^1$—$X^1$, $R^4$—$SO_2$—$X^2$, $R^5$—NCS, and $R^6$—NCO are each commercially available or can be prepared by conventional methods known to the person skilled in the art. $X^1$ and $X^2$ are conventional leaving groups known to the person skilled in the art and are preferably halogen radicals and more preferably chlorine radicals.

The intermediates and end products prepared by the aforementioned reactions can in each case be isolated and/or purified by conventional methods known to the person skilled in the art, if desired and/or necessary. Suitable purifying methods are, for example, extraction processes and chromatographic processes such as column chromatography or preparative chromatography.

The substituted 1,4,8-triazaspiro[4,5]decan-2-one compounds of the above general formula I of the invention and also, where applicable, the appropriate stereoisomers can be obtained by conventional methods known to the person skilled in the art in the form of appropriate salts, particularly in the form of appropriate physiologically acceptable salts, and the medicinal drug of the invention can comprise one or more salts of one or more of these compounds.

The respective salts of substituted 1,4,8-triazaspiro[4,5]decan-2-one compounds of the invention illustrated by the above general formula I can be obtained, for example, by reaction with one or more inorganic acids and/or one or more organic acids. Suitable acids can be preferably selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharinic acid, cyclohexanesulfamidic acid, aspartame, monomethylsebacic acid, 5-oxoproline, 1-hexanesulfonic acid, nicotinic acid, 2-aminobenzoic acid, 3-aminobenzoic acid, or 4-aminobenzoic acid, 2,4,6-trimethylbenzoic acid, alpha-lipoic acid, acetylglycine, hippuric acid, phosphoric acid, maleic acid, malonic acid, and aspartic acid.

The substituted 1,4,8-triazaspiro[4,5]decan-2-one compounds of the invention illustrated by the above general formula I and also, where applicable, appropriate stereoisomers and physiologically acceptable salts thereof may alternatively be obtained in the form of the solvates thereof, particularly in the form of the hydrates thereof by conventional methods known to the person skilled in the art.

If the substituted 1,4,8-triazaspiro[4,5]decan-2-one compounds of the invention illustrated by the above general formula I following production thereof are obtained in the form of a mixture of the stereoisomers thereof, preferably in the form of the racemates thereof or other mixtures of the various enantiomers and/or diastereoisomers thereof, they can be separated and optionally isolated by conventional methods known to the person skilled in the art. Mention may be made, for example, of chromatographic separation processes, particularly liquid chromatography processes under standard pressure or under elevated pressure, preferably MPLC and HPLC methods, and also methods involving fractional crystallization. This can particularly involve the separation of individual enantiomers, eg, diastereoisomeric salts formed by means of HPLC in the chiral phase or by means of crystallization with chiral acids, for example (+)-tartaric acid, (−)-tartaric acid, or (+)-10-camphorsulfonic acid.

It has now been found, surprisingly, that substituted 1,4,8-triazaspiro[4,5]decan-2-one compounds of the invention illustrated by the above general formula I are not only suitable for regulation, preferably inhibition, of 5-hydroxy tryptophane reuptake (serotonin reuptake) and/or for regulation, preferably inhibition, of noradrenalin reuptake but in addition also show a high affinity to batrachotoxin (BTX) receptors and/or cannabinoid receptors CB2 (CB2 receptors) and are therefore particularly suitable for use as pharmaceutically active substances in medicinal drugs for prophylaxis and/or treatment of disorders associated with these receptors or processes.

The 1,4,8-triazaspiro[4,5]decan-2-one compounds of the invention illustrated by the above general formula I and optionally the appropriate stereoisomers and also in each case the appropriate salt and solvate are toxicologically safe and are therefore suitable for use as pharmaceutically active substances in medicinal drugs.

Another object of the present invention is therefore the provision of a medicinal drug containing at least one substituted 1,4,8-triazaspiro[4,5]decan-2-one compound of the above general formula I, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary blending ratio, or in each case in the form of an appropriate salt, or in each case in the form of an appropriate solvate, and also containing optionally one or more pharmaceutically compatible adjuvants.

Preferably, the medicinal drug of the invention is suitable for regulation, particularly inhibition, of noradrenalin reuptake (noradrenalin-uptake), for regulation, particularly inhibition, of 5-hydroxy tryptophane reuptake (5-HT uptake), and/or for batrachotoxin (BTX) receptor regulation and/or for CB2 receptor regulation.

The medicinal drug of the invention is particularly suitable for prophylaxis and/or treatment of depression.

The medicinal drug of the invention is likewise preferentially suitable for prophylaxis and/or treatment of pain, preferably for treatment and prophylaxis of acute pain, chronic pain, neuropathic pain, and/or cluster headache.

The medicinal drug of the invention is more preferably suitable for the combined prophylaxis and/or treatment of depression and pain, preferably for the combined treatment of depression and pain selected from the group consisting of acute pain, chronic pain, neuropathic pain, and cluster headache, more preferably for the combined treatment of depression and chronic pain. By chronic pain is meant, for the purposes of the present invention, particularly such pain as is associated with cancerous diseases.

The medicinal drug of the invention is Furthermore, suitable for prophylaxis and/or treatment of abuse of alcohol and/or drugs and/or medicaments, for prophylaxis and/or treatment of addiction to alcohol and/or drugs and/or medicines, for prophylaxis and/or treatment of inflammations, for prophylaxis and/or treatment of lethargy, for prophylaxis and/or treatment of disturbances in food intake, preferably selected from the group consisting of bulimia, anorexia, obesity, and cachexia, for prophylaxis and/or treatment of catalepsy, for vigilance enhancement, for libido enhancement, for anxiolysis, for prophylaxis and/or treatment of neurodegenerative disorders, preferably one or more neurodegenerative disorders selected from the group consisting of Morbus Parkinson, Morbus Huntington, Morbus Alzheimer and multiple sclerosis, for prophylaxis and/or treatment of ischemia and/or for local anesthesia.

The medicinal drug of the invention is Furthermore, suitable for prophylaxis and/or treatment of one or more disorders selected from the group consisting of non-acute allergic disorders, preferably allergic dermatitis; asthma; rhinitis; conjunctivitis; disorders caused by 2-arachidone glycerin and/or appropriate ethers, such as haematol; sepsis; cancer, particularly leukemia and/or cerebral tumor; circulatory disorders; green cataract; inflammations, preferably immunologically mediated phlogogenic diseases, more preferably rheumatoid arthritis, Lupus erythematodes, psoriasis and thyroiditis; diabetes; blood poisoning; epilepsy; Tourettes syndrome; osteoporosis; Morbus Bechterew; gout; gouty arthritis; osteo-arthritis; disturbances of the circulation; ischemia, particularly renal ischemia, and/or for regulation of the immune system, preferably for suppression of the immune system.

The compounds of the invention are also suitable for reducing the spasticity in the multiple sclerosis model in mice (determined as described in Baker et al., Nature, 2000, 404, 84), for inhibiting the in-vivo growth of glioma tumors (determined as described in C. Sanchez et al., Cancer Res. 2001, 61, 5784), peripheral antinociception (determined as described in Malan et al., Pain 2001, 93, 239), and also for modulating the antitumor properties of ajulemic acid (determined as described in Recht et al., Bioch. Pharmacol. 2001, 62, 755). The relevant literature references are incorporated herein by reference and are to be regarded as part of the present disclosure.

Another object of the present invention is the use of at least one substituted 1,4,8-triazaspiro[4,5]decan-2-one compound of the above general formula I, optionally in the form of one of the pure stereoisomers thereof, particularly enantiomers or diastereoisomers thereof, the racemates thereof or in the form of a mixture of stereoisomers and particularly the enantiomers and/or diastereoisomers thereof in an arbitrary blending ratio, or in each case in the form of an appropriate salt, or in each case in the form of an appropriate solvate, and optionally at least one pharmaceutically compatible adjuvant for the production of a medicinal drug for regulation, particularly inhibition, of noradrenalin reuptake (noradrenalin-uptake), for regulation, particularly inhibition, of 5-hydroxy tryptophane reuptake (5-HT uptake) and/or for batrachotoxin (BTX) receptor regulation and/or for CB2 receptor regulation.

Preference is given, in particular, to the use of at least one substituted 1,4,8-triazaspiro[4,5]decan-2-one compound of the above general formula I, optionally in the form of one of the pure stereoisomers thereof, particularly enantiomers or diastereoisomers thereof, the racemates thereof or in the form of a mixture of stereoisomers and particularly of the enantiomers and/or diastereoisomers thereof in an arbitrary blending ratio, or in each case in the form of an appropriate salt, or in each case in the form of an appropriate solvate, and optionally at least one pharmaceutically compatible adjuvant for the production of a medicinal drug for prophylaxis and/or treatment of depression.

Preference is given to the use of at least one substituted 1,4,8-triazaspiro[4,5]decan-2-one compound of the above general formula I, optionally in the form of one of the pure stereoisomers thereof, particularly enantiomers or diastereoisomers thereof, the racemates thereof or in the form of a mixture of stereoisomers and particularly of the enantiomers and/or diastereoisomers thereof in an arbitrary blending ratio, or in each case in the form of an appropriate salt, or in each case in the form of an appropriate solvate, and optionally at least one pharmaceutically compatible adjuvant for the production of a medicinal drug for prophylaxis and/or treatment of pain, preferably for treatment and prophylaxis of acute pain, chronic pain, neuropathic pain, and/or cluster headache.

Particular preference is given to the use of at least one substituted 1,4,8-triazaspiro[4,5]decan-2-one compound of the above general formula I, optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary blending ratio, or in each case in the form of an appropriate salt, or in each case in the form of an appropriate solvate, and optionally at least one pharmaceutically compatible adjuvant for the production of a medicinal drug for the combined prophylaxis and/or treatment of depression and pain, preferably for the combined treatment of depression and pain selected from the group consisting of acute pain, chronic pain, neuropathic pain, and cluster headache, more preferably for the combined treatment of depression and chronic pain.

Furthermore, preference is given to the use of at least one substituted 1,4,8-triazaspiro[4,5]decan-2-one compound of the above general formula I, optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary blending ratio, or in each case in the form of an appropriate salt, or in each case in the form of an appropriate solvate, and optionally at least one pharmaceutically compatible adjuvant for the production of a medicinal drug for prophylaxis and/or treatment of abuse of alcohol and/or drugs and/or medicaments, for prophylaxis and/or treatment of addiction to alcohol and/or drugs and/or medicines, for prophylaxis and/or treatment of inflammations, for prophylaxis and/or treatment of lethargy, for prophylaxis and/or treatment of disturbances in food intake, preferably selected from the group consisting of bulimia, anorexia, obesity, and cachexia, for prophylaxis and/or treatment of catalepsy, for vigilance enhancement, for libido enhancement, for anxiolysis, for prophylaxis and/or treatment of neurodegenerative disorders, preferably one or more neurodegenerative disorders selected from the group consisting of Morbus Parkinson, Morbus Huntington, Morbus Alzheimer, and multiple sclerosis, for prophylaxis, and/or treatment of ischemia and/or for local anesthesia.

Furthermore, preference is given to the use of at least one substituted 1,4,8-triazaspiro[4,5]decan-2-one compound of the above general formula I, optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary blending ratio, or in each case in the form of an appropriate salt, or in each case in the form of an appropriate solvate, and optionally at least one pharmaceutically compatible adjuvant, for the production of a medicinal drug for the prophylaxis and/or treatment of one or more disorders selected from the group consisting of non-acute allergic disorders, preferably allergic dermatitis; asthma; rhinitis; conjunctivitis; disorders caused by 2-arachidone glycerin and/or appropriate ethers, such as haematol; sepsis; cancer, particularly leukemia and/or cerebral tumor; circulatory disorders; green cataract; inflammations, preferably immunologically mediated phlogogenic diseases, more preferably rheumatoid arthritis, Lupus erythematodes, psoriasis and thyroiditis; diabetes; blood poisoning; epilepsy; Tourettes syndrome; osteoporosis; Morbus Bechterew; gout; gouty arthritis; osteo-arthritis; disturbance of circulation; ischemia, preferably renal ischemia, and/or for regulation of the immune system, preferably for suppression of the immune system.

The medicinal drug of the invention is suitable for administration to adults and children including infants and babies.

The medicinal drug of the invention can exist as liquid, semisolid or solid pharmaceutical dosage forms, for example, in the form of injection fluids, drops, juices, syrups, sprays, suspensions, tablets, patches, capsules, plasters, suppositories, ointments, creams, lotions, gels, emulsions, aerosols or in multiparticular form, for example, in the form of pellets or granules, optionally compressed to tablets, filled into capsules or suspended in a liquid and can be administered as such.

In addition to the said one or more substituted 1,4,8-triazaspiro[4,5]decan-2-one compounds of the above general formula I used in the medicinal drug of the invention optionally in the form of one of the pure stereoisomers thereof, particularly enantiomers or diastereoisomers thereof or the racemates thereof or in the form of mixtures of the stereoisomers, particularly the enantiomers or diastereoisomers thereof, in an arbitrary blending ratio, or optionally in the form of an appropriate salt or in each case in the form of an appropriate solvate, the medicinal drug of the invention usually contains further physiologically acceptable pharmaceutical adjuvants, which can be selected preferably from the group consisting of support materials, fillers, solvents, diluents, surfactant, dyes, preservatives, blasting agents, lubricants, slip agents, flavors, and binding agents.

The selection of the physiologically acceptable adjuvants and the amounts thereof to be used depends on whether the medicinal drug is to be administered orally, subcutaneously, parenterally, intravenously, intraperitoneally, intradermally, intramuscularly, intranasally, buccally, rectally, or locally, eg, to infections of the skin, the mucous membranes, or the eyes. Preparations preferably suitable for oral administration are in the form of tablets, dragees, capsules, granules, pellets, drops, juices, and syrups, and for parenteral, topical, and inhalative administration the suitable preparations are solutions, suspensions, readily reconstructable dry preparations, and also sprays.

The substituted 1,4,8-triazaspiro[4,5]decan-2-one compounds used in the medicinal drug of the invention in a depot in dissolved form or in a patch, optionally with the addition of skin penetration enhancing agents, are suitable percutane administration forms. Orally or percutanely applicable formulations can afford delayed release of the respective substituted 1,4,8-triazaspiro[4,5]decan-2-one compounds.

The production the medicinal drug of the invention is carried out using conventional well-known means, devices, methods, and processes known in the prior art, as described, for example, in "Remington's Pharmaceutical Sciences", Editor A. R. Gennaro, 17th Edition, Mack Publishing Company, Easton, Pa., 1985, particularly in Section 8, Chapter from 76 to 93. The relevant description is included herein by reference and is to be regarded as part of the disclosure.

The amount of the respective substituted 1,4,8-triazaspiro[4,5]decan-2-one compound to be administered to the patient can vary and is, for example, dependent on the weight or age of the patient and also on the method of administration, the indication and the severity of the disorder. Usually from 0.005 to 500 mg/kg, preferably from 0.05 to 50 mg/kg of body weight of the patient of at least one substituted 1,4,8-triazaspiro[4,5]decan-2-one compound of the invention are administered.

Pharmacological Methods:

I. Method of Determining the Inhibition of Noradrenalin Uptake or 5-HT Uptake:

For in vitro studies, synaptosomes of rat brain areas are freshly isolated, as described in the article "The isolation of nerve endings from brain" by E. G. Gray and V. P. Whittaker, J. Anatomy 96, pages 79-88, 1962. The relevant literature reference is enclosed herein by reference and is to be regarded as part of the disclosure.

The tissue (hypothalamus for the determination of the noradrenalin uptake inhibition and marrow and pons for determination of the 5-HT uptake inhibition) is homogenized in ice-cooled 0.32 M sucrose (100 mg of tissue/1 mL) in a glass homogenizer with teflon pestle by carrying out five full up and down strokes at 840 rpm.

The homogenate is centrifuged at 4° C. for 10 minutes at 1000 g. Following subsequent centrifugation at 17,000 g for 55 minutes, the synaptosomes (P2 fraction) are obtained, which are then resuspended in 0.32 M glucose (0.5 mL/100 mg of the original weight).

The respective uptake was measured in a 96 well microtiter plate. The volume was 250 µL and the incubation was carried out at room temperature (ca 20 to 25° C.) under a blanket of oxygen.

The incubation period was 7.5 minutes for [$^3$H]-NA and 5 minutes for [$^3$H]-5-HT. The 96 samples were then filtered through a Unifilter GF/B® microtiter plate (Packard) and washed with 200 mL of incubated buffer with the aid of a "Brabdel Cell Harvester MPXRI96T". The Unifilter GF/B plate was dried at 55° C. over a period of 1 h. The plate was then sealed with a back seal® (Packard) and there were then added 35 µL of scintillant fluid per well (Ultima Gold, Packard). Following sealing with a top seal® (Packard) and following adjustment of the equilibrium (approximately over a period of 5 h), the radioactivity is determined in a Trilux 1450 Microbeta® (Wallac, Freiburg, Germany).

The amount of protein used in the above determination corresponded to the values known from the literature, such as is described in "Protein measurement with the folin phenol reagent", Lowry et al., J. Biol. Chem., 193, 265-275, 1951.

A detailed description of the method is disclosed in the literature, for example, in M. Ch. Frink, H.-H. Hennis, W. Engelberger, M. Haurand, and B. Wilffert ((1996) Arzneim. forsch./Drug Res. 46 (III), 11, 1029-1036.

The relevant literature references are incorporated herein by reference and are to be regarded as part of the present disclosure.

The following characteristic data are found for the NA transporter and for the 5-HT transporter respectively:

NA uptake: Km=0.32±0.11 µM

5-HT uptake: Km=0.084±0.011 µM

II. Method of Determining the Affinity to the Batrachotoxin (BTX) Binding Site of the Sodium Channel:

Binding site 2 of the sodium channel is the so-called batrachotoxin (BTX) binding site. As a ligand, [$^3$H]-batrachotoxinin A20 α-benzoate (10 nM in the batch) is employed. The ion channel particles (synaptosomes) are enriched from rat cerebrocortex, as described in the publication by Gray and Whittaker, 1962, J. Anat. 76, 79-88. The relevant description is included herein by reference and is to be regarded as part of the present disclosure. The nonspecific binding is defined as the radioactivity which is measured in the presence of veratridine ($3 \times 10^{-4}$ M in the batch).

The assay conditions are carried out according to the publication by Pauwels, Leysen and Laduron, as described in Eur. J. Pharmacol. 124, 291-298. The relevant description is incorporated herein by reference and is to be regarded as part of the present disclosure.

Deviating from this procedure, the total batch is reduced to 250 µL so that the assay can be carried out in 96-well microtiter plates. The incubation time in these microtiter plates is two hours at room temperature (about 20 to 25° C.).

The following characteristics were determined for the $K_D$ value of the binding site:

$K_D$: 24.63±1.56 nM.

III. Determination of the Affinity to the Cannabinoid Receptor CB2 (CB2 Receptor):

For the purpose of determining the affinity of the compounds of the invention for the cannabinoid receptor use is made of membranes of human recombinant HEK 293EBNA cells which have been stably transferred with the human CB2 receptor. The radioligand used was tritium-labeled 5-(1,1-dimethylheptyl)-2-(5-hydroxypropyl)cyclohexyl)-1-alpha, 2-beta,5-alpha)-phenol ($[^3]H$—CP 55,940 with 103.4 of Ci/mmol, 1 m Ci/mL). Determination was carried out in a test buffer comprising 50 mM of Tris-HCl, 2.5 mm of EDTA, 5 mm of $MgCl_2$ and 1.0 mg/mL of fatty acid-free BSA. The test substances were in each case dissolved in DMSO.

The affinity of the compounds of the invention to the CB2 receptor is determined by their ability to displace $[^3]H$—CP from 55,940 of CB2 receptors in membranes of HEK 293 EBNA cells. For this purpose 8 μg of membranes (20 mL of a solution of membranes in a concentration of 400 g/ml) are incubated in wells of a microtiter plate with a 0.33 nM of solution of [3]H-CP 55,949 (120 of Ci/mmol) in a total volume of test buffer of 200 μL for 90 minutes at 30° C.

Subsequently, either the test substances or WIN 55,212-2 for determination the non-specific binding are placed, dissolved in each case in dimethyl sulphoxide, in the wells so that in each case a concentration of the relevant substances of 10 μM is obtained.

Incubation is continued for a further 40 minutes at 30° C. dc. The binding reaction was terminated by rapid filtration through GF/C filter paper which had been treated with 0.05% of PEI, using a 96-well Brandel cell harvester. The filters are washed nine times with 0.5 mL of ice-cold washing buffer (50 nM of Tris-HCl, 5 mM of $MgCl_2$, 2.5 mm of EDTA, 2% of BSA, pH 7.4), air-dried, placed in scintillation liquid, and the radioactivity is determined with the aid of a scintillation counter.

The percentage displacement of the radio-active ligand $[^3]H$—CP 55,940 from its binding to the CB2 receptor is indicated as percentage inhibition of the specific binding. In order to determine $K_i$ the $IC_{50}$ inhibition concentrations are calculated based on of the percentage displacement achieved by the compounds of the general formula I to be tested at various concentrations causing a 50 percent displacement of the radioactive ligands. Correction carried out using the Cheng Prusoff equation according to Biochm. Pharmacol. 1973, 22, 3099 gave $K_i$ values of the test substances.

The invention is explained below with reference to examples. These examples are exemplary only and the scope of the invention is not restricted thereto.

EXAMPLES

The yields of the compounds prepared are not optimized. All temperatures are uncorrected.

The statement "EE" means diethyl ether, "EtOH" means ethanol, and "THF" means tetrahydrofuran. The statement "equivalent" means amount of substance equivalent, "RT" means room temperature, "min" means minutes, "h" means hours, "d" means days, "vol. %" means percent by volume, and "M" stands for concentration in mol/l.

The chemicals and solvents employed were acquired commercially from the conventional suppliers (for example Acros, Acocado, Aldrich, Bachem, Fluka, Lancaster, Maybridge, Merck, Sigma, TCi etc) or synthesized according to customary methods known to the person skilled in the art.

As a stationary phase for column chromatography, silica gel 60 (0.040-0.063 mm) supplied by E. Merck, Darmstadt, was employed.

The thin-layer chromatographic investigations were carried out using HPTLC ready-to-use plates, silica gel 60 F 254, supplied by E. Merck, Darmstadt.

The mixing ratios of eluents for chromatographic investigations are always indicated in volume/volume.

Analysis was carried out by means of HPLC-MS or/and NMR spectroscopy.

General procedure for the preparation of substituted 1,4,8-triazaspiro-[4,5]decan-2-one compounds according to the invention Stage 1:

General Procedure for the Preparation of Optionally 3-substituted tert-butyl 2-oxo-1,4,8-triazaspiro-[4,5]decane-8-carboxylate compounds One equivalent of N-tert-butyloxycarbonylpiperidone and one equivalent of triethylamine were added to the solution of one equivalent of the respective amino acid amide (i.e. of the respective compound of the general formula III), optionally in the form of an appropriate salt, in a dry solvent such as, for example, ethanol and the reaction mixture thus obtained was heated under reflux for 1 to 5 h. The solvent was removed by distillation and the optionally 3-substituted tert-butyl 2-oxo-1,4,8-triazaspiro[4,5]decane-8-carboxylate compound thus obtained (compound of the general formula IV, in which P represents a tert-butyl carboxylate (BOC) protective group) was usually employed in the following reactions without further workup.

If necessary, the respective optionally 3-substituted tert-butyl 3-oxo-1,4,8-triazaspiro[4,5]decane-8-carboxylate compound was purified as follows:

After addition of water and a suitable organic solvent such as, for example, $CH_2Cl_2$, the organic phase was separated off, and the aqueous phase was extracted with $CH_2Cl_2$. The combined organic phases were dried over $Na_2SO_4$. After filtration, the solvent was removed by distillation. The corresponding optionally 3-substituted tert-butyl 2-oxo-1,4,8-triazaspiro-[4,5]decane-8-carboxylate compound was obtained.

Stage 2:

General procedure for the preparation of substituted 1-substituted and optionally 3-substituted tert-butyl 2-oxo-1,4,8-triazaspiro-[4,5]decane-8-carboxylate compounds The solution of 1 equivalent of the respective optionally substituted tert-butyl 2-oxo-1,4,8-triazaspiro[4,5]decane-8-carboxylate compound according to Stage 1 in a suitable organic solvent such as, for example, THF was added dropwise to the suspension or solution of 1 to 2 equivalents of a suitable base such as, for example, NaH in a suitable solvent such as, for example, THF at a temperature of from 0° C. to RT.

Alternatively, a suspension or solution of 1 to 2 equivalents of a suitable base such as, for example, NaH in a suitable solvent such as, for example, THF was added dropwise to a solution of the respective optionally substituted tert-butyl 2-oxo-1,4,8-triazaspiro[4,5]decane-8-carboxylate compound according to Stage 1 in a suitable organic solvent such as, for example, THF at a temperature of from 0° C. to RT.

After stirring for 1 h at 0° C., 1 to 1.3 equivalents of the respective chloride compound (i.e. a compound of the general formula $R^1$—$X^1$, in which $X^1$ represents a Cl radical) were added dropwise, the reaction mixture thus obtained was allowed to warm to RT and subsequently heated for 2 hours to 3 days under reflux. If necessary, a further 0.5 to 1 equivalent of the respective chloride compound was added and the reaction mixture was heated under reflux for a further 10 to 25 h.

Subsequently, the reaction mixture was treated with saturated aqueous NH$_4$Cl solution, the organic phase was separated off, and the aqueous phase was extracted with EA. The combined organic phase was dried over Na$_2$SO$_4$, filtered, and the solvent was removed by distillation. Workup was carried out by means of column chromatography to give the respective 1-substituted and optionally 3-substituted tert-butyl 2-oxo-1,4,8-triazaspiro-[4,5] decane-8-carboxylate compound (i.e. a compound of the general formula V, in which P represents a BOC protective group).

Stage 3:

General procedure for the preparation of optionally 1-substituted and/or 3-substituted 2-oxo-1,4,8-triazaspiro[4,5]decan-2-one compounds 10 to 25 equivalents of trifluoroacetic acid were added dropwise to a solution of 1 equivalent of the respective optionally 1-substituted and/or 3-substituted tert-butyl 2-oxo-1,4,8-triazaspiro[4,5]decane-8-carboxylate compound in CH$_2$Cl$_2$ at 0° C. and the mixture was stirred at this temperature for 15 min. After warming to RT, the reaction solution was stirred for a further 2.5 h. Subsequently, the reaction solution was adjusted to a pH of 7 to 8 with saturated aqueous NaHCO$_3$ solution, the organic phase was separated off, and the aqueous phase was extracted with CH$_2$Cl$_2$ (2×30 ml). The combined organic phase was dried over Na$_2$SO$_4$, filtered, and the solvent was removed by distillation. Workup was carried out by means of column chromatography to give the respective optionally 1-substituted and/or 3-substituted 2-oxo-1,4,8-triazaspiro[4,5]decan-2-one compound unprotected on the N(8)-nitrogen (i.e. a compound of the general formula VI).

Stage 4a:

General procedure for the preparation of sulfonylated 2-oxo-1,4,8-triazaspiro[4,5]decan-2-one compounds according to the invention (compounds of the general formula I, in which R$^3$ represents an —S(=O)$_2$—R$^4$ group)

1 to 5 equivalents of the respective sulfonyl chloride (i.e. a compound of the general formula R4—SO2—X2, in which X2 represents a Cl radical), undiluted or dissolved in an organic solvent such as, for example, CH2Cl2, were added to a solution of an optionally 1-substituted and/or 3-substituted 2-oxo-1,4,8-triazaspiro[4,5]decan-2-one compound in a dry organic solvent such as, for example, CH2Cl2 and in the presence of an organic or inorganic base such as, for example, sodium hydrogencarbonate, diisopropylethylamine, triethylamine, or diethylamine at a temperature of from 0° C. to RT and stirred for from 1 to 24 h at a temperature of 0° C., RT, or under reflux. The reaction solution thus obtained was rendered alkaline by addition of an inorganic base in aqueous solution, for example of a saturated aqueous KOH solution, NaHCO3 solution or sodium hydroxide solution, the organic phase was separated off, and the aqueous phase was extracted a number of times with a suitable solvent such as, for example, CH2Cl2. The combined organic phases were dried using a drying agent such as, for example, Na2SO4. After removal of the solvent by distillation, further purification was carried out by means of column chromatography or preparative chromatography to give the respective sulfonylated 2-oxo-1,4,8-triazaspiro[4,5]decan-2-one compound.

Stage 4b:

General procedure for the preparation of 2-oxo-1,4,8-triazaspiro[4,5]decan-2-one compounds of the general formula I according to the invention, in which R$^3$ represents a —C(=S)—NH—R$^5$ group or a —C(=O)—NH—R$^6$ group 1 to 5 equivalents of the respective isothiocyanate compound of the general formula R$^5$—NCS or the respective isocyanate compound of the general formula R$^6$—NCO, undiluted or dissolved in an organic solvent such as, for example, CH$_2$Cl$_2$ or toluene, were added to a solution of an appropriate 2-oxo-1,4,8-triazaspiro[4,5]decan-2-one compound optionally 1-substituted and/or 3-substituted in a dry organic solvent such as, for example, CH$_2$Cl$_2$ or toluene at a temperature between 0° C. and RT and stirred for from 1 to 24 h at a temperature of 0° C., RT, or under reflux. The reaction solution thus obtained was treated with saturated aqueous NaCl solution, the organic phase was separated off, and the aqueous phase was extracted a number of times with a suitable solvent such as, for example, CH$_2$Cl$_2$ or the reaction solution was rendered alkaline by the addition, for example, of a saturated aqueous NaHCO$_3$ solution, the organic phase was separated off, and the aqueous phase was extracted a number of times with a suitable solvent such as, for example, CH$_2$Cl$_2$. The combined organic phases were dried using a drying agent such as, for example, Na$_2$SO$_4$. After removal of the solvent by distillation, further purification was carried out by means of column chromatography or preparative chromatography to give the respective 2-oxo-1,4,8-triazaspiro[4,5]decan-2-one compound of the general formula I, in which R$^3$ represents a —C(=S)—NH—R$^5$ group or a —C(=O)—NH—R$^6$ group.

The general synthesis procedures of Stages 1 to 3 described above are further illustrated below with reference to detailed examples:

Stage 1:

Preparation of tert-butyl 3-benzyl-2-oxo-1,4,8-triazaspiro[4,5]decane-8-carboxylate N-tert-Butyloxycarbonylpiperidone (6.0 g, 29.8 mmol) was added to a solution of phenylalaninamide (4.9 g, 29.8 mmol) in dry EtOH (20 ml) and the mixture was heated under reflux for 2.5 h. The solvent was removed by distillation, and the tert-butyl 3-benzyl-2-oxo-1,4,8-triazaspiro[4,5]decane-8-carboxylate (10.8 g) was used in the following reaction without further workup.

Stage 2:

Preparation of tert-butyl 1,3-dibenzyl-2-oxo-1,4,8-triazaspiro[4,5]decane-8-carboxylate NaH (1.26 g, 52.5 mmol) was added to a solution of tert-butyl 3-benzyl-2-oxo-1,4,8-triazaspiro[4,5]decane-8-carboxylate (12.1 g, 35 mmol) in THF (250 ml) at RT. After stirring for 1 h at 0° C., benzyl chloride (4.9 g, 38.5 mmol) was added dropwise, and the mixture was allowed to warm to RT and heated under reflux for 60 h. Subsequently, benzyl chloride (2.4 g, 19 mmol) was again added, and the mixture was heated under reflux for a further 16 h. The reaction mixture was treated with saturated aqueous NH$_4$Cl solution (20 ml) and extracted with EA (3×50 ml). The combined organic phase was dried over $Na_2SO_4$ and filtered and the solvent was removed by distillation. Workup was carried out by means of column chromatography to give tert-butyl 1,3-dibenzyl-2-oxo-1,4,8-triazaspiro[4,5]decane-8-carboxylate in a yield of 13.5 g (88% of theory).

Stage 3:

Preparation of 1,3-dibenzyl-1,4,8-triazaspiro[4,5]decan-2-one

Trifluoroacetic acid (68.5 g, 601 mmol) was added dropwise at 0° C. to a solution of tert-butyl 1,3-dibenzyl-2-oxo-1,4,8-triazaspiro[4,5]decane-8-carboxylate (13.5 g, 31.0 mmol) in CH2Cl2 (93 ml), and the mixture was stirred at this temperature for 15 min. After warming to RT, the reaction solution was stirred for a further 2.5 h. Subsequently, the reaction solution was adjusted to pH 7 to 8 using NaHCO3 solution, the organic phase was separated off, and the aqueous phase was extracted with CH2Cl2 (2×30 ml). The combined organic phase was dried over $Na_2SO_4$, filtered and the solvent was removed by distillation. Workup was carried out by means of column chromatography to give 1,3-dibenzyl-1,4,8-triazaspiro[4,5]decan-2-one in a yield of 7.8 g (75% of theory).

Example 246

Preparation of 1,3-dibenzyl-8-methanesulfonyl-1,4,8-triazaspiro[4,5]decan-2-one Triethylamine (0.15 ml, 1.78 mmol) and subsequently methanesulfonyl chloride (0.14 ml, 1.78 mmol) were added to a solution of 1,3-dibenzyl-1,4,8-triazaspiro-[4,5]decan-2-one (300 mg, 0.89 mmol) in $CH_2Cl_2$ (8.1 ml) with stirring using nitrogen as an inert gas at RT. The reaction mixture was stirred overnight. The organic phase was rendered alkaline using aqueous sodium carbonate solution (20 ml) and the aqueous phase was extracted with $CH_2Cl_2$ (15 ml). The combined organic phases were dried over $Na_2SO_4$. After filtration, removal of the solvent, and column chromatography, the desired product 1,3-dibenzyl-8-methanesulfonyl-1,4,8-triazaspiro[4,5]decan-2-one was obtained in a yield of 287 mg (77% of theory).

Example 247

Preparation of 8-benzenesulfonyl-1,3-dibenzyl-1,4,8-triazaspiro[4,5]decan-2-one Triethylamine (0.12 ml, 0.89 mmol) and subsequently benzenesulfonyl chloride (0.19 ml, 0.26 mmol) were added to a solution of 1,3-dibenzyl-1,4,8-triazaspiro-[4,5]decan-2-one (250 mg, 0.75 mmol) in $CH_2Cl_2$ (6.7 ml) with stirring under a blanket of nitrogen at RT. The reaction mixture was stirred overnight. The organic phase was rendered alkaline using saturated aqueous sodium carbonate solution (20 ml), and the aqueous phase was extracted with $CH_2Cl_2$ (15 ml). The combined organic phases were dried over $Na_2SO_4$. After filtration, removal of the solvent, and column chromatography, the desired product 8-benzenesulfonyl-1,3-dibenzyl-1,4,8-triazaspiro[4,5]decan-2-one was obtained in a yield of 259 mg (73% of theory).

Example 248

Preparation of 1,3-dibenzyl-8-(4-chloro-benzenesulfonyl)-1,4,8-triazaspiro-[4,5]decan-2-one Triethylamine (0.12 ml, 0.89 mmol) and subsequently 4-chlorobenzenesulfonyl chloride (314 mg, 1.49 mmol) were added to a solution of 1,3-dibenzyl-1,4,8-triaza-spiro[4,5]decan-2-one (249 mg, 0.75 mmol) in $CH_2Cl_2$ (6.7 ml) with stirring under a blanket of nitrogen at RT. The reaction mixture was stirred overnight. The organic phase was rendered alkaline using saturated aqueous sodium carbonate solution (20 ml) and the aqueous phase was extracted with $CH_2Cl_2$ (15 ml). The combined organic phases were dried over $Na_2SO_4$. After filtration, removal of the solvent and column chromatography, the desired product 1,3-dibenzyl-8-(4-chlorobenzene-sulfonyl)-1,4,8-triazaspiro[4,5]decan-2-one was obtained in a yield of 382 mg (100% of theory).

Example 249

Preparation of 1,3-dibenzyl-8-(4-methoxy-benzenesulfonyl)-1,4,8-triazaspiro-[4,5]decan-2-one Triethylamine (0.12 ml, 0.89 mmol) and subsequently 4-methoxybenzenesulfonyl chloride (308 mg, 1.49 mmol) were added to a solution of 1,3-dibenzyl-1,4,8-triaza-spiro[4,5]decan-2-one (249 mg, 0.75 mmol) in $CH_2Cl_2$ (6.7 ml) with stirring under a blanket of nitrogen at RT. The reaction mixture was stirred overnight. The organic phase was rendered alkaline using saturated aqueous sodium carbonate solution (20 ml), and the aqueous phase was extracted with $CH_2Cl_2$ (15 ml). The combined organic phases were dried over $Na_2SO_4$. After filtration, removal of the solvent, and column chromatography, the desired product 1,3-dibenzyl-8-(4-methoxy-benzenesulfonyl)-1,4,8-triazaspiro[4,5]decan-2-one was obtained in a yield of 301 mg (79% of theory).

Example 250

Preparation of 1,3-dibenzyl-2-oxo-1,4,8-triazaspiro[4,5]decane-8-carboxylic acid phenylamide Phenyl isocyanate (0.16 ml, 1.49 mmol) was added to a solution of 1,3-dibenzyl-1,4,8-triazaspiro[4,5]decan-2-one (502 mg, 1.49 mmol) in toluene (12.4 ml) with stirring under a blanket of nitrogen at RT. The reaction mixture was stirred overnight. After removal of the solvent, the desired product 1,3-dibenzyl-2-oxo-1,4,8-triaza-spiro[4,5]decane-8-carboxylic acid phenylamide was obtained by means of preparative HPLC.

Example 251

Preparation of 1,3-dibenzyl-2-oxo-1,4,8-triazaspiro[4,5]decane-8-carboxylic acid (4-methoxyphenyl)amide 4-Methoxyphenyl isocyanate (221 mg, 1.49 mmol) was added to a solution of 1,3-di-benzyl-1,4,8-triazaspiro[4,5]decan-2-one (499 mg, 1.49 mmol) in toluene (12.3 ml) with stirring under a blanket of nitrogen at RT. The reaction mixture was stirred at 115° C. for 4 h. After removal of the solvent, the desired product 11,3-dibenzyl-2-oxo-1,4,8-triazaspiro[4,5]decane-8-carboxylic acid (4-methoxyphenyl)amide was obtained by means of preparative HPLC.

Example 252

Preparation of 1,3-dibenzyl-2-oxo-1,4,8-triazaspiro[4,5]decane-8-thiocarboxylic acid phenylamide Phenyl isothiocyanate (203 mg, 1.50 mmol) was added to a solution of 1,3-dibenzyl-1,4,8-triazaspiro[4,5]decan-2-one (505 mg, 1.50 mmol) in toluene (14.3 ml) with stirring under a blanket of nitrogen at RT and the reaction mixture was stirred at 50° C. for 8 h. After removal of the solvent, the desired product 1,3-dibenzyl-2-oxo-1,4,8-triazaspiro[4,5]decane-8-thiocarboxylic acid phenylamide was obtained by means of preparative HPLC.

Example 253

Preparation of 1,3-dibenzyl-2-oxo-1,4,8-triazaspiro[4,5]decane-8-thiocarboxylic acid (2,4-difluorophenyl)amide 2,4-Difluorophenyl isothiocyanate (256 mg, 1.50 mmol) was added to a solution of 1,3-dibenzyl-1,4,8-triazaspiro[4,5]decan-2-one (503 mg, 1.50 mmol) in toluene (14.3 ml) with stirring under a blanket of nitrogen at RT and the reaction mixture was stirred at 50° C. for 8 h. After removal of the solvent, the desired product 1,3-dibenzyl-2-oxo-1,4,8-triazaspiro[4,5]decane-8-thiocarboxylic acid (2,4-difluorophenyl)amide was obtained by means of preparative HPLC.

Stage 1:

Preparation of tert-butyl 3-(2-methylsulfanylethyl)-2-oxo-1,4,8-triazaspiro-[4,5]decane-8-carboxylate N-tert-Butyloxycarbonylpiperidone (5.9 g, 29.8 mmol) and triethylamine (3.02 g, 29.8 mmol) were added to a solution of methioninamide hydrochloride (5.5 g, 29.8 mmol) in dry EtOH (66 ml), and the mixture was heated under reflux for 2.5 h. After addition of water (50 ml) and $CH_2Cl_2$ (200 ml), the organic phase was separated off, and the aqueous phase was extracted with $CH_2Cl_2$ (3×20 ml). The combined organic phases were dried over $Na_2SO_4$. After filtration, the solvent was removed by distillation. tert-Butyl 3-(2-methylsulfanylethyl)-2-oxo-1,4,8-triazaspiro[4,5]decane-8-carboxylate was obtained in a yield of 8.0 g (82% of theory).

Stage 2:

Preparation of tert-butyl 1-benzyl-3-(2-methylsulfanylethyl)-2-oxo-1,4,8-triaza-spiro[4,5]decane-8-carboxylate A solution of tert-butyl 3-(2-methylsulfanylethyl)-2-oxo-1,4,8-triazaspiro[4,5]decane-8-carboxylate (4.4 g, 13.4 mmol) in THF (72 ml) was added dropwise to a suspension of NaH (385 mg, 16,0 mmol) in THF (60 ml) at 0° C. After stirring for 1 h at 0° C., benzyl chloride (2.0 g, 16.0 mmol) was added dropwise, and the mixture was allowed to warm to RT and was then heated for 68 h under reflux. The reaction mixture was treated with saturated aqueous $NH_4Cl$ solution (20 ml), the organic phase was separated off, and the aqueous phase was extracted with EA (3×50 ml). The combined organic phase was dried over $Na_2SO_4$, filtered, and the solvent was removed by distillation. Workup was carried out by means of column chromatography to give 1-tert-butyl benzyl-3-(2-methylsulfanylethyl)-2-oxo-1,4,8-triazaspiro[4,5]decane-8-carboxylate in a yield of 1.6 g (30% of theory).

Stage 3:

Preparation of 1-benzyl-3-(2-methylsulfanylethyl)-1,4,8-triazaspiro[4,5]decan-2-one Trifluoroacetic acid (7.8 g, 68.0 mmol) was added dropwise to a solution of tert 1-butyl benzyl-3-(2-methylsulfanylethyl)-2-oxo-1,4,8-triazaspiro[4,5]decane-8-carboxylate (1.5 g, 3.5 mmol) in $CH_2Cl_2$ (10 ml) at 0° C. and the mixture was stirred for 15 min at this temperature. After warming to RT, the reaction solution was stirred for a further 2.5 h. Subsequently, the reaction solution was adjusted to pH 7 to 8 using saturated aqueous $NaHCO_3$ solution, the organic phase was separated off, and the aqueous phase was extracted with $CH_2Cl_2$ (2×10 ml). The combined organic phase was dried over $Na_2SO_4$, filtered and the solvent was removed by distillation. Workup was carried out by means of column chromatography to give 1-benzyl-3-(2-methylsulfanyl-ethyl)-1,4,8-triazaspiro[4,5]decan-2-one in a yield of 655 mg (58% of theory).

Exemplary Compounds

[1] 3-Isopropyl-8-(4-nitrobenzolsulfonyl)-1,4,8-triazaspiro[4,5]decan-2-one,

[2] 8-(2-Chlorobenzolsulfonyl)-3-isobutyl-1,4,8-triazaspiro[4,5]decan-2-one,

[3] 3-Benzyl-8-[2-(2,2,2-trifluoroacetyl)-1,2,3,4-tetrahydroisoquinolin-7-sulfonyl]-1,4,8-triazaspiro[4, 5] decan-2-one,

[4] 3-Benzyl-8-(4-methoxy-2,3,6-trimethylbenzolsulfonyl)-1,4,8-triazaspiro[4,5]decan-2-one,

[5] 2-[8-(4-Butoxy-benzolsulfonyl)-2-oxo-1,4,8-triazaspiro[4,5]dec-1-ylmethyl]-benzonitrile,

[6] 2-{8-[4-(1,1-Dimethylpropyl)benzolesulfonyl]-2-oxo-1,4,8-triazaspiro[4,5]dec-1-ylmethyl}-benzonitrile,

[7] 3-Benzyl-8-(2-fluorobenzolsulfonyl)-1,4,8-triazaspiro[4,5]decan-2-one,

[8] 8-(2-Chlorobenzolsulfonyl)-3-isopropyl-1,4,8-triazaspiro[4,5]decan-2-one,

[9] 1-Benzyl-2-oxo-1,4,8-triazaspiro[4,5]decan-8-sulfonic acid dimethylamide,

[10] 3-[8-(4-Acetylbenzolsulfonyl)-3-(2-methylsulfanylethyl)-2-oxo-1,4,8-triazaspiro[4,5]dec-1-ylmethyl]-benzonitrile,

[11] 1-(2-Fluorobenzyl)-3-isopropyl-8-(4-methoxy-2,3,6-trimethylbenzolsulfonyl)-1,4,8-triazaspiro[4,5]decan-2-one,

[12] 1-Butyl-8-(5-chlorothiophen-2-sulfonyl)-3-(2-methylsulfanylethyl)-1,4,8-triazaspiro[4,5]decan-2-one,

[13] 8-(4-Acetylbenzolsulfonyl)-1-butyl-3-(2-methylsulfanylethyl)-1,4,8-triazaspiro[4,5]decan-2-one,

[14] 1-Benzyl-3-isopropyl-8-(2,4,6-trimethylbenzolsulfonyl)-1,4,8-triazaspiro[4,5]decan-2-one,

[15] Methyl 2-(1-butyl-3-isopropyl-2-oxo-1,4,8-triazaspiro[4,5]decan-8-sulfonyl)benzoate,

[16] 1,3-Dibenzyl-8-(thiophen-2-sulfonyl)-1,4,8-triazaspiro[4,5]decan-2-one,

[17] 8-(3-Chloro-4-fluorobenzolsulfonyl)-3-isopropyl-1-(2-phenoxy-ethyl)-1,4,8-triazaspiro[4,5]decan-2-one,

[18] 1-Butyl-3-(2-methylsulfanylethyl)-8-(toluol-3-sulfonyl)-1,4,8-triazaspiro[4,5]decan-2-one,

[19] 1-Butyl-8-(2,4-difluorobenzolsulfonyl)-3-isopropyl-1,4,8-triazaspiro[4,5]decan-2-one,
[20] 1,3-Dibenzyl-8-(2,5-dichlorothiophen-3-sulfonyl)-1,4,8-triazaspiro[4,5]decan-2-one,
[21] 3-Isopropyl-1-(2-phenoxy-ethyl)-8-(toluol-4-sulfonyl)-1,4,8-triazaspiro[4,5]decan-2-one,
[22] 3-Benzyl-1-butyl-8-(2-trifluoromethylbenzolsulfonyl)-1,4,8-triazaspiro[4,5]decan-2-one,
[23] Methyl 2-[1-(4-fluorobenzyl)-3-(2-methylsulfanylethyl)-2-oxo-1,4,8-triazaspiro[4,5]decan-8-sulfonyl]-benzoate,
[24] 1,3-Dibenzyl-8-(2,3,5,6-tetramethylbenzolsulfonyl)-1,4,8-triazaspiro[4,5]decan-2-one,
[25] 1-(4-Fluorobenzyl)-3-(2-methylsulfanylethyl)-8-(2-trifluoromethylbenzolsulfonyl)-1,4,8-triazaspiro[4,5]decan-2-one,
[26] 8-(4-Chloro-2,5-dimethylbenzolsulfonyl)-1-(4-fluorobenzyl)-3-(2-methylsulfanylethyl)-1,4,8-triazaspiro[4,5]decan-2-one,
[27] 1-Benzyl-8-(4-chloro-2,5-dimethylbenzolsulfonyl)-3-isobutyl-1,4,8-triazaspiro[4,5]decan-2-one,
[28] 3-Benzyl-1-butyl-8-[4-(1,1-dimethylpropyl)benzolesulfonyl]-1,4,8-triazaspiro[4,5]decan-2-one,
[29] 1,3-Dibenzyl-8-(3,4-dimethoxy-benzolsulfonyl)-1,4,8-triazaspiro[4,5]decan-2-one,
[30] 1-Butyl-8-(3,4-dimethoxy-benzolsulfonyl)-3-(2-methylsulfanylethyl)-1,4,8-triazaspiro[4,5]decan-2-one,
[31] 1,3-Dibenzyl-8-(4-methoxy-2,3,6-trimethylbenzolsulfonyl)-1,4,8-triazaspiro[4,5]decan-2-one,
[32] 1-Benzyl-8-ethanesulfonyl-3-(2-methylsulfanylethyl)-1,4,8-triazaspiro[4,5]decan-2-one,
[33] 3-Benzyl-1-butyl-8-(4-ethylbenzolsulfonyl)-1,4,8-triazaspiro[4,5]decan-2-one,
[34] 3-(2-Methylsulfanylethyl)-1-prop-2-ynyl-8-(3-trifluoromethylbenzolsulfonyl)-1,4,8-triazaspiro[4,5]decan-2-one,
[35] 1,3-Dibenzyl-8-(4-ethylbenzolsulfonyl)-1,4,8-triazaspiro[4,5]decan-2-one,
[36] 3-Benzyl-1-butyl-8-(3-chlorobenzolsulfonyl)-1,4,8-triazaspiro[4,5]decan-2-one,
[37] 1,3-Dibenzyl-8-(2-fluorobenzolsulfonyl)-1,4,8-triazaspiro[4,5]decan-2-one,
[38] Methyl 2-[1-(2-cyanobenzyl)-3-(2-methylsulfanylethyl)-2-oxo-1,4,8-triazaspiro[4,5]decan-8-sulfonyl]-benzoate,
[39] 3-Benzyl-1-prop-2-ynyl-8-(2-trifluoromethylbenzolsulfonyl)-1,4,8-triazaspiro[4,5]decan-2-one,
[40] 3-Benzyl-8-(3-chlorobenzolsulfonyl)-1-methyl-1,4,8-triazaspiro[4,5]decan-2-one,
[41] 1-Benzyl-8-[4-(1,1-dimethylpropyl)benzole sulfonyl]-3-(2-methylsulfanylethyl)-1,4,8-triazaspiro[4,5]decan-2-one,
[42] 8-(2,4-Difluorobenzolsulfonyl)-1-(3,5-dimethylbenzyl)-3-(2-methylsulfanylethyl)-1,4,8-triazaspiro[4,5]decan-2-one,
[43] 1,3-Dibenzyl-8-(4-nitrobenzolsulfonyl)-1,4,8-triazaspiro[4,5]decan-2-one,
[44] 1-(4-Fluorobenzyl)-3-(2-methylsulfanylethyl)-8-(toluol-4-sulfonyl)-1,4,8-triazaspiro[4,5]decan-2-one,
[45] 1,3-Dibenzyl-8-(toluol-4-sulfonyl)-1,4,8-triazaspiro[4,5]decan-2-one,
[46] Ethyl[3-benzyl-8-(2-methyl-5-nitrobenzolsulfonyl)-2-oxo-1,4,8-triazaspiro[4,5]dec-1-yl]-acetate,
[47] Ethyl[3-benzyl-8-(2-methansulfonylbenzolsulfonyl)-2-oxo-1,4,8-triazaspiro[4,5]dec-1-yl]-acetate,
[48] 3 Ethyl-benzyl-2-oxo-8-(thiophen-2-sulfonyl)-1,4,8-triazaspiro[4,5]dec-1-yl]-acetate,
[49] Methyl 4-(8-ethanesulfonyl-2-oxo-1,4,8-triazaspiro[4,5]dec-1-ylmethyl)benzoate,
[50] Ethyl[3-benzyl-8-(4-methoxy-benzolsulfonyl)-2-oxo-1,4,8-triazaspiro[4,5]dec-1-yl]-acetate,
[51] Methyl 4-(2-Oxo-8-benzolmethansulfonyl-1,4,8-triazaspiro[4,5]dec-1-ylmethyl)benzoate,
[52] 3-[3-Isopropyl-8-(4-nitrobenzolsulfonyl)-2-oxo-1,4,8-triazaspiro[4,5]dec-1-ylmethyl]-benzonitrile,
[53] Methyl 4-[8-(butan-1-sulfonyl)-2-oxo-1,4,8-triazaspiro[4,5]dec-1-ylmethyl]-benzoate,
[54] 1-Allyl-8-(2-methansulfonylbenzolsulfonyl)-3-(2-methylsulfanylethyl)-1,4,8-triazaspiro[4,5]decan-2-one,
[55] 1-(2-Fluorobenzyl)-2-oxo-1,4,8-triazaspiro[4,5]decan-8-sulfonic acid dimethylamide,
[56] 8-(7,7-Dimethyl-2-oxobicyclo[2.2.1]hept-1-ylmethansulfonyl)-1-(2-fluorobenzyl)-1,4,8-triazaspiro[4,5]decan-2-one,
[57] Ethyl[3-(2-methylsulfanylethyl)-2-oxo-8-benzolmethansulfonyl-1,4,8-triazaspiro[4,5]dec-1-yl]-acetate,
[58] 1-Allyl-3-(2-methylsulfanylethyl)-8-benzolmethansulfonyl-1,4,8-triazaspiro[4,5]decan-2-one,
[59] 3-[2-Oxo-8-(2,4,6-trimethylbenzolsulfonyl)-1,4,8-triazaspiro[4,5]dec-1-ylmethyl]-benzonitrile,
[60] Methyl-4-[2-oxo-8-(2,4,6-trimethylbenzolsulfonyl)-1,4,8-triazaspiro[4,5]dec-1-ylmethyl]-benzoate,
[61] Ethyl[3-benzyl-8-(5-chlorothiophen-2-sulfonyl)-2-oxo-1,4,8-triazaspiro[4,5]dec-1-yl]-acetate,
[62] Ethyl[3-benzyl-8-(butan-1-sulfonyl)-2-oxo-1,4,8-triazaspiro[4,5]dec-1-yl]-acetate,
[63] Ethyl[3-benzyl-2-oxo-8-(toluol-3-sulfonyl)-1,4,8-triazaspiro[4,5]dec-1-yl]-acetate,
[64] 1-(2-Fluorobenzyl)-8-(4-methoxy-benzolsulfonyl)-1,4,8-triazaspiro[4,5]decan-2-one,
[65] Ethyl[3-benzyl-2-oxo-8-(2-trifluoromethylbenzolsulfonyl)-1,4,8-triazaspiro[4,5]dec-1-yl]-acetate,
[66] Ethyl(8-benzolsulfonyl-3-benzyl-2-oxo-1,4,8-triazaspiro[4,5]dec-1-yl)acetate,
[67] Ethyl[3-benzyl-2-oxo-8-(4-propylbenzolsulfonyl)-1,4,8-triazaspiro[4,5]dec-1-yl]-acetate,
[68] Ethyl(3-benzyl-2-oxo-8-benzolmethansulfonyl-1,4,8-triazaspiro[4,5]dec-1-yl)acetate,
[69] Ethyl[3-benzyl-8-(3-chloro-4-fluorobenzolsulfonyl)-2-oxo-1,4,8-triazaspiro[4,5]dec-1-yl]-acetate,
[70] 1-Allyl-3-isopropyl-8-(2,4,6-trimethylbenzolsulfonyl)-1,4,8-triazaspiro[4,5]decan-2-one,
[71] 8-Benzolsulfonyl-3-benzyl-1-(2-fluorobenzyl)-1,4,8-triazaspiro[4,5]decan-2-one,
[72] Ethyl[3-benzyl-2-oxo-8-(2,4,6-trimethylbenzolsulfonyl)-1,4,8-triazaspiro[4,5]dec-1-yl]-acetate,
[73] Ethyl[3-benzyl-8-(4-butoxy-benzolsulfonyl)-2-oxo-1,4,8-triazaspiro[4,5]dec-1-yl]-acetate,
[74] Ethyl[3-benzyl-8-(2,5-dimethoxy-benzolsulfonyl)-2-oxo-1,4,8-triazaspiro[4,5]dec-1-yl]-acetate,
[75] 3-(2-Methylsulfanylethyl)-1-naphthalin-2-ylmethyl-2-oxo-1,4,8-triazaspiro[4,5]decan-8-sulfonic acid dimethylamide,
[76] 1-(3-Cyanobenzyl)-3-isopropyl-2-oxo-1,4,8-triazaspiro[4,5]decan-8-sulfonic acid dimethylamide,
[77] 3-{3-Isopropyl-2-oxo-8-[2-(2,2,2-trifluoroacetyl)-1,2,3,4-tetrahydroisoquinolin-7-sulfonyl]-1,4,8-triazaspiro[4,5]dec-1-ylmethyl}-benzonitrile,
[78] 1-Allyl-3-(2-methylsulfanylethyl)-8-[2-(2,2,2-trifluoroacetyl)-1,2,3,4-tetrahydroisoquinolin-7-sulfonyl]-1,4,8-triazaspiro[4,5]decan-2-one,
[79] 1-Allyl-8-(4-methoxy-2,3,6-trimethylbenzolsulfonyl)-3-(2-methylsulfanylethyl)-1,4,8-triazaspiro[4,5]decan-2-one,

[80] Methyl 2-(3-benzyl-1-ethoxycarbonylmethyl-2-oxo-1,4,8-triazaspiro[4,5]decan-8-sulfonyl)benzoate,
[81] 3-Benzyl-1-(2-fluorobenzyl)-8-(2-trifluoromethylbenzolsulfonyl)-1,4,8-triazaspiro[4,5]decan-2-one,
[82] 8-(2-Chlorobenzolsulfonyl)-3-(2-methylsulfanylethyl)-1-(2-nitrobenzyl)-1,4,8-triazaspiro[4,5]decan-2-one,
[83] 1-Allyl-3-(2-methylsulfanylethyl)-8-(toluol-3-sulfonyl)-1,4,8-triazaspiro[4,5]decan-2-one,
[84] Ethyl[8-(2-chlorobenzolsulfonyl)-3-(2-methylsulfanylethyl)-2-oxo-1,4,8-triazaspiro[4,5]dec-1-yl]-acetate,
[85] 3-benzyl-1-(2-fluorobenzyl)-8-(toluol-4-sulfonyl)-1,4,8-triazaspiro[4,5]decan-2-one,
[86] Methyl 4-[8-(2,5-dichlorothiophen-3-sulfonyl)-2-oxo-1,4,8-triazaspiro[4,5]dec-1-ylmethyl]-benzoate,
[87] 3-[8-(4-Fluorobenzolsulfonyl)-3-isopropyl-2-oxo-1,4,8-triazaspiro[4,5]dec-1-ylmethyl]-benzonitrile,
[88] 8-(2,5-Dimethoxy-benzolsulfonyl)-3-(2-methylsulfanylethyl)-1-(2-nitrobenzyl)-1,4,8-triazaspiro[4,5]decan-2-one,
[89] 8-(3-Chloro-4-fluorobenzolsulfonyl)-1-(2-fluorobenzyl)-1,4,8-triazaspiro[4,5]decan-2-one,
[90] 1-(2-Fluorobenzyl)-8-(toluol-3-sulfonyl)-1,4,8-triazaspiro[4,5]decan-2-one,
[91] 1-(2,6-Dichlorobenzyl)-8-(4,5-dichlorothiophen-2-sulfonyl)-3-isobutyl-1,4,8-triazaspiro[4,5]decan-2-one,
[92] 8-(5-Chlorothiophen-2-sulfonyl)-1-(2-fluorobenzyl)-1,4,8-triazaspiro[4,5]decan-2-one,
[93] 3-Benzyl-1-(2-fluorobenzyl)-8-(4-propylbenzolsulfonyl)-1,4,8-triazaspiro[4,5]decan-2-one,
[94] 3-[8-(Butan-1-sulfonyl)-3-isopropyl-2-oxo-1,4,8-triazaspiro[4,5]dec-1-ylmethyl]-benzonitrile,
[95] 3-[8-(2-Methansulfonylbenzolsulfonyl)-2-oxo-1,4,8-triazaspiro[4,5]dec-1-ylmethyl]-benzonitrile,
[96] 8-(2-Fluorobenzolsulfonyl)-1-(2-fluorobenzyl)-1,4,8-triazaspiro[4,5]decan-2-one,
[97] Methyl 2-[1-(3-cyanobenzyl)-3-isopropyl-2-oxo-1,4,8-triazaspiro[4,5]decan-8-sulfonyl]-benzoate,
[98] 3-Benzyl-1-(2-fluorobenzyl)-8-(5-fluoro-2-methylbenzolsulfonyl)-1,4,8-triazaspiro[4,5]decan-2-one,
[99] 1-Allyl-8-(4-methoxy-benzolsulfonyl)-3-(2-methylsulfanylethyl)-1,4,8-triazaspiro[4,5]decan-2-one,
[100] 1-(3,5-Dimethylbenzyl)-3-isobutyl-8-(thiophen-2-sulfonyl)-1,4,8-triazaspiro[4,5]decan-2-one,
[101] 3-(2-Methylsulfanylethyl)-8-(4-nitrobenzolsulfonyl)-1-(2-nitrobenzyl)-1,4,8-triazaspiro[4,5]decan-2-one,
[102] 2-Isobutyl-3-oxo-1,4,8-triazaspiro[4,5]decan-8-thiocarboxylic acid o-tolylamide,
[103] 2-Benzyl-3-oxo-1,4,8-triazaspiro[4,5]decan-8-thiocarboxylic acid isopropylamide,
[104] 1-Butyl-3-isopropyl-2-oxo-1,4,8-triazaspiro[4,5]decan-8-thiocarboxylic acid (tetrahydrofuran-2-ylmethyl)amide,
[105] Ethyl 3-{[1-methyl-3-(2-methylsulfanylethyl)-2-oxo-1,4,8-triazaspiro[4,5]decan-8-carbothioyl]-amino}-butyrate,
[106] 1-Allyl-3-isopropyl-2-oxo-1,4,8-triazaspiro[4,5]decan-8-thiocarboxylic acid isopropylamide,
[107] 1-Butyl-3-isopropyl-2-oxo-1,4,8-triazaspiro[4,5]decan-8-thiocarboxylic acid isopropylamide,
[108] 3-Benzyl-1-(2-fluorobenzyl)-2-oxo-1,4,8-triazaspiro[4,5]decan-8-thiocarboxylic acid (2-methoxy-benzol)amide,
[109] Ethyl[8-Isopropylthiocarbamoyl-3-(2-methylsulfanylethyl)-2-oxo-1,4,8-triazaspiro[4,5]dec-1-yl]-4acetate,
[110] 1-Methyl-3-(2-methylsulfanylethyl)-2-oxo-1,4,8-triazaspiro[4,5]decan-8-thiocarboxylic acid m-tolylamide,
[111] 1-Methyl-3-(2-methylsulfanylethyl)-2-oxo-1,4,8-triazaspiro[4,5]decan-8-thiocarboxylic acid 4-methoxy-benzylamide,
[112] 2-Isobutyl-3-oxo-1,4,8-triazaspiro[4,5]decan-8-thiocarboxylic acid (4-fluorobenzol)amide,
[113] Ethyl[8-ethoxycarbonylaminocarbothioyl-3-(2-methylsulfanylethyl)-2-oxo-1,4,8-triazaspiro[4,5]dec-1-yl]-acetate
[114] Ethyl 3-{[1-ethoxycarbonylmethyl-3-(2-methylsulfanylethyl)-2-oxo-1,4,8-triazaspiro[4,5]decan-8-carbothioyl]-amino}-butyrate,
[115] 1-Allyl-3-isopropyl-2-oxo-1,4,8-triazaspiro[4,5]decan-8-thiocarboxylic acid (2-methoxy-benzol)amide,
[116] 1-Butyl-3-isopropyl-2-oxo-1,4,8-triazaspiro[4,5]decan-8-thiocarboxylic acid benzolamide,
[117] 1-Butyl-3-isopropyl-2-oxo-1,4,8-triazaspiro[4,5]decan-8-thiocarboxylic acid (2,5-dichlorobenzol)amide,
[118] 3-Benzyl-1-methyl-2-oxo-1,4,8-triazaspiro[4,5]decan-8-thiocarboxylic acid (2,5-difluorobenzol)amide,
[119] 1-Methyl-3-(2-methylsulfanylethyl)-2-oxo-1,4,8-triazaspiro[4,5]decan-8-thiocarboxylic acid (2-bromobenzol)amide,
[120] 1-Butyl-3-(2-methylsulfanylethyl)-2-oxo-1,4,8-triazaspiro[4,5]decan-8-thiocarboxylic acid (2,5-dichlorobenzol)amide,
[121] 3-(2-Methylsulfanylethyl)-1-naphthalin-2-ylmethyl-2-oxo-1,4,8-triazaspiro[4,5]decan-8-thiocarboxylic acid (2-methoxy-ethyl)amide,
[122] 1-Butyl-3-isopropyl-2-oxo-1,4,8-triazaspiro[4,5]decan-8-thiocarboxylic acid (2-fluorobenzol)amide,
[123] 3-Isobutyl-2-oxo-1-prop-2-ynyl-1,4,8-triazaspiro[4,5]decan-8-thiocarboxylic acid allylamide,
[124] 1-Butyl-3-isopropyl-2-oxo-1,4,8-triazaspiro[4,5]decan-8-thiocarboxylic acid m-tolylamide,
[125] 1-Allyl-3-isopropyl-2-oxo-1,4,8-triazaspiro[4,5]decan-8-thiocarboxylic acid (4-fluorobenzol)amide,
[126] Methyl 4-(8-allylthiocarbamoyl-3-isopropyl-2-oxo-1,4,8-triazaspiro[4,5]dec-1-ylmethyl)benzoate,
[127] 1-Butyl-3-(2-methylsulfanylethyl)-2-oxo-1,4,8-triazaspiro[4,5]decan-8-thiocarboxylic acid (2-methoxy-benzol)amide,
[128] 1-Allyl-3-isopropyl-2-oxo-1,4,8-triazaspiro[4,5]decan-8-thiocarboxylic acid (2,5-difluorobenzol)amide,
[129] 1-(2-Cyanobenzyl)-3-(2-methylsulfanylethyl)-2-oxo-1,4,8-triazaspiro[4,5]decan-8-thiocarboxylic acid allylamide,
[130] 1-(3-Cyanobenzyl)-3-(2-methylsulfanylethyl)-2-oxo-1,4,8-triazaspiro[4,5]decan-8-thiocarboxylic acid allylamide,
[131] Ethyl 3-[(3-benzyl-1-methyl-2-oxo-1,4,8-triazaspiro[4,5]decan-8-carbothioyl)amino]-butyrate,
[132] 1-Butyl-3-(2-methylsulfanylethyl)-2-oxo-1,4,8-triazaspiro[4,5]decan-8-thiocarboxylic acid cyclohexylmethylamide,
[133] 1-Methyl-3-(2-methylsulfanylethyl)-2-oxo-1,4,8-triazaspiro[4,5]decan-8-thiocarboxylic acid (4-chlorobenzol)amide,
[134] 1-Methyl-3-(2-methylsulfanylethyl)-2-oxo-1,4,8-triazaspiro[4,5]decan-8-thiocarboxylic acid 4-fluorobenzylamide,
[135] Methyl 4-[8-(2,6-dichlorobenzolthiocarbamoyl)-3-isopropyl-2-oxo-1,4,8-triazaspiro[4,5]dec-1-ylmethyl]-benzoate,
[136] 1-Benzyl-3-isopropyl-2-oxo-1,4,8-triazaspiro[4,5]decan-8-thiocarboxylic acid (2,5-dichlorobenzol)amide,

[137] Methyl 4-{3-isopropyl-2-oxo-8-[(tetrahydrofuran-2-ylmethyl)thiocarbamoyl]-1,4,8-triazaspiro[4,5]dec-1-ylmethyl}-benzoate,

[138] 1-Methyl-3-(2-methylsulfanylethyl)-2-oxo-1,4,8-triazaspiro[4,5]decan-8-thiocarboxylic acid (2,5-difluorobenzol)amide,

[139] 1-Benzyl-3-(2-methylsulfanylethyl)-2-oxo-1,4,8-triazaspiro[4,5]decan-8-thiocarboxylic acid (4-isopropylbenzol)amide,

[140] 1-Benzyl-3-(2-methylsulfanylethyl)-2-oxo-1,4,8-triazaspiro[4,5]decan-8-thiocarboxylic acid (2,5-difluorobenzol)amide,

[141] 1-(2-Cyanobenzyl)-3-isobutyl-2-oxo-1,4,8-triazaspiro[4,5]decan-8-thiocarboxylic acid (3-acetylbenzol)amide,

[142] 1-Butyl-3-isopropyl-2-oxo-1,4,8-triazaspiro[4,5]decan-8-thiocarboxylic acid (3-chlorobenzol)amide,

[143] Methyl 2-[(1-butyl-3-isopropyl-2-oxo-1,4,8-triazaspiro[4,5]decan-8-carbothioyl)amino]-benzoate,

[144] Ethyl(3-benzyl-8-ethoxycarbonylaminocarbothioyl-2-oxo-1,4,8-triazaspiro[4,5]dec-1-yl)acetate,

[145] Methyl 2-[(3-benzyl-1-ethoxycarbonylmethyl-2-oxo-1,4,8-triazaspiro[4,5]decan-8-carbothioyl)amino]-benzoate,

[146] Ethyl[1-(2-cyanobenzyl)-3-(2-methylsulfanylethyl)-2-oxo-1,4,8-triazaspiro[4,5]decan-8-carbothioyl]-carbamate,

[147] 1-(2-Cyanobenzyl)-3-(2-methylsulfanylethyl)-2-oxo-1,4,8-triazaspiro[4,5]decan-8-thiocarboxylic acid (2-chloro-5-trifluoromethylbenzol)amide,

[148] 3-(2-Methylsulfanylethyl)-1-naphthalin-2-ylmethyl-2-oxo-1,4,8-triazaspiro[4,5]decan-8-thiocarboxylic acid (1-benzol-ethyl)amide,

[149] 1-Allyl-3-isopropyl-2-oxo-1,4,8-triazaspiro[4,5]decan-8-thiocarboxylic acid pentafluorobenzolamide-amide,

[150] 1-Butyl-3-isopropyl-2-oxo-1,4,8-triazaspiro[4,5]decan-8-thiocarboxylic acid 4-chlorobenzylamide,

[151] 3-(2-Methylsulfanylethyl)-1-naphthalin-2-ylmethyl-2-oxo-1,4,8-triazaspiro[4,5]decan-8-thiocarboxylic acid o-tolylamide,

[152] 1-Butyl-3-isopropyl-2-oxo-1,4,8-triazaspiro[4,5]decan-8-thiocarboxylic acid pentafluorobenzolamide-amide,

[153] Methyl 2-{[1-(2-cyanobenzyl)-3-(2-methylsulfanylethyl)-2-oxo-1,4,8-triazaspiro[4,5]decan-8-carbothioyl]-amino}-benzoate,

[154] 1-Benzyl-3-isopropyl-2-oxo-1,4,8-triazaspiro[4,5]decan-8-thiocarboxylic acid pentafluorobenzolamide-amide,

[155] 1-Benzyl-3-isopropyl-2-oxo-1,4,8-triazaspiro[4,5]decan-8-thiocarboxylic acid (2-methoxy-benzol)amide,

[156] 1-Benzyl-3-isopropyl-2-oxo-1,4,8-triazaspiro[4,5]decan-8-thiocarboxylic acid benzolamide,

[157] 1-Benzyl-3-isopropyl-2-oxo-1,4,8-triazaspiro[4,5]decan-8-thiocarboxylic acid (2,5-difluorobenzol)amide,

[158] 1-Butyl-3-(2-methylsulfanylethyl)-2-oxo-1,4,8-triazaspiro[4,5]decan-8-thiocarboxylic acid (4-ethoxy-benzol)amide,

[159] Ethyl[3-benzyl-8-(cyclohexylmethylthiocarbamoyl)-2-oxo-1,4,8-triazaspiro[4,5]dec-1-yl]-acetate,

[160] 1-Butyl-3-(2-methylsulfanylethyl)-2-oxo-1,4,8-triazaspiro[4,5]decan-8-thiocarboxylic acid benzylamide,

[161] 1-(2-Cyanobenzyl)-3-(2-methylsulfanylethyl)-2-oxo-1,4,8-triazaspiro[4,5]decan-8-thiocarboxylic acid m-tolylamide,

[162] 1-Allyl-3-isopropyl-2-oxo-1,4,8-triazaspiro[4,5]decan-8-thiocarboxylic acid 4-fluorobenzylamide,

[163] 3-Isobutyl-2-oxo-1-prop-2-ynyl-1,4,8-triazaspiro[4,5]decan-8-thiocarboxylic acid (3-acetylbenzol)amide,

[164] Methyl 4-(3-isopropyl-2-oxo-8-pentafluorobenzolthiocarbamoyl-1,4,8-triazaspiro[4,5]dec-1-ylmethyl)benzoate,

[165] 3-(2-Methylsulfanylethyl)-1-naphthalin-2-ylmethyl-2-oxo-1,4,8-triazaspiro[4,5]decan-8-thiocarboxylic acid (3-acetylbenzol)amide,

[166] 3-Benzyl-1-(2-fluorobenzyl)-2-oxo-1,4,8-triazaspiro[4,5]decan-8-thiocarboxylic acid m-tolylamide,

[167] Methyl 4-(8-ethoxycarbonylaminocarbothioyl-3-isopropyl-2-oxo-1,4,8-triazaspiro[4,5]dec-1-ylmethyl)benzoate,

[168] 1-(4-Fluorobenzyl)-3-(2-methylsulfanylethyl)-2-oxo-1,4,8-triazaspiro[4,5]decan-8-thiocarboxylic acid (tetrahydrofuran-2-ylmethyl)amide,

[169] 1-(2-Cyanobenzyl)-3-isobutyl-2-oxo-1,4,8-triazaspiro[4,5]decan-8-thiocarboxylic acid (3,5-bis-trifluoromethylbenzol)amide,

[170] 1-(2-Cyanobenzyl)-3-isobutyl-2-oxo-1,4,8-triazaspiro[4,5]decan-8-thiocarboxylic acid benzylamide,

[171] 3-Benzyl-1-(2-fluorobenzyl)-2-oxo-1,4,8-triazaspiro[4,5]decan-8-thiocarboxylic acid cyclohexylmethylamide,

[172] 1-(3-Cyanobenzyl)-3-(2-methylsulfanylethyl)-2-oxo-1,4,8-triazaspiro[4,5]decan-8-thiocarboxylic acid (4-chlorobenzol)amide,

[173] 1-Butyl-3-(2-methylsulfanylethyl)-2-oxo-1,4,8-triazaspiro[4,5]decan-8-thiocarboxylic acid pentafluorobenzolamide-amide,

[174] Ethyl[3-benzyl-1-(2-fluorobenzyl)-2-oxo-1,4,8-triazaspiro[4,5]decan-8-carbothioyl]-carbamate,

[175] 3-Benzyl-1-methyl-2-oxo-1,4,8-triazaspiro[4,5]decan-8-thiocarboxylic acid 4-chlorobenzylamide,

[176] 1-(4-Fluorobenzyl)-3-(2-methylsulfanylethyl)-2-oxo-1,4,8-triazaspiro[4,5]decan-8-thiocarboxylic acid isopropylamide,

[177] 1-Benzyl-3-isopropyl-2-oxo-1,4,8-triazaspiro[4,5]decan-8-thiocarboxylic acid (3,5-dichlorobenzol)amide,

[178] Ethyl[1-(3-cyanobenzyl)-3-(2-methylsulfanylethyl)-2-oxo-1,4,8-triazaspiro[4,5]decan-8-carbothioyl]-carbamate,

[179] 1-Benzyl-3-isopropyl-2-oxo-1,4,8-triazaspiro[4,5]decan-8-thiocarboxylic acid 4-fluorobenzylamide,

[180] 1-Allyl-3-isopropyl-2-oxo-1,4,8-triazaspiro[4,5]decan-8-thiocarboxylic acid (3,5-dichlorobenzol)amide,

[181] 1-(3-Cyanobenzyl)-3-(2-methylsulfanylethyl)-2-oxo-1,4,8-triazaspiro[4,5]decan-8-thiocarboxylic acid (1-benzol-ethyl)amide,

[182] 1-(4-Fluorobenzyl)-3-(2-methylsulfanylethyl)-2-oxo-1,4,8-triazaspiro[4,5]decan-8-thiocarboxylic acid 4-fluorobenzylamide,

[183] 1-(2-Cyanobenzyl)-3-(2-methylsulfanylethyl)-2-oxo-1,4,8-triazaspiro[4,5]decan-8-thiocarboxylic acid (2-methoxy-benzol)amide,

[184] 1-(3-Cyanobenzyl)-3-(2-methylsulfanylethyl)-2-oxo-1,4,8-triazaspiro[4,5]decan-8-thiocarboxylic acid (2-methoxy-benzol)amide,

[185] 1-(3-Cyanobenzyl)-3-(2-methylsulfanylethyl)-2-oxo-1,4,8-triazaspiro[4,5]decan-8-thiocarboxylic acid 4-chlorobenzylamide,

[186] 1-(4-Fluorobenzyl)-3-(2-methylsulfanylethyl)-2-oxo-1,4,8-triazaspiro[4,5]decan-8-thiocarboxylic acid o-tolylamide,

[187] 3-Benzyl-1-(2-fluorobenzyl)-2-oxo-1,4,8-triazaspiro[4,5]decan-8-thiocarboxylic acid (2,6-dichlorobenzol)amide,

[188] 3-Benzyl-1-(2-fluorobenzyl)-2-oxo-1,4,8-triazaspiro[4,5]decan-8-thiocarboxylic acid (2-chloro-5-trifluoromethylbenzol)amide,

[189] 1-Butyl-3-(2-methylsulfanylethyl)-2-oxo-1,4,8-triazaspiro[4,5]decan-8-thiocarboxylic acid (4-fluorobenzol)amide,

[190] 3-Isobutyl-2-oxo-1-prop-2-ynyl-1,4,8-triazaspiro[4,5]decan-8-thiocarboxylic acid (2,6-dichlorobenzol)amide,

[191] Methyl 4-[8-(4-chlorobenzylthiocarbamoyl)-3-isopropyl-2-oxo-1,4,8-triazaspiro[4,5]dec-1-ylmethyl]-benzoate,

[192] 1-(4-Fluorobenzyl)-3-(2-methylsulfanylethyl)-2-oxo-1,4,8-triazaspiro[4,5]decan-8-thiocarboxylic acid (3-cyanobenzol)amide,

[193] 1-(2-Cyanobenzyl)-3-(2-methylsulfanylethyl)-2-oxo-1,4,8-triazaspiro[4,5]decan-8-thiocarboxylic acid 4-chlorobenzylamide,

[194] 1-Methyl-3-(2-methylsulfanylethyl)-2-oxo-1,4,8-triazaspiro[4,5]decan-8-thiocarboxylic acid (3-trifluoromethylbenzol)amide,

[195] 3-Isobutyl-2-oxo-1-prop-2-ynyl-1,4,8-triazaspiro[4,5]decan-8-thiocarboxylic acid (3,5-dichlorobenzol)amide,

[196] 1-(4-Fluorobenzyl)-3-(2-methylsulfanylethyl)-2-oxo-1,4,8-triazaspiro[4,5]decan-8-thiocarboxylic acid (1-benzol-ethyl)amide,

[197] 3-Benzyl-1-(2-fluorobenzyl)-2-oxo-1,4,8-triazaspiro[4,5]decan-8-thiocarboxylic acid 4-chlorobenzylamide,

[198] 2-Isopropyl-3-oxo-1,4,8-triazaspiro[4,5]decan-8-thiocarboxylic acid (4-fluorobenzol)amide,

[199] 1-Benzyl-3-isopropyl-2-oxo-1,4,8-triazaspiro[4,5]decan-8-thiocarboxylic acid benzylamide,

[200] 1-(4-Fluorobenzyl)-3-(2-methylsulfanylethyl)-2-oxo-1,4,8-triazaspiro[4,5]decan-8-thiocarboxylic acid (4-ethoxy-benzol)amide,

[201] 3-Benzyl-1-(2-fluorobenzyl)-2-oxo-1,4,8-triazaspiro[4,5]decan-8-thiocarboxylic acid (3-acetylbenzol)amide,

[202] 3-Benzyl-1-methyl-2-oxo-1,4,8-triazaspiro[4,5]decan-8-carboxylic acid cyclohexylamide,

[203] Ethyl[3-(2-methylsulfanylethyl)-2-oxo-8-benzolcarbamoyl-1,4,8-triazaspiro[4,5]dec-1-yl]-acetate,

[204] 1-Allyl-3-isopropyl-2-oxo-1,4,8-triazaspiro[4,5]decan-8-carboxylic acid (2,5-dimethoxy-benzol)amide,

[205] 1-Methyl-3-(2-methylsulfanylethyl)-2-oxo-1,4,8-triazaspiro[4,5]decan-8-carboxylic acid (3-fluorobenzol)amide,

[206] Methyl 4-(8-cyclohexylcarbamoyl-3-isopropyl-2-oxo-1,4,8-triazaspiro[4,5]dec-1-ylmethyl)benzoate,

[207] 1-Butyl-3-(2-methylsulfanylethyl)-2-oxo-1,4,8-triazaspiro[4,5]decan-8-carboxylic acid benzolamide,

[208] 1-Benzyl-3-(2-methylsulfanylethyl)-2-oxo-1,4,8-triazaspiro[4,5]decan-8-carboxylic acid (3-cyanobenzol)amide,

[209] 1-Allyl-3-isopropyl-2-oxo-1,4,8-triazaspiro[4,5]decan-8-carboxylic acid (2,5-difluorobenzol)amide,

[210] 1-Butyl-3-(2-methylsulfanylethyl)-2-oxo-1,4,8-triazaspiro[4,5]decan-8-carboxylic acid (3,4,5-trimethoxy-benzol)amide,

[211] 1-Benzyl-3-(2-methylsulfanylethyl)-2-oxo-1,4,8-triazaspiro[4,5]decan-8-carboxylic acid (4-chloro-3-trifluoromethylbenzol)amide,

[212] 1-Methyl-3-(2-methylsulfanylethyl)-2-oxo-1,4,8-triazaspiro[4,5]decan-8-carboxylic acid (5-chloro-2-methoxy-benzol)amide,

[213] 1-Benzyl-3-(2-methylsulfanylethyl)-2-oxo-1,4,8-triazaspiro[4,5]decan-8-carboxylic acid (4-ethoxy-benzol)amide,

[214] 1-Benzyl-3-(2-methylsulfanylethyl)-2-oxo-1,4,8-triazaspiro[4,5]decan-8-carboxylic acid (3-acetylbenzol)amide,

[215] Ethyl 3-[(1-butyl-3-isopropyl-2-oxo-1,4,8-triazaspiro[4,5]decan-8-carbonyl)amino]-benzoate,

[216] 1-Butyl-3-isopropyl-2-oxo-1,4,8-triazaspiro[4,5]decan-8-carboxylic acid (2,5-dimethoxy-benzol)amide,

[217] 1-(2-Cyanobenzyl)-3-isobutyl-2-oxo-1,4,8-triazaspiro[4,5]decan-8-carboxylic acid 3,4-dichlorobenzylamide,

[218] 1-(2-Cyanobenzyl)-3-isobutyl-2-oxo-1,4,8-triazaspiro[4,5]decan-8-carboxylic acid (2,5-difluorobenzol)amide,

[219] 1-Butyl-3-(2-methylsulfanylethyl)-2-oxo-1,4,8-triazaspiro[4,5]decan-8-carboxylic acid 3,4-dichlorobenzylamide,

[220] 1-Allyl-3-isopropyl-2-oxo-1,4,8-triazaspiro[4,5]decan-8-carboxylic acid (4-trifluoromethoxy-benzol)amide,

[221] 1-Butyl-3-(2-methylsulfanylethyl)-2-oxo-1,4,8-triazaspiro[4,5]decan-8-carboxylic acid (4-ethoxy-benzol)amide,

[222] 1-Methyl-3-(2-methylsulfanylethyl)-2-oxo-1,4,8-triazaspiro[4,5]decan-8-carboxylic acid (4-trifluoromethoxy-benzol)amide,

[223] Methyl 4-[3-isopropyl-8-(3-methoxy-benzolcarbamoyl)-2-oxo-1,4,8-triazaspiro[4,5]dec-1-ylmethyl]-benzoate,

[224] 1-(2-Cyanobenzyl)-3-(2-methylsulfanylethyl)-2-oxo-1,4,8-triazaspiro[4,5]decan-8-carboxylic acid benzolamide,

[225] Ethyl[3-benzyl-8-(3,4-dichlorobenzylcarbamoyl)-2-oxo-1,4,8-triazaspiro[4,5]dec-1-yl]-acetate,

[226] 1-(2-Cyanobenzyl)-3-(2-methylsulfanylethyl)-2-oxo-1,4,8-triazaspiro[4,5]decan-8-carboxylic acid (3-fluorobenzol)amide,

[227] 1-Butyl-3-(2-methylsulfanylethyl)-2-oxo-1,4,8-triazaspiro[4,5]decan-8-carboxylic acid (4-chloro-3-trifluoromethylbenzol)amide,

[228] 1-(4-Fluorobenzyl)-3-(2-methylsulfanylethyl)-2-oxo-1,4,8-triazaspiro[4,5]decan-8-carboxylic acid 3,4-dichlorobenzylamide,

[229] 1-(2-Cyanobenzyl)-3-(2-methylsulfanylethyl)-2-oxo-1,4,8-triazaspiro[4,5]decan-8-carboxylic acid 3,4-dichlorobenzylamide,

[230] 3-Benzyl-1-(2-fluorobenzyl)-2-oxo-1,4,8-triazaspiro[4,5]decan-8-carboxylic acid (2,5-difluorobenzol)amide,

[231] 3-(2-Methylsulfanylethyl)-1-naphthalin-2-ylmethyl-2-oxo-1,4,8-triazaspiro[4,5]decan-8-carboxylic acid (4-ethoxy-benzol)amide,

[232] Methyl 4-[8-(3,4-dichlorobenzylcarbamoyl)-3-isopropyl-2-oxo-1,4,8-triazaspiro[4,5]dec-1-ylmethyl]-benzoate,

[233] 3-Benzyl-1-(2-fluorobenzyl)-2-oxo-1,4,8-triazaspiro[4,5]decan-8-carboxylic acid 3,4-dichlorobenzylamide,

[234] 1-(2-Cyanobenzyl)-3-(2-methylsulfanylethyl)-2-oxo-1,4,8-triazaspiro[4,5]decan-8-carboxylic acid (3-acetylbenzol)amide,

[235] Ethyl 4-{[3-benzyl-1-(2-fluorobenzyl)-2-oxo-1,4,8-triazaspiro[4,5]decan-8-carbonyl]-amino}-benzoate,

[236] 1-(3-Cyanobenzyl)-3-(2-methylsulfanylethyl)-2-oxo-1,4,8-triazaspiro[4,5]decan-8-carboxylic acid (3-methoxy-benzol)amide,

[237] 1-(4-Fluorobenzyl)-3-(2-methylsulfanylethyl)-2-oxo-1,4,8-triazaspiro[4,5]decan-8-carboxylic acid (4-trifluoromethoxy-benzol)amide,

[238] 3-Benzyl-1-(2-fluorobenzyl)-2-oxo-1,4,8-triazaspiro[4,5]decan-8-carboxylic acid cyclohexylamide,

[239] 1-(4-Fluorobenzyl)-3-(2-methylsulfanylethyl)-2-oxo-1,4,8-triazaspiro[4,5]decan-8-carboxylic acid phenethylamide,

[240] 3-(2-Methylsulfanylethyl)-1-naphthalin-2-ylmethyl-2-oxo-1,4,8-triazaspiro[4,5]decan-8-carboxylic acid (3-fluorobenzol)amide,
[241] Methyl 4-[8-(4-chloro-3-trifluoromethylbenzolcarbamoyl)-3-isopropyl-2-oxo-1,4,8-triazaspiro[4,5]dec-1-ylmethyl]-benzoate,
[242] 1-(3-Cyanobenzyl)-3-(2-methylsulfanylethyl)-2-oxo-1,4,8-triazaspiro[4,5]decan-8-carboxylic acid (2,5-dimethoxy-benzol)amide,
[243] 1-(4-Fluorobenzyl)-3-(2-methylsulfanylethyl)-2-oxo-1,4,8-triazaspiro[4,5]decan-8-carboxylic acid (4-ethoxybenzol)amide,
[244] 1-(4-Fluorobenzyl)-3-(2-methylsulfanylethyl)-2-oxo-1,4,8-triazaspiro[4,5]decan-8-carboxylic acid (3-cyanobenzol)amide, and
[245] Ethyl[3-b-8-(3-fluorobenzolcarbamoyl)-2-oxo-1,4,8-triazaspiro[4,5]dec-1-yl]-acetate,
[246] 1,3-Dibenzyl-8-methansulfonyl-1,4,8-triazaspiro[4,5]decan-2-one,
[247] 8-Benzolsulfonyl-1,3-dibenzyl-1,4,8-triazaspiro[4,5]decan-2-one,
[248] 1,3-Dibenzyl-8-(4-chlorobenzolsulfonyl)-1,4,8-triazaspiro[4,5]decan-2-one,
[249] 1,3-Dibenzyl-8-(4-methoxy-benzolsulfonyl)-1,4,8-triazaspiro[4,5]decan-2-one,
[250] 1,3-Dibenzyl-2-oxo-1,4,8-triazaspiro[4,5]decan-8-carboxylic acid phenylamide,
[251] 1,3-Dibenzyl-2-oxo-1,4,8-triazaspiro[4,5]decan-8-carboxylic acid (4-methoxy-phenyl)amide,
[252] 1,3-Dibenzyl-2-oxo-1,4,8-triazaspiro[4,5]decan-8-thiocarboxylic acid phenylamide,
[253] 1,3-Dibenzyl-2-oxo-1,4,8-triazaspiro[4,5]decan-8-thiocarboxylic acid (2,4-difluorophenyl)amide, Pharmacological Data:

The affinity of the substituted 1,4,8-triazaspiro[4,5]decan-2-one compounds of the invention of the general formula I to the batrachotoxin (BTX) binding site of the sodium channel and to the cannabinoid receptor CB2 and also the inhibition of noradrenalin reuptake or 5-HT reuptake were determined as described above.

The substituted 1,4,8-triazaspiro[4,5]decan-2-one compounds of the invention of the above general formula I show good to very good inhibition of noradrenalin reuptake and also good to very good inhibition of 5-hydroxy tryptophane reuptake.

Furthermore, these compounds of the invention also show excellent affinities to the batrachotoxin (BTX) binding site of the sodium channel.

The substituted 1,4,8-triazaspiro[4,5]decan-2-one compounds of the invention likewise show a high affinity to the cannabinoid receptor CB2 (CB2 receptors).

The following Tables I, II. and III list the respective pharmacological data for substituted 1,4,8-triazaspiro[4,5]decan-2-one compounds according to the examples.

TABLE I

| Example | BTX Inhibition | Uptake_5-HT, rat, 1 μM, % inhibition | Uptake (NA), rat, 10 μM, % inhibition |
|---|---|---|---|
| 1 | | 55 | |
| 4 | 53 | | 34 |
| 5 | 59 | 30 | |
| 6 | 56 | 57 | |
| 7 | | 54 | 32 |
| 8 | | 55 | |
| 9 | | | 40 |
| 10 | | 35 | 39 |
| 11 | | 52 | 37 |
| 12 | | 58 | |
| 13 | | 56 | |
| 14 | 68 | 61 | |
| 15 | | 44 | |
| 16 | 50 | 82 | |
| 17 | 41 | | |
| 18 | 32 | 68 | |
| 19 | 30 | | |
| 20 | 54 | 81 | |
| 21 | 54 | | |
| 22 | 38 | 66 | |
| 23 | 40 | 69 | |
| 24 | 67 | 66 | |
| 25 | 57 | 58 | |
| 26 | 38 | 68 | |
| 27 | 59 | | |
| 28 | 41 | 75 | |
| 29 | 47 | 75 | |
| 30 | | 53 | |
| 31 | 82 | 67 | |
| 32 | | 64 | |
| 33 | 54 | 67 | |
| 34 | | | |
| 35 | 54 | 79 | |
| 36 | 49 | 65 | |
| 37 | 61 | 73 | |
| 38 | | 40 | |
| 39 | 39 | 38 | 41 |
| 40 | | 57 | |
| 41 | | 56 | |
| 42 | 56 | | |
| 43 | 51 | 71 | |
| 44 | 42 | 42 | |
| 45 | 37 | 74 | |
| 46 | 30 | 90 | 33 |
| 47 | 31 | 71 | 47 |
| 48 | 30 | 85 | |
| 50 | 32 | 79 | 38 |
| 51 | 31 | 62 | |
| 52 | | 53 | |
| 53 | 31 | 45 | 30 |
| 54 | | 30 | 46 |
| 55 | | 57 | |
| 56 | 32 | 60 | |
| 57 | 34 | 32 | |
| 58 | | 56 | |
| 59 | 50 | 50 | |
| 60 | 59 | 65 | |
| 61 | 50 | 61 | |
| 62 | | 70 | |
| 63 | 36 | 59 | |
| 64 | 42 | | |
| 65 | 51 | 71 | 33 |
| 66 | 39 | 64 | |
| 67 | 40 | 64 | |
| 68 | 47 | 69 | 31 |
| 69 | 73 | 62 | |
| 70 | 60 | | |
| 71 | 85 | 76 | |
| 72 | 75 | 75 | |
| 73 | 52 | 80 | |
| 74 | 30 | 74 | |
| 75 | 62 | 74 | |
| 76 | | | |
| 77 | 36 | 32 | |
| 78 | 32 | | |
| 79 | 67 | 37 | |
| 80 | 33 | 84 | |
| 81 | 87 | 81 | |
| 82 | 71 | 49 | |
| 83 | | | |
| 84 | | | |

TABLE I-continued

| Example | BTX Inhibition | Uptake_5-HT, rat, 1 μM, % inhibition | Uptake (NA), rat, 10 μM, % inhibition |
|---|---|---|---|
| 86 | | | |
| 91 | | | |
| 92 | | | |
| 93 | | | |
| 100 | | | |
| 101 | | | |

TABLE II

| Example | BTX inihibition | Uptake_5-HT, rat, 1 μM, % inhibition | Uptake (NA), rat, 10 μM, % inhibition |
|---|---|---|---|
| 102 | | — | |
| 103 | | 41 | |
| 107 | | 28 | |
| 108 | 86 | 86 | 31 |
| 111 | 51 | | — |
| 112 | 30 | 31 | |
| 116 | 30 | 40 | |
| 117 | 44 | 33 | |
| 118 | 42 | | |
| 120 | 49 | 58 | |
| 121 | 47 | 39 | |
| 122 | 35 | 32 | |
| 123 | | | |
| 124 | 41 | 47 | |
| 125 | | 34 | |
| 126 | 37 | | |
| 127 | 44 | | |
| 128 | 33 | 57 | |
| 129 | 36 | 41 | |
| 131 | 42 | | 42 |
| 132 | 71 | 30 | |
| 133 | 44 | | |
| 134 | 50 | | |
| 135 | 38 | | |
| 136 | 66 | 44 | |
| 137 | 37 | | 30 |
| 138 | 34 | | |
| 139 | 97 | 63 | |
| 140 | 53 | 59 | |
| 141 | 50 | | |
| 142 | 63 | | |
| 143 | 51 | 32 | |
| 144 | | 47 | |
| 145 | 69 | 67 | |
| 146 | 30 | 30 | |
| 147 | 81 | 33 | |
| 148 | 88 | 49 | |
| 149 | | 55 | |
| 150 | 73 | 51 | 30 |
| 151 | 84 | 64 | 42 |
| 152 | 39 | | 37 |
| 153 | 53 | | 30 |
| 154 | 61 | 34 | 43 |
| 155 | 32 | | 52 |
| 156 | | | 33 |
| 157 | 39 | | 38 |
| 158 | 35 | 33 | 41 |
| 159 | 84 | 33 | 36 |
| 160 | 63 | | 42 |
| 161 | 53 | | 33 |
| 162 | | | 26 |
| 163 | | 38 | 34 |
| 164 | 42 | | 58 |
| 165 | 64 | 42 | 48 |
| 166 | 85 | 64 | 39 |
| 167 | | | 42 |
| 168 | 38 | | 35 |
| 169 | 91 | | 44 |

TABLE II-continued

| Example | BTX inihibition | Uptake_5-HT, rat, 1 μM, % inhibition | Uptake (NA), rat, 10 μM, % inhibition |
|---|---|---|---|
| 170 | 53 | | 46 |
| 171 | 86 | | 34 |
| 172 | 59 | | 47 |
| 173 | 40 | | 45 |
| 174 | 38 | 31 | 39 |
| 175 | 63 | | 32 |
| 176 | | 32 | |
| 177 | 46 | 36 | |
| 178 | | | |
| 179 | 58 | 47 | |
| 180 | 54 | | |
| 181 | 57 | | 40 |
| 182 | 69 | 30 | |
| 183 | 37 | | 29 |
| 184 | 36 | | 32 |
| 185 | 72 | | |
| 186 | 52 | 55 | |
| 187 | 86 | 54 | 39 |
| 188 | 77 | 59 | |
| 189 | 41 | 66 | 30 |
| 190 | 53 | | |
| 191 | 74 | | |
| 192 | 35 | 38 | |
| 193 | 72 | | 32 |
| 194 | 36 | | |
| 195 | 77 | | 30 |
| 196 | 70 | | |
| 197 | 77 | | |
| 198 | | | |
| 199 | 44 | | |
| 200 | 30 | 30 | |
| 201 | 63 | 54 | |
| 202 | 56 | 34 | |
| 203 | 32 | | 40 |
| 204 | | | |
| 205 | | | |
| 206 | | | 39 |
| 207 | 35 | 39 | |
| 208 | 41 | 45 | 49 |
| 209 | 31 | | |
| 210 | 44 | 32 | 36 |
| 211 | 85 | 45 | 40 |
| 212 | | | |
| 213 | 41 | 39 | 37 |
| 214 | 40 | 51 | 36 |
| 215 | 51 | 29 | 33 |
| 216 | | 46 | 30 |
| 217 | 78 | | 39 |
| 218 | 40 | | |
| 219 | 70 | 37 | 42 |
| 220 | 44 | 39 | 39 |
| 221 | 44 | 47 | |
| 222 | 48 | | 30 |
| 223 | | | 31 |
| 224 | 30 | 37 | 38 |
| 225 | 77 | 43 | 33 |
| 226 | | 55 | |
| 227 | 85 | 58 | |
| 228 | 87 | | |
| 229 | 69 | | 40 |
| 230 | 78 | 63 | |
| 231 | 79 | 59 | |
| 232 | 55 | | |
| 233 | 85 | 44 | |
| 234 | 31 | 45 | |
| 235 | 77 | 65 | |
| 236 | 42 | 32 | 34 |
| 237 | 87 | 39 | |
| 238 | 73 | 43 | |
| 239 | 69 | 36 | |
| 240 | 78 | 63 | |
| 241 | 78 | 31 | |
| 242 | 46 | 30 | |
| 243 | 48 | 40 | |

TABLE II-continued

| Example | BTX inihibition | Uptake_5-HT, rat, 1 μM, % inhibition | Uptake (NA), rat, 10 μM, % inhibition |
|---|---|---|---|
| 244 | 47 | 52 | 32 |
| 245 | 31 | 51 | |

TABLE III

| Example | Inhibition CB2 10 μM, % inhibition | $K_i$ |
|---|---|---|
| 8 | 41 | |
| 16 | 58 | |
| 20 | 66 | |
| 24 | 56 | |
| 28 | 40 | |
| 31 | 57 | |
| 35 | 61 | |
| 36 | 40 | |
| 42 | 48 | |
| 43 | 62 | |
| 50 | 52 | |
| 54 | 56 | |
| 73 | 46 | |
| 82 | 56 | |
| 107 | 56 | |
| 147 | 48 | |
| 171 | 41 | |
| 179 | 43 | |
| 182 | 64 | |
| 187 | 84 | |
| 188 | 49 | |
| 231 | 49 | |
| 246 | 50 | |
| 247 | 72 | 4.0 |
| 248 | 87 | 1.2 |
| 249 | 80 | 3.5 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A 1,4,8-triazaspiro[4,5]decan-2-one compound corresponding to formula I,

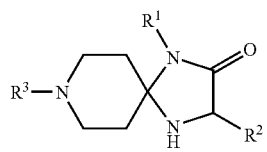

wherein
R$^1$ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group which may comprise at least one heteroatom as a link; or a —C(=O)OR$^7$ group which may be bonded via a linear or branched alkylene group;

R$^2$ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl group may be bonded via a linear or branched alkylene group which may comprise at least one heteroatom as a link;

R$^3$ represents a —S(=O)$_2$—R$^4$ group; a —C(=S)NH—R$^5$ group; or a —C(=O)NH—R$^6$ group;

R$^4$ represents a —NR$^{10}$R$^{11}$ group; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group, which may comprise at least one heteroatom as a ring member and which may be bonded via a linear or branched unsubstituted or at least monosubstituted alkylene group which may comprise at least one heteroatom as a link and which may be bridged by a linear or branched unsubstituted or at least monosubstituted alkylene group;

R$^5$ represents a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group which may comprise at least one heteroatom as a link; an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link; a —C(=O)OR$^8$ group or a —C(=O)OR$^9$ group, which may, in either case, be bonded via a linear or branched alkylene group;

$R^6$ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group which may comprise at least one heteroatom as a link; or for an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link;

$R^7$, $R^8$, $R^9$, $R^{10}$, and $R^{11}$, each independently represent a linear or branched alkyl group, a linear or branched alkenyl group, or a linear or branched alkynyl group, or a physiologically acceptable salt thereof.

2. The compound of claim 1, wherein said compound is present in the form of a pure enantiomer or pure diastereoisomer.

3. The compound of claim 1, wherein said compound is present in the form of a mixture of stereoisomers.

4. The compound of claim 1, wherein said compound is present in the form of a racemic mixture.

5. The compound of claim 1, wherein $R^1$ represents hydrogen; a linear or branched unsubstituted or at least monosubstituted $C_{1-10}$ alkyl group which may comprise at least one heteroatom as a link; a linear or branched unsubstituted or at least monosubstituted $C_{2-10}$ alkenyl group which may comprise at least one heteroatom as a link; a linear or branched unsubstituted or at least monosubstituted $C_{2-10}$ alkynyl group which may comprise at least one heteroatom as a link; an unsubstituted or at least monosubstituted five-membered to fourteen-membered aryl group or heteroaryl group, which may be bonded via a linear or branched $C_{1-5}$ alkylene group which may comprise at least one heteroatom as a link; a —C(═O)OR$^7$ group which may be bonded via a linear or branched $C_{1-5}$ alkylene group;

$R^2$ represents hydrogen; a linear or branched unsubstituted or at least monosubstituted $C_{1-10}$ alkyl group which may comprise at least one heteroatom as a link; a linear or branched unsubstituted or at least monosubstituted $C_{2-10}$ alkenyl group which may comprise at least one heteroatom as a link; a linear or branched unsubstituted or at least monosubstituted $C_{2-10}$ alkynyl group which may comprise at least one heteroatom as a link; an unsubstituted or at least monosubstituted five-membered to fourteen-membered aryl or heteroaryl group, which may be bonded via a linear or branched $C_{1-5}$ alkylene group which may comprise at least one heteroatom as a link;

$R^4$ represents an NR$^{10}$R$^{11}$ group; a linear or branched unsubstituted or at least monosubstituted $C_{1-10}$ alkyl group which may comprise at least one heteroatom as a link; a linear or branched unsubstituted or at least monosubstituted $C_{2-10}$ alkenyl group which may comprise at least one heteroatom as a link; a linear or branched unsubstituted or at least monosubstituted $C_{2-10}$ alkynyl group which may comprise at least one heteroatom as a link; an unsubstituted or at least monosubstituted five-membered to fourteen-membered aryl group or heteroaryl group, which may be bonded via a linear or branched unsubstituted or at least monosubstituted $C_{1-5}$ alkylene group which may comprise at least one heteroatom as a link and may be condensed with a five-membered or six-membered monocyclic ring system; an unsubstituted or at least monosubstituted $C_{3-8}$-cycloaliphatic group which may comprise at least one heteroatom as a ring member or which may be bonded via a linear or branched unsubstituted or at least monosubstituted $C_{1-5}$ alkylene group which may comprise at least one heteroatom as a link and which may be bridged by a linear or branched unsubstituted or at least monosubstituted $C_{1-5}$ alkylene group;

$R^5$ represents a linear or branched unsubstituted or at least monosubstituted $C_{1-10}$ alkyl group which may comprise at least one heteroatom as a link; a linear or branched unsubstituted or at least monosubstituted $C_{2-10}$ alkenyl group which may comprise at least one heteroatom as a link; a linear or branched unsubstituted or at least monosubstituted $C_{2-10}$ alkynyl group which may comprise at least one heteroatom as a link; an unsubstituted or at least monosubstituted five-membered to fourteen-membered aryl or heteroaryl group, which may be bonded via a linear or branched unsubstituted or at least monosubstituted $C_{1-5}$ alkylene group which may comprise at least one heteroatom as a link; an unsubstituted or at least monosubstituted $C_{3-8}$ cycloaliphatic group which may comprise at least one heteroatom as a ring member and which may be bonded via a linear or branched unsubstituted or at least monosubstituted $C_{1-5}$ alkylene group which may comprise at least one heteroatom as a link; a —C(═O)OR$^8$ group or a —C(═O)OR$^9$ group either of which may be bonded via a linear or branched $C_{1-5}$ alkylene group;

$R^6$ represents an unsubstituted or at least monosubstituted five-membered to fourteen-membered aryl or heteroaryl group, which aryl or heteroaryl group may be bonded via a linear or branched unsubstituted or at least monosubstituted $C_{1-5}$ alkylene group which may comprise at least one heteroatom as a link; an unsubstituted or at least monosubstituted $C_{3-8}$ cycloaliphatic group which may comprise at least one heteroatom as a ring member, or which may be bonded via a linear or branched unsubstituted or at least monosubstituted $C_{1-5}$ alkylene group which may comprise at least one heteroatom as a link;

and $R^7$, $R^8$, $R^9$, and $R^{10}$, $R^{11}$, independently represent a linear or branched $C_{1-5}$ alkyl group, a linear or branched $C_{2-5}$ alkenyl group, or a linear or branched $C_{2-5}$ alkynyl group.

6. The compound of claim 1, wherein $R^1$ represents hydrogen, a linear or branched unsubstituted $C_{1-5}$ alkyl group; a linear or branched unsubstituted $C_{2-5}$ alkenyl group; a linear or branched unsubstituted $C_{2-5}$ alkynyl group; an unsubstituted or at least monosubstituted phenyl group; or an unsubstituted or at least monosubstituted naphthyl group; any of which groups may be bonded via a linear or branched $C_{1-5}$ alkylene group which may comprise at least one oxygen atom as a link; a —C(═O)OR$^7$ group which may be bonded via a linear or branched $C_{1-3}$ alkylene group;

$R^2$ represents hydrogen; a linear or branched unsubstituted $C_{1-5}$ alkyl group which, as a link, may comprise at least one oxygen atom or may comprise at least one sulfur atom; a phenyl or naphthyl group, which may be monosubstituted or polysubstituted by the same or different substituents selected from the group consisting of F, Cl, Br, CN, NO$_2$, $C_{1-5}$ alkyl, $C_{1-5}$ alkoxy, —C(═O)C$_{1-5}$ alkyl, —C(═O)O—C$_{1-5}$ alkyl, —S(═O)$_2$—C$_{1-6}$ alkyl, —C(═O)C$_{1-5}$ perfluoroalkyl, —CF$_3$, CHF$_2$, and CH$_2$F and which may be bonded via a —(CH$_2$) bridge, a —(CH$_2$)$_2$— bridge, a —(CH$_2$)$_3$— bridge or a —(CH$_2$)$_2$—O— bridge;

$R^4$ represents an —$NR^{10}R^{11}$ group; a linear or branched unsubstituted $C_{1-4}$ alkyl group which may comprise, as a link, at least one oxygen atom which may comprise, as a link, at least one sulfur atom; a cyclic group selected from furyl (furanyl), thienyl (thiophenyl), phenyl, naphthyl, and 1,2,3,4-tetrahydroisoquinoline, where the cyclic group may in each case be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and the cyclic group may be bonded via a —$(CH_2)_2$— or —$(CH_2)_3$ bridge; an unsubstituted $C_5$ or $C_3$ cycloaliphatic group which may be at least monosubstituted by an oxo group and which may comprise at least one heteroatom as a ring member, which may be bonded via a —$(CH_2)$ bridge, a —$(CH_2)_2$— bridge, or a —$(CH_2)_3$— bridge and which may be bridged by a —$(C(CH_3)_2)$— group;

$R^5$ represents a linear or branched $C_{1-5}$ alkyl group which may comprise at least one oxygen atom and which may comprise at least one sulfur atom; a linear or branched $C_{2-5}$ alkenyl group which may comprise at least one oxygen atom and which may comprise at least one sulfur atom; a linear or branched $C_{2-5}$ alkynyl group which may comprise at least one oxygen atom and which may comprise at least one sulfur atom, a cyclic group selected from the group consisting of furyl (furanyl), thienyl (thiophenyl), phenyl, and naphthyl, wherein the cyclic radical may in each case be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perflouroalkyl, —$CF_3$, $CHF_2$, and $CH_2F$ and the cyclic radical may be bonded via a —$(CH_2)$ bridge, a —$(CH(CH_3))$ bridge, a —$(CH_2)_2$— bridge or a —$(CH_2)_3$ bridge; an unsubstituted $C_4$, $C_5$ or $C_6$ cycloaliphatic group which may comprise at least one oxygen atom as a ring member, and which may be bonded over a —$(CH_2)$ bridge, a —$(CH(CH_3))$ bridge, a —$(CH_2)_2$— bridge or a —$(CH_2)_3$ bridge; a —C(=O)O—$R^8$ group or a —C(=O)O$R^9$ group that may be bonded via a —$(CH_2)$ bridge, a —$(CH(CH_3))$ bridge, a —$(CH_2)_2$— bridge or a —$(CH_2)_3$— bridge;

$R^6$ represents a phenyl group, which phenyl group may be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and which phenyl group may be bonded via a —$(CH_2)$ bridge, a —$(CH(CH_3))$ bridge, a —$(CH_2)_2$— bridge, or a —$(CH_2)_3$— bridge; an unsubstituted $C_5$- or $C_6$-cycloaliphatic group, which may be bonded via a $(CH_2)$ bridge, a —$(CH(CH_3))$ bridge, a —$(CH_2)_2$— bridge, or a —$(CH_2)_3$— bridge;

and $R^7$, $R^8$, $R^9$, and $R^{10}$, $R^{11}$, independently represent a linear or branched methyl, ethyl, n-propyl, or isopropyl group.

7. The compound of claim 1, wherein $R^1$ represents hydrogen, a linear or branched unsubstituted $C_{1-4}$ alkyl group, a linear or branched unsubstituted $C_{2-3}$ alkenyl group, a linear or branched unsubstituted $C_{2-3}$ alkynyl group, a phenyl group or naphthyl group, any of which groups may be bonded via a —$(CH_2)$ bridge, a —$(CH_2)_2$— bridge, a —$(CH_2)_3$— bridge or a —$(CH_2)_2$—O— bridge and may be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perflouroalkyl, —$CF_3$, $CHF_2$, and $CH_2F$; or a —C(=O)O$R^7$ radical which may be bonded via a —$(CH_2)$ group;

$R^2$ represents hydrogen; a linear or branched unsubstituted $C_{1-5}$ alkyl group which, as a link, may comprise at least one sulfur atom; a phenyl group, wherein the phenyl group may be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and which may be bonded via a —$(CH_2)$ bridge;

$R^4$ represents an —$N(CH_3)_2$ group; a linear or branched unsubstituted $C_{1-4}$ alkyl group; a cyclic group selected from thienyl (thiophenyl), phenyl, and 1,2,3,4-tetrahydroisoquinoline, wherein the cyclic group may, in each case, be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and the cyclic group may be can be bonded over a —$(CH_2)$ bridge; an unsubstituted $C_5$ or $C_{1-6}$ cycloaliphatic group which may be at least monosubstituted by an oxo group and which may be bonded via a —$(CH_2)$ bridge which may be bridged by a —$(C(CH_3)_2)$— group, $R^5$ represents a linear or branched unsubstituted $C_{1-3}$ alkyl group which may comprise at least one oxygen atom; a linear or branched unsubstituted $C_{2-3}$ alkenyl group, a linear or branched unsubstituted $C_{2-3}$ alkynyl group, a phenyl group wherein the phenyl group may be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and the phenyl group may be bonded via a $(CH_2)$ bridge, a —$(CH(CH_3))$ bridge, a —$(CH_2)_2$— bridge or a —$(CH_2)_3$ bridge; an unsubstituted $C_5$ or $C_6$ cycloaliphatic group which may comprise at least one oxygen atom as a ring member and which may be bonded via a —$(CH_2)$ bridge, a —$(CH(CH_3))$ bridge, a —$(CH_2)_2$— bridge or a —$(CH_2)_3$ bridge; a C(=O)O—$C_2H_5$ group or for a —C(=O)O—$R^9$ group which may be bonded via a —$(CH_2)$ bridge, a —$(CH(CH_3))$ bridge, a —$(CH_2)_2$— bridge or a —$(CH_2)_3$ bridge;

and $R^6$ represents a phenyl group, which phenyl group may be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and which phenyl group may be bonded via a $(CH_2)$ bridge or a —$(CH_2)_2$— bridge; a cyclohexyl group, which may be bonded via a $(CH_2)$ bridge or a —$(CH_2)_2$ bridge.

8. The compound of claim 1, wherein $R^1$ represents hydrogen; an alkyl moiety selected from the group consisting of methyl, ethyl, n-propyl, isopropyl, n-butyl, isobutyl, sec-butyl, and tert-butyl; an alkenyl moiety selected from the group consisting of vinyl and allyl; a propynyl group; a 1-naphthyl group, or a 2-naphthyl group, where any cyclic group may be bonded via a —($CH_2$)— bridge, a —($CH_2$)$_2$— bridge, a —($CH_2$)$_2$— bridge, or a —($CH_2$)$_2$—O— bridge and may be mono-substituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perflouroalkyl, —$CF_3$, $CHF_2$, and $CH_2F$; a —C(=O)$OR^7$ group which may be bonded via a ($CH_2$) group;

$R^2$ represents hydrogen; a linear or branched unsubstituted alkyl group which may comprise at least one sulfur atom and which is selected from the group consisting of methyl, ethyl, n-propyl, isopropyl, n-butyl, isobutyl, sec-butyl, tert-butyl, and 2-methylsulfanylethyl; a phenyl group or benzyl group, each of which may be unsubstituted or monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perflouroalkyl, —$CF_3$, $CHF_2$, and $CH_2F$;

$R^3$ represents an S(=O)$_2$—$R^4$ group, a —C(=S)NH—$R^5$ group or a —C(=O)NH—$R^6$ group, $R^4$ represents a N—($CH_3$)$_2$ group; an alkyl group selected from the group consisting of methyl, ethyl, n-propyl, isopropyl, n-butyl, isobutyl, sec-butyl, tert-butyl; a thienyl (thiophenyl) group, phenyl group, or 1,2,3,4-tetrahydroisoquinoline group, wherein each cyclic group may be unsubstituted or monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and which cyclic group may be bonded via a ($CH_2$) bridge; or a 7,7-dimethyl-2-oxobicyclo[2.2.1]hept-1-ylmethyl group;

$R^5$ represents a moiety selected from the group consisting of methyl, ethyl, n-propyl, isopropyl, n-butyl, isobutyl, sec-butyl, tert-butyl, and 2-methoxyethyl; an alkenyl moiety selected from the group consisting of vinyl and allyl; a propynyl group; a phenyl group, wherein the phenyl group may be monosubstituted or polysubstituted by the same or different substituents selected from the group consisting of F, Cl, Br, CN, $NO_2$, $C_{1-5}$ alkyl, $C_{1-5}$ alkoxy, —C(=O)$C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and the phenyl group may be bonded via a ($CH_2$) bridge, a —(CH($CH_3$))— bridge, a —($CH_2$)$_2$— bridge, or a —($CH_2$)$_3$ bridge; a cyclohexyl or tetrahydrofuryl group, which may be bonded via a ($CH_2$) bridge; a C(=O)O—$C_2H_5$ group or a —C(=O)O—$C_2H_5$ group which may be bonded via a ($CH_2$) bridge, a —(CH($CH_3$))— bridge, a —($CH_2$)$_2$— bridge, or a —($CH_2$)a bridge;

$R^6$ represents phenyl, which may be unsubstituted or monosubstituted or polysubstituted by the same or different substituents selected from the group consisting of F, Cl, Br, CN, $NO_2$, $C_{1-5}$ alkyl, $C_{1-5}$ alkoxy, —C(=O) $C_{1-5}$ alkyl, —C(=O)O—$C_{1-5}$ alkyl, —S(=O)$_2$—$C_{1-6}$ alkyl, —C(=O)$C_{1-5}$ perfluoroalkyl, —$CF_3$, $CHF_2$, and $CH_2F$ and the phenyl may be bonded via a ($CH_2$) bridge or a —($CH_2$)$_2$— bridge; a cyclohexyl group, which may be bonded via a ($CH_2$) bridge or a —($CH_2$)$_2$ bridge, $R^7$, $R^8$, $R^9$, $R^{10}$, and $R^{11}$ each independently represent a linear or branched $C_{1-5}$ alkyl group, a linear or branched $C_{2-5}$ alkenyl group or a linear or branched $C_{2-5}$ alkynyl group.

9. The compound of claim 1, wherein $R^7$, $R^8$, $R^9$, $R^{10}$, and $R^{11}$ each independently represent linear or branched methyl, ethyl, n-propyl or isopropyl.

10. The compound of claim 1, wherein $R^1$ represents hydrogen;
a $C_{1-10}$ alkyl group, $C_{2-10}$ alkynyl group or $C_{2-10}$ alkenyl group which may be linear or branched, and may be substituted;
a 5-membered to 14-membered aryl or heteroaryl group which may be substituted;
—($CH_2$)$_{aa}$—C(=O)—O—$R^7$ wherein aa is 1, 2, 3, 4 or 5; or
—($CH_2$)—$U_a$—($CH_2$)$_b$—$V_c$—($CH_2$)$_d$—$R^{12}$ wherein a is 0 or 1, b is 0 or 1, c is 0 or 1 and d is 0 or 1, wherein U and V each independently represent O, S, NH, N($CH_3$) or N($C_2H_5$);

$R^2$ represents hydrogen;
a $C_{1-10}$ alkyl group, $C_{2-10}$ alkynyl group or $C_{2-10}$ alkenyl group which may be linear or branched, and may be substituted;
a 5-membered to 14-membered aryl or heteroaryl group which may be substituted;
—($CH_2$)—$W_e$—($CH_2$)$_f$—$X_g$—($CH_2$)$_h$—$R^{13}$ in which e is 0 or 1, f is 0 or 1, g is 0 or 1 and h is 0 or 1, wherein W and X each independently represent O, S, NH, N($CH_3$) or N($C_2H_5$);

$R^3$ represents a —S(=O)$_2$—$R^4$ group; a —C(=S)—NH—$R^5$ group or a —C(=O)—NH—$R^6$ group;

$R^4$ represents a —$NR^{10}R^{11}$;
a $C_{1-10}$ alkyl group, $C_{2-10}$ alkynyl group or $C_{2-10}$ alkenyl group which may be linear or branched, and may be substituted;
an unsaturated or saturated, 3-membered, 4-membered, 5-membered, 6-membered, 7-membered, 8-membered, or 9-membered cycloaliphatic which may be substituted, and which may be bridged by one or two linear or branched, $C_{1-5}$ alkylene groups which may be substituted;
a 5-membered to 14-membered aryl or heteroaryl radical, which may be substituted and which may be condensed with a saturated or unsaturated, monocyclic ring system which may be substituted; or
—($CH_2$)—$Y_k$—($CH_2$)$_m$-$Z_n$-($CH_2$)$_p$—$R^{14}$ wherein k is 0 or 1, m is 0 or 1, n is 0 or 1 and p is 0 or 1, and wherein Y and Z each independently represent O, S, NH, N($CH_3$) or N($C_2H_5$);

$R^5$ represents a $C_{1-10}$ alkyl group, $C_{2-10}$ alkynyl group or $C_{2-10}$ alkenyl group which may be linear or branched, and may be substituted;
an unsaturated or saturated, 3-membered, 4-membered, 5-membered, 6-membered, 7-membered, 8-membered, or 9-membered cycloaliphatic group which may be substituted;
a 5-membered to 14-membered aryl or heteroaryl group which may be substituted;
—($CHR^{15}$)-$A_q$-($CH_2$)$_r$—$B_s$—($CH_2$)$_t$—$R^{16}$ wherein q is 0 or 1, r is 0 or 1, s is 0 or 1 and t is 0 or 1, wherein A and B each independently represent O, S, NH, N($CH_3$) or N($C_2H_5$);
—C(=O)—$OR^8$;
—($CHR^{17}$)—($CH_2$)$_v$—C(=O)—$OR^9$, wherein v is 0, 1, 2, or 3;

$R^6$ represents an unsaturated or saturated, 3-membered, 4-membered, 5-membered, 6-membered, 7-membered, 8-membered, or 9-membered cycloaliphatic group which may be substituted;
  a 5-membered to 14-membered aryl or heteroaryl group which may be substituted;
  —$(CH_2)$-$D_w$-$(CH_2)_x$-$E_y$-$(CH_2)_z$—$R^{18}$ in which w is 0 or 1, x is 0 or 1, y is 0 or 1 and z is 0 or 1, wherein D and E each independently represent O, S, NH, N($CH_3$) or N($C_2H_5$);
$R^7$, $R^8$, $R^9$, $R^{10}$ and $R^{11}$ each independently
  represent a $C_{1-10}$ alkyl group, $C_{2-10}$ alkynyl group or $C_{2-10}$ alkenyl group which may be linear or branched, and may be substituted
$R^{12}$ and $R^{13}$ each independently
  represent a $C_{1-10}$ alkyl group, $C_{2-10}$ alkynyl group or $C_{2-10}$ alkenyl group which may be linear or branched, and may be substituted;
  a 5-membered to 14-membered aryl or heteroaryl radical which may be substituted;
$R^{14}$ represents a $C_{1-10}$ alkyl group, $C_{2-10}$ alkynyl group or $C_{2-10}$ alkenyl group which may be linear or branched, and may be substituted;
  an unsaturated or saturated, 3-membered, 4-membered, 5-membered, 6-membered, 7-membered, 8-membered, or 9-membered cycloaliphatic radical, which may be substituted and which may be bridged by one or two linear or branched, $C_{1-5}$ alkylene groups which may be substituted;
  a 5-membered to 14-membered aryl or heteroaryl radical which may be substituted and which may be condensed with a saturated or unsaturated, monocyclic ring system which may be substituted;
$R^{15}$ represents hydrogen; or
  a $C_{1-10}$ alkyl group, $C_{2-10}$ alkynyl group or $C_{2-10}$ alkenyl group which may be linear or branched, and may be substituted;
$R^{16}$ represents a $C_{1-10}$ alkyl group, $C_{2-10}$ alkynyl group or $C_{2-10}$ alkenyl group which may be linear or branched, and may be substituted;
  an unsaturated or saturated, 3-membered, 4-membered, 5-membered, 6-membered, 7-membered, 8-membered, or 9-membered cycloaliphatic group which may be substituted;
  a 5-membered to 14-membered aryl or heteroaryl group which may be substituted;
$R^{17}$ represents a $C_{1-10}$ alkyl group, $C_{2-10}$ alkynyl group or $C_{2-10}$ alkenyl group which may be linear or branched, and may be substituted;
and
$R^{18}$ represents an unsaturated or saturated, 3-membered, 4-membered, 5-membered, 6-membered, 7-membered, 8-membered, or 9-membered cycloaliphatic group which may be substituted;
  a 5-membered to 14-membered aryl or heteroaryl group which may be substituted;
wherein
  the $C_{1-10}$ alkyl groups are unsubstituted or may each be substituted by 1, 2, 3, 4 or 5 substituents each independently selected from the group consisting of F, Cl, Br, I, —CN, —$NO_2$, —OH, —SH, —$NH_2$ and —N($C_{1-5}$ alkyl)($C_{1-5}$ alkyl);
  the $C_{2-10}$ alkenyl groups are unsubstituted or may be substituted by 1, 2, 3, 4 or 5 substituents each independently selected from the group consisting of F, Cl, Br, I, —CN, —$NO_2$, —OH, —SH, —$NH_2$ and —N($C_{1-5}$ alkyl)($C_{1-5}$ alkyl);
  the $C_{2-10}$ alkynyl groups are unsubstituted or may be substituted by 1, 2, 3, 4 or 5 substituents each independently selected from the group consisting of F, Cl, Br, I, —CN, —$NO_2$, —OH, —SH, —$NH_2$ and —N($C_{1-5}$ alkyl)($C_{1-5}$ alkyl);
  the $C_{1-5}$ alkylene groups are unsubstituted or may be substituted by 1, 2, 3, 4 or 5 substituents each independently selected from the group consisting of F, Cl, Br, —OH, —SH, —$NH_2$, —CN, $NO_2$ and phenyl,
  the cycloaliphatic groups are unsubstituted or may be substituted by 1, 2, 3, 4 or 5 substituents each independently selected from the group consisting of oxo (=O), thioxo (=S), F, Cl, Br, I, —CN, —$CF_3$, —$SF_5$, —OH, —O—$C_{1-5}$ alkyl, —$NH_2$, —$NO_2$, —O—$CF_3$, —S—$CF_3$, —SH, —S—$C_{1-5}$ alkyl, —$C_{1-5}$ alkyl, —C(=O)—H, —C(=O)—$C_{1-5}$ alkyl, —C(=O)—$C_{1-5}$ perfluoroalkyl, —C(=O)—OH, —C(=O)—O—$C_{1-5}$ alkyl, —($CH_2$)—C(=O)—OH, —($CH_2$)—C(=O)—O—$C_{1-5}$ alkyl, —NH—$C_{1-5}$ alkyl, —N($C_{1-5}$ alkyl)$_2$, —($CH_2$)-benzo[b]furanyl, —O-phenyl, —O-benzyl, phenyl, benzyl, naphthyl and —($CH_2$)-naphthyl, while the cyclic moiety of each of the —O-phenyl, —O-benzyl, phenyl, —($CH_2$)-benzo[b]furanyl, benzyl, naphthyl, and —($CH_2$)-naphthyl groups may be substituted by 1, 2, 3, 4 or 5 substituents each independently selected from the group consisting of F, Cl, Br, —OH, —$CF_3$, —$SF_5$, —CN, —$NO_2$, —O—$C_{1-5}$ alkyl, —$C_{1-5}$ alkyl, —O—$CF_3$, —S—$CF_3$, phenyl and —O-benzyl,
  and the cycloaliphatic groups may each independently comprise one or more heteroatoms selected from the group consisting of oxygen, nitrogen, and sulfur; the ring of the aforementioned monocyclic ring systems are unsubstituted or may be substituted by 1, 2, 3, 4 or 5 substituents each independently selected from the group consisting of oxo (=O), thioxo (=S), F, Cl, Br, I, —CN, —$CF_3$, —$SF_5$, —OH, —O—$C_{1-5}$ alkyl, —O—$C_{2-5}$ alkenyl, —$NH_2$, —$NO_2$, —O—$CF_3$, —O—$CHF_2$, —O—$CH_2F$, —S—$CF_3$, —S—$CHF_2$, —S—$CH_2F$, —SH, —S—$C_{1-5}$ alkyl, —$C_{1-5}$ alkyl, —C(=O)—OH, —C(=O)—O—$C_{1-5}$ alkyl, —O—C(=O)—$C_{1-5}$ alkyl, —O—C(=O)-phenyl, —($CH_2$)—O—C(=O)—$C_{1-5}$ alkyl, —($CH_2$)—O—C(=O)-phenyl, —NH—$C_{1-5}$ alkyl, —N($C_{1-5}$ alkyl)$_2$, —NH—C(=O)—O—$C_{1-5}$ alkyl, —NH—C(=O)—$C_{1-5}$ alkyl, —C(=O)—H, —C(=O)—$C_{1-5}$ alkyl, —C(=O)—$C_{1-5}$ perfluoroalkyl, —C(=O)—$NH_2$, —C(=O)—NH—$C_{1-5}$ alkyl, C(=O)—N—($C_{1-5}$ alkyl)$_2$, —S(=O)$_2$—$NH_2$, —S(=O)$_2$—NH—$C_{1-5}$ alkyl, —S(=O)$_2$—NH-phenyl, —S(=O)$_2$—$C_{1-5}$ alkyl, —($CH_2$)-benzo[b]furanyl, —O-phenyl, —S-phenyl, —S-benzyl, —O-benzyl, phenyl and benzyl, and the cyclic moiety of each of the groups —O—C(=O)-phenyl, —($CH_2$)—O—C(=O)-phenyl, —S(=O)$_2$—NH-phenyl, —O-phenyl, —S-phenyl, —S-benzyl, —O-benzyl, phenyl, —($CH_2$)-benzo[b]furanyl and benzyl may be substituted by 1, 2, 3, 4 or 5 substituents each independently selected from the group consisting of F, Cl, Br, —OH, —$CF_3$, —$SF_5$, —CN, —$NO_2$, —O—$C_{1-5}$ alkyl, —$C_{1-5}$ alkyl, —O—$CF_3$, —S—$CF_3$, phenyl and —O-benzyl,
  and the ring of the monocyclic ring systems is 5-membered, 6-membered, or 7-membered and may comprise 1, 2, 3, 4 or 5 heteroatoms as ring members, which are independently selected from the group consisting of oxygen, nitrogen, and sulfur;
  and the aryl or heteroaryl groups are unsubstituted or may be substituted by 1, 2, 3, 4 or 5 substituents each independently selected from the group consisting of F, Cl, Br, I, —CN, —CF$_3$, —SF$_5$, —OH, —O—C$_{1-5}$ alkyl, —O—C$_{2-5}$ alkenyl, —NH$_2$, —NO$_2$, —O—CF$_3$, —O—CHF$_2$, —O—CH$_2$F, —S—CF$_3$, —S—CHF$_2$, —S—CH$_2$F, —SH, —S—C$_{1-5}$ alkyl, —C$_{1-5}$ alkyl, —C(=O)—OH, —C(=O)—O—C$_{1-5}$ alkyl, —O—C(=O)—C$_{1-5}$ alkyl, —O—C(=O)-phenyl, —(CH$_2$)—O—C(=O)—C$_{1-5}$ alkyl, —(CH$_2$)—O—C(=O)-phenyl, —NH—C$_{1-5}$ alkyl, —N(C$_{1-5}$ alkyl)$_2$, —NH—C(=O)—O—C$_{1-5}$ alkyl, —NH—C(=O)—C$_{1-5}$ alkyl, —C(=O)—H, —C(=O)—C$_{1-5}$ alkyl, —C(=O)—C$_{1-5}$ perflouroalkyl, —C(=O)—NH$_2$, —C(=O)—NH—C$_{1-5}$ alkyl, C(=O)—N—(C$_{1-5}$ alkyl)$_2$, —S(=O)$_2$—NH$_2$, —S(=O)$_2$—NH—C$_{1-5}$ alkyl, —S(=O)$_2$—NH-phenyl, —S(=O)$_2$—C$_{1-5}$ alkyl, —(CH$_2$)-benzo[b]furanyl, —O-phenyl, —S-phenyl, —S-benzyl, —O-benzyl, phenyl and benzyl, where the cyclic moiety of each of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl, and benzyl may be substituted by 1, 2, 3, 4 or 5 substituents each independently selected from the group consisting of F, Cl, Br, —OH, —CF$_3$, —SF$_5$, —CN, —NO$_2$, —O—C$_{1-5}$ alkyl, —C$_{1-5}$ alkyl, —O—CF$_3$, —S—CF$_3$, phenyl and —O-benzyl;

and the heteroaryl groups may comprise 1, 2, 3, 4 or 5 heteroatom as ring member, which are independently selected from the group consisting of oxygen, nitrogen, and sulfur.

11. The compound of claim 10, wherein

R$^1$ represents hydrogen;

a moiety selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each of these moieties may be substituted by 1, 2, 3, 4 or 5 substituents each independently selected from the group consisting of F, Cl, Br, I, —CN, —NO$_2$, —OH, —SH, —NH$_2$, —N(CH$_3$)$_2$, —N(C$_2$H$_5$)$_2$ and —N(CH$_3$)(C$_2$H$_5$);

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl and chromanyl, wherein each of these moieties may be substituted by 1, 2, 3, 4 or 5 substituents each independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CHisCH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)-H, —C(=O)—CH$_3$, —C(=O)—C$_2$H$_5$, —C(=O)—CF$_3$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —S(=O)$_2$—NH-phenyl, —S(=O)$_2$—CH$_3$, —S(=O)$_2$—C$_2$H$_5$, —(CH$_2$)-benzo[b]furanyl, —O-phenyl, —S-phenyl, —S-benzyl, —O-benzyl, phenyl and benzyl, wherein the cyclic moiety of each of the groups —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl and benzyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, isobutyl, tert-butyl, —O—CF$_3$, —S—CF$_3$, phenyl and —O-benzyl, —(CH$_2$)$_{aa}$—C(=O)—O—R$^7$ in which aa is 1, 2, 3, 4 or 5;

(CH$_2$)—R$^{12}$, —(CH$_2$)—(CH$_2$)—R$^{12}$, —(CH$_2$)—O—R$^{12}$, —(CH$_2$)—S—R$^{12}$, —(CH$_2$)—N(CH$_3$)—R$^{12}$, —(CH$_2$)—(CH$_2$)—(CH$_2$)—R$^{12}$, —(CH$_2$)—(CH$_2$)—O—R$^{12}$, —(CH$_2$)—(CH$_2$)—S—R$^{12}$, —(CH$_2$)—(CH$_2$)—NH—R$^{12}$, —(CH$_2$)—(CH$_2$)—N(CH$_3$)—R$^{12}$, —(CH$_2$)—(CH$_2$)—O—(CH$_2$)—R$^{12}$, —(CH$_2$)—(CH$_2$)—S—(CH$_2$)—R$^{12}$ or —(CH$_2$)—(CH$_2$)—N(CH$_3$)—R$^{12}$;

R$^2$ represents hydrogen;

a moiety selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each moiety may be substituted by 1, 2, 3, 4 or 5 substituents each independently selected from the group consisting of F, Cl, Br, I, —CN, —NO$_2$, —OH, —SH, —NH$_2$, —N(CH$_3$)$_2$, —N(C$_2$H$_5$)$_2$, and —N(CH$_3$)(C$_2$H$_5$);

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl and chromanyl, wherein each moiety may be substituted by 1, 2, 3, 4 or 5 substituents each independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CHisCH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—CF$_3$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —S(=O)$_2$—NH-phenyl, —S(=O)$_2$—CH$_3$, —S(=O)$_2$—C$_2$H$_5$, —(CH$_2$)-benzo[b]furanyl, —O-phenyl, —S-phenyl, —S-benzyl, —O-benzyl, phenyl and benzyl, wherein the cyclic moiety of each of —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl and benzyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, Isobutyl, tert-butyl, —O—CF$_3$, —S—CF$_3$, phenyl and —O-benzyl, —(CH$_2$)—R$^{13}$, —(CH$_2$)—(CH$_2$)—R$^{13}$, (CH$_2$)—O—R$^{13}$, —(CH$_2$)—S—R$^{13}$, —(CH$_2$)—N(CH$_3$)—R$^{13}$, —(CH$_2$)—(CH$_2$)—(CH$_2$)—R$^{13}$, —(CH$_2$)—(CH$_2$)—O—R$^{13}$, —(CH$_2$)—(CH$_2$)—S—R$^{13}$, —(CH$_2$)—(CH$_2$)—NH—R$^{13}$, —(CH$_2$)—(CH$_2$)—N(CH$_3$)—R$^{13}$, —(CH$_2$)—(CH$_2$)—O—(CH$_2$)—R$^{13}$, —(CH$_2$)—(CH$_2$)—S—(CH$_2$)—R$^{13}$ or —(CH$_2$)—(CH$_2$)—N(CH$_3$)—R$^{13}$;

R$^3$ represents an —S(=O)$_2$—R$^4$ group, a —C(=S)—NH—R$^5$ group or a —C(=O)—NH—R$^6$ group, R$^4$ represents —NR$^{10}$R$^{11}$;

a moiety selected from the group consisting of methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each moiety may be substituted by 1, 2, 3, 4 or 5 substituents each independently selected from the group consisting of F, Cl, Br, I, —CN, —NO$_2$, —OH, —SH, —NH$_2$, —N(CH$_3$)$_2$, —N(C$_2$H$_5$)$_2$ and —N(CH$_3$)(C$_2$H$_5$);

a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, dithiolanyl, adamantyl and 7,7-dimethyl-bicyclo[2.2.1]heptyl, wherein the (hetero)cycloaliphatic moiety may be substituted by 1, 2, 3, 4 or 5 substituents each independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, S—CH$_3$, —S—C$_2$H$_5$, —S—C(CH$_3$)$_3$, methyl, ethyl, n-propyl, isopropyl, n-butyl, sec-butyl, isobutyl, tert-butyl, —C(=O)—H, —C(=O)—CH$_3$, —C(=O)—C$_2$H$_5$, —C(=O)—OH, —C(=O)—O—CH$_3$, —C(=O)—O—C$_2$H$_5$, —C(=O)—O—C(CH$_3$)$_3$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —(CH$_2$)-benzo[b]furanyl, —O-phenyl, —O-benzyl, phenyl, benzyl, naphthyl and (CH$_2$)-naphthyl, therein the cyclic moiety of each of —O-phenyl, —O-benzyl, phenyl, —(CH$_2$)-benzo[b]furanyl, benzyl, naphthyl and —(CH$_2$)-naphthyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, methyl, ethyl, n-propyl, isopropyl, n-butyl, sec-butyl, isobutyl, tert-butyl, —O—CF$_3$, —S—CF$_3$, phenyl and —O-benzyl;

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl, chromanyl and (1,2,3,4)-tetrahydroquinolynyl, wherein each moiety may be substituted by 1, 2, 3, 4 or 5 substituents each independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CHisCH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, isobutyl, tert-butyl, (1,1)-dimethylpropyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—CF$_3$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —S(=O)$_2$—NH-phenyl, —S(=O)$_2$—CH$_3$, —S(=O)$_2$—C$_2$H$_5$, —(CH$_2$)-benzo[b]furanyl, —O-phenyl, —S-phenyl, —S-benzyl, —O-benzyl, phenyl and benzyl, wherein the cyclic moiety of each of —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl and benzyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C (CH₃)₃, methyl, ethyl, n-propyl, isopropyl, n-butyl, sec-butyl, isobutyl, tert-butyl, —O—CF₃, —S—CF₃, phenyl and —O-benzyl;
—(CH₂)—R¹⁴, —(CH₂)—(CH₂)—R¹⁴, —(CH₂)—O—R¹⁴, —(CH₂)—S—R¹⁴, —(CH₂)—N(CH₃)—R¹⁴, —(CH₂)—(CH₂)—(CH₂)—R¹⁴, —(CH₂)—(CH₂)—O—R¹⁴, —(CH₂)—(CH₂)—S—R¹⁴, —(CH₂)—(CH₂)—NH—R¹⁴, —(CH₂)—(CH₂)—N(CH₃)—R¹⁴, —(CH₂)—(CH₂)—O—(CH₂)—R¹⁴, —(CH₂)—(CH₂)—S—(CH₂)—R¹⁴ or —(CH₂)—(CH₂)—N(CH₃)—R¹⁴;

$R^5$ represents a moiety selected from the group consisting of methyl, ethyl, n-propyl, isopropyl, n-butyl, sec-butyl, Isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)(C₂H₅)—(CH₂)—(CH₂)—(CH₂)—(CH₃), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each moiety may be substituted by 1, 2, 3, 4 or 5 substituents each independently selected from the group consisting of F, Cl, Br, I, —CN, —NO₂, —OH, —SH, —NH₂, —N(CH₃)₂, —N(C₂H₅)₂ and —N(CH₃)(C₂H₅);

a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl and dithiolanyl, wherein the (hetero)cycloaliphatic moiety may be substituted by 1, 2, 3, 4 or 5 substituents each independently selected from the group consisting of oxo (=O), thioxo (=S), F, Cl, Br, I, —CN, —CF₃, —SF₅, —OH, —O—CH₃, —O—C₂H₅, —O—C(CH₃)₃, —NH₂, —NO₂, —O—CF₃, —S—CF₃, —SH, S—CH₃, —S—C₂H₅, —S—C(CH₃)₃, methyl, ethyl, n-propyl, isopropyl, n-butyl, sec-butyl, isobutyl, tert-butyl, —C(=O)—H, —C(=O)—CH₃, —C(=O)—C₂H₅, —C(=O)—OH, —C(=O)—O—CH₃, —C(=O)—O—C₂H₅, —C(=O)—O—C(CH₃)₃, —(CH₂)—C(=O)—OH, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), —(CH₂)-benzo[b]furanyl, —O-phenyl, —O-benzyl, phenyl, benzyl, naphthyl and —(CH₂)-naphthyl, and wherein the cyclic moiety of each of —O-phenyl, —O-benzyl, phenyl, —(CH₂)-benzo[b]furanyl, benzyl, naphthyl and —(CH₂)-naphthyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, methyl, ethyl, n-propyl, isopropyl, n-butyl, sec-butyl, isobutyl, tert-butyl, —O—CF₃, —S—CF₃, phenyl and O-benzyl;

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl and chromanyl, wherein each moiety may be substituted by 1, 2, 3, 4 or 5 substituents each independently selected from the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CHisCH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, isobutyl, tert-butyl, (1,1)-dimethylpropyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)₂, —N(H)(CH₃), —N(H)(C₂H₅), —NH—C(=O)—O—CH₃, —NH—C(=O)—O—C₂H₅, —NH—C(=O)—CH₃, —NH—C(=O)—C₂H₅, —C(=O)—H, —C(=O)—CH₃, —C(=O)—C₂H₅, —C(=O)—CF₃, —C(=O)—NH₂, —C(=O)—NH—CH₃, —C(=O)—NH—C₂H₅, —S(=O)₂—NH₂, —S(=O)₂—NH—CH₃, —S(=O)₂—NH—C₂H₅, —S(=O)₂—NH-phenyl, —S(=O)₂—CH₃, —S(=O)₂—C₂H₅, —(CH₂)-benzo[b]furanyl, —O-phenyl, —S-phenyl, —S-benzyl, —O-benzyl, phenyl and benzyl, wherein the cyclic moiety of each of —O—C(=O)-phenyl, —(CH₂)—O—C(=O)-phenyl, —S(=O)₂—NH-phenyl, —O-phenyl, —S-phenyl, —S-benzyl, —O-benzyl, phenyl, —(CH₂)-benzo[b]furanyl, and benzyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, isobutyl, tert-butyl, —O—CF₃, —S—CF₃, phenyl and —O-benzyl;

—(CHR¹⁵)—R¹⁶, —(CHR¹⁵)—(CH₂)—R¹⁶, —(CHR¹⁵)—O—R¹⁶, —(CHR¹⁵)—S—R¹⁶, —(CHR¹⁵)—N(CH₃)—R¹⁶, —(CHR¹⁵)—(CH₂)—(CH₂)—R¹⁶, —(CHR¹⁵)—(CH₂)—O—R¹⁶, —(CHR¹⁵)—(CH₂)—S—R¹⁶, —(CHR¹⁵)—(CH₂)—NH—R¹⁶, —(CHR¹⁵)—(CH₂)—N(CH₃)—R¹⁶, —(CHR¹⁵)—(CH₂)—O—(CH₂)—R¹⁶, —(CHR¹⁵)—(CH₂)—S—(CH₂)—R¹⁶ or —(CHR¹⁵)—(CH₂)—N(CH₃)—R¹⁶;

a —C(=O)—OR⁸ group;

a —(CHR¹⁷)—C(=O)—OR⁹ group or a —(CHR¹⁶)—(CH₂)—C(=O)—OR⁹ group;

$R^6$ represents a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl and dithiolanyl, wherein the (hetero)cycloaliphatic moiety may be substituted by 1, 2, 3, 4 or 5 substituents each independently selected from the group consisting of oxo (=O), thioxo (=S), F, Cl, Br, I, —CN, —CF₃, —SF₅, —OH, —O—OH₃, —O—C₂H₅, —O—C(CH₃)₃, —NH₂, —NO₂, —O—CF₃, —S—CF₃, —SH, S—CH₃, —S—C₂H₅, —S—C(CH₃)₃, methyl, ethyl, n-propyl, isopropyl, n-butyl, sec-butyl, Isobutyl, tert-butyl, —C(=O)—H, —C(=O)—CH₃, —C(=O)—C₂H₅, —C(=O)—OH, —C(=O)—O—CH₃, —C(=O)—O—C₂H₅, —C(=O)—O—C(CH₃)₃, —(CH₂)—C (=O)—CH, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), —(CH₂)-benzo[b]furanyl, —O-phenyl, —O-benzyl, phenyl, benzyl, naphthyl and —(CH₂)-naphthyl which may be substituted, wherein the cyclic moiety of each of —O-phenyl, —O-benzyl, phenyl, —(CH₂)-benzo[b]furanyl, benzyl, naphthyl and —(CH₂)-naphthyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, methyl, ethyl, n-propyl, isopropyl, n-butyl, sec-butyl, Isobutyl, tert-butyl, —O—CF₃, —S—CF₃, phenyl and —O-benzyl;

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl and chromanyl, while each of moiety may be substituted by 1, 2, 3, 4 or 5 substituents each independently selected from the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CHisCH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, Isobutyl, tert-butyl, (1,1)-dimethylpropyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)₂, —N(H)(CH₃), —N(H)(C₂H₅), —NH—C(=O)—O—CH₃, —NH—C(=O)—O—C₂H₅, —NH—C(=O)—CH₃, —NH—C(=O)—C₂H₅, —C(=O)—H, —C(=O)—CH₃, —C(=O)—C₂H₅, —C(=O)—CF₃, —C(=O)—NH₂, —C(=O)—NH—CH₃, —C(=O)—NH—C₂H₅, —S(=O)₂—NH₂, —S(=O)₂—NH—CH₃, —S(=O)₂—NH—C₂H₅, —S(=O)₂—NH-phenyl, —S(=O)₂—CH₃, —S(=O)₂—C₂H₅, —(CH₂)-benzo[b]furanyl, —O-phenyl, —S-phenyl, —S-benzyl, —O-benzyl, phenyl and benzyl, wherein the cyclic moiety of each of —O—C(=O)-phenyl, —(CH₂)—O—C(=O)-phenyl, —S(=O)₂—NH-phenyl, —O-phenyl, —S-phenyl, —S-benzyl, —O-benzyl, phenyl, —(CH₂)-benzo[b]furanyl and benzyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, Isobutyl, tert-butyl, —O—CF₃, —S—CF₃, phenyl and —O-benzyl;

—(CH₂)—R¹⁸, —(CH₂)—(CH₂)—R¹⁸, —(CH₂)—O—R¹⁸, —(CH₂)—S—R¹⁸, —(CH₂)—N(CH₃)—R¹⁸, —(CH₂)—(CH₂)—(CH₂)—R¹⁸, —(CH₂)—(CH₂)—O—R¹⁸, —(CH₂)—O—R¹⁸, —(CH₂)—(CH₂)—S—R¹⁸, —(CH₂)—(CH₂)—NH—R¹⁸, —(CH₂)—(CH₂)—N(CH₃)—R¹⁸, —(CH₂)—(CH₂)—O—(CH₂)—R¹⁸, —(CH₂)—(CH₂)—S—(CH₂)—R¹⁸ or —(CH₂)—(CH₂)—N(CH₃)—R¹⁸;

R⁷, R⁸, R⁹, R¹⁰ and R¹¹ each independently represent
a moiety selected from the group consisting of methyl, ethyl, n-propyl, isopropyl, n-butyl, sec-butyl, Isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)—(C₂H₅)—(CH₂)—(CH₂)—(CH₂)—(CH₃), vinyl, 1-propenyl, 2-propenyl, 1-butenyl, 2-butenyl, 3-butenyl, 1-propynyl, 2-propynyl, 1-butynyl, 2-butynyl and 3-butynyl, and each moiety may be substituted by 1, 2, 3, 4 or 5 substituents each independently selected from the group consisting of F, Cl, Br, I, —CN, —NO₂, —OH, —SH, —NH₂, —N(CH₃)₂, —N(C₂H₅)₂ and —N(CH₃)(C₂H₅);

R¹² and R¹³ each independently represent
a moiety selected from the group consisting of methyl, ethyl, n-propyl, isopropyl, n-butyl, sec-butyl, Isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)(C₂H₅)—(CH₂)—(CH₂)—(CH₂)—(CH₃), vinyl, 1-propenyl, 2-propenyl, 1-butenyl, 2-butenyl, 3-butenyl, 1-propynyl, 2-propynyl, 1-butynyl, 2-butynyl and 3-butynyl, and each moiety may be substituted by 1, 2, 3, 4 or 5 substituents each independently selected from the group consisting of F, Cl, Br, I, —CN, —NO₂, —OH, —SH, —NH₂, —N(CH₃)₂, —N(C₂H₅)₂ and —N(CH₃)(C₂H₅);

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl and chromanyl, wherein each moiety may be substituted by 1, 2, 3, 4 or 5 substituents each independently selected from the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CHisCH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, Isobutyl, tert-butyl, (1,1)-dimethylpropyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)₂, —N(H)(CH₃), —N(H)(C₂H₅), —NH—C(=O)—O—CH₃, —NH—C(=O)—O—C₂H₅, —NH—C(=O)—CH₃, —NH—C(=O)—C₂H₅, —C(=O)—H, —C(=O)—CH₃, —C(=O)—C₂H₅, —C(=O)—CF₃, —C(=O)—NH₂, —C(=O)—NH—CH₃, —C(=O)—NH—C₂H₅, —S(=O)₂—NH₂, —S(=O)₂—NH—CH₃, —S(=O)₂—NH—C₂H₅, —S(=O)₂—NH-phenyl, —S(=O)₂—CH₃, —S(=O)₂—C₂H₅, —(CH₂)-benzo[b]furanyl, —O-phenyl, —S-phenyl, —S-benzyl, —O-benzyl, phenyl and benzyl, while the cyclic moiety of each of —O—C(=O)-phenyl, —(CH₂)—O—C(=O)-phenyl, —S(=O)₂—NH-phenyl, —O-phenyl, —S-phenyl, —S(=O)₂—NH-phenyl, —O-phenyl, —S-phenyl, —S-benzyl, —O-benzyl, phenyl, —(CH₂)-benzo[b]furanyl and benzyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, Isobutyl, tert-butyl, —O—CF₃, —S—CF₃, phenyl and —O-benzyl;

$R^{14}$ represents a moiety selected from the group consisting of methyl, ethyl, n-propyl, isopropyl, n-butyl, sec-butyl, Isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)(C₂H₅)—(CH₂)—(CH₂)—(CH₂)—(CH₃), vinyl, 1-propenyl, 2-propenyl, 1-butenyl, 2-butenyl, 3-butenyl, 1-propynyl, 2-propynyl, 1-butynyl, 2-butynyl and 3-butynyl, and each of moiety may be substituted by 1, 2, 3, 4 or 5 substituents each independently selected from the group consisting of F, Cl, Br, I, —CN, —NO₂, —OH, —SH, —NH₂, —N(CH₃)₂, —N(C₂H₅)₂ and —N(CH₃)(C₂H₅);

a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl, dithiolanyl, adamantyl and 7,7-dimethyl-bicyclo[2.2.1]heptyl, wherein each (hetero)cycloaliphatic moiety may be substituted by 1, 2, 3, 4 or 5 substituents each independently selected from the group consisting of oxo (=O), thioxo (=S), F, Cl, Br, I, —CN, —CF₃, —SF₅, —OH, —O—CH₃, —O—C₂H₅, —O—C(CH₃)₃, —NH₂, —NO₂, —O—CF₃, —S—CF₃, —SH, S—CH₃, —S—C₂H₅, —S—C(CH₃)₃, methyl, ethyl, n-propyl, isopropyl, n-butyl, sec-butyl, Isobutyl, tert-butyl, —C(=O)—H, —C(=O)—CH₃, —C(=O)—C₂H₅, —C(=O)—OH, —C(=O)—O—CH₃, —C(=O)—O—C₂H₅, —C(=O)—O—C(CH₃)₃, —(CH₂)—C(=O)—CH, —(CH₂)—C(=O)—O—CH₃, —(CH₂)—C(=O)—O—C₂H₅, —N(CH₃)₂, —N(C₂H₅)₂, —N(H)(CH₃), —N(H)(C₂H₅), —(CH₂)-benzo[b]furanyl, —O-phenyl, —O-benzyl, phenyl, benzyl, naphthyl and —(CH₂)-naphthyl, and the cyclic moiety of each of —O-phenyl, —O-benzyl, phenyl, —(CH₂)-benzo[b]furanyl, benzyl, naphthyl and —(CH₂)-naphthyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, methyl, ethyl, n-propyl, isopropyl, n-butyl, sec-butyl, Isobutyl, tert-butyl, —O—CF₃, —S—CF₃, phenyl and —O-benzyl;

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl, chromanyl and (1,2,3,4)-tetrahydroquinolynyl, and each of moiety may be substituted by 1, 2, 3, 4 or 5 substituents each independently selected from the group consisting of F, Cl, Br, I, —CN, —CF₃, —SF₅, —OH, —O—CH₃, —O—C₂H₅, —O—CH(CH₃)₂, —O—C(CH₃)₃, —O—CH₂—CH₂—CH₂—CH₃, —O—CH₂—CHisCH₂, —NH₂, —NO₂, —O—CF₃, —O—CHF₂, —O—CH₂F, —S—CF₃, —S—CHF₂, —S—CH₂F, —SH, —S—CH₃, —S—C₂H₅, —S—CH(CH₃)₂, —S—C(CH₃)₃, —S—CH₂—CH₂—CH₂—CH₃, methyl, ethyl, n-propyl, isopropyl, n-butyl, sec-butyl, Isobutyl, tert-butyl, (1,1)-dimethylpropyl, —C(=O)—OH, —C(=O)—O—CH₃, —C(=O)—O—C₂H₅, —C(=O)—O—C(CH₃)₃, —O—C(=O)—CH₃, —O—C(=O)—C₂H₅, —O—C(=O)-phenyl, —(CH₂)—O—C(=O)—CH₃, —(CH₂)—O—C(=O)—C₂H₅, —(CH₂)—O—C(=O)-phenyl, —N(CH₃)₂, —N(C₂H₅)₂, —N(H)(CH₃), —N(H)(C₂H₅), —NH—C(=O)—O—CH₃, —NH—C(=O)—O—C₂H₅, —NH—C(=O)—CH₃, —NH—C(=O)—C₂H₅, —C(=O)—H, —C(=O)—CH₃, —C(=O)—C₂H₅, —C(=O)—CF₃, —C(=O)—NH₂, —C(=O)—NH—CH₃, —C(=O)—NH—C₂H₅, —S(=O)₂—NH₂, —S(=O)₂—NH—CH₃, —S(=O)₂—NH—C₂H₅, —S(=O)₂—NH-phenyl, —S(=O)₂—CH₃, —S(=O)₂—C₂H₅, —(CH₂)-benzo[b]furanyl, —O-phenyl, —S-phenyl, —S-benzyl, —O-benzyl, phenyl and benzyl, and the cyclic moiety of each of —O—C(=O)-phenyl, —(CH₂)—O—C(=O)-phenyl, —S(=O)₂—NH-phenyl, —O-phenyl, —S-phenyl, —S-benzyl, —O-benzyl, phenyl, —(CH₂)-benzo[b]furanyl and benzyl may be substituted by 1, 2, 3, 4 or 5 substituents each independently selected from the group consisting of F, Cl, Br, —OH, —CF₃, —SF₅, —CN, —NO₂, —O—CH₃, —O—C₂H₅, —O—CH(CH₃)₂, —O—C(CH₃)₃, methyl, ethyl, n-propyl, isopropyl, n-butyl, sec-butyl, Isobutyl, tert-butyl, —O—CF₃, —S—CF₃, phenyl and —O-benzyl;

$R^{15}$ represents
hydrogen;
a moiety selected from the group consisting of methyl, ethyl, n-propyl, isopropyl, n-butyl, sec-butyl, Isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)(C₂H₅)—(CH₂)—(CH₂)—(CH₂)—(CH₃), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each moiety may be substituted by 1, 2, 3, 4 or 5 substituents each independently selected from the group consisting of F, Cl, Br, I, —CN, —NO₂, —OH, —SH, —NH₂, —N(CH₃)₂, —N(C₂H₅)₂ and —N(CH₃)(C₂H₅);

$R^{16}$ represents a moiety selected from the group consisting of methyl, ethyl, n-propyl, isopropyl, n-butyl, sec-butyl, Isobutyl, tert-butyl, n-pentyl, 2-pentyl, 3-pentyl, —(CH₂)—(C(CH₃)₃), n-hexyl, 3-hexyl, —(CH₂)—(CH₂)—(C(CH₃)₃), n-heptyl, 3-heptyl, 4-heptyl, n-octyl, —(CH₂)—(CH)(C₂H₅)—(CH₂)—(CH₂)—(CH₂)—(CH₃), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each moiety may be substituted by 1, 2, 3, 4 or 5 substituents each independently selected from the group consisting of F, Cl, Br, I, —CN, —NO$_2$, —OH, —SH, —NH$_2$, —N(CH$_3$)$_2$, —N(C$_2$H$_5$)$_2$ and —N(CH$_3$)(C$_2$H$_5$);

a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl and dithiolanyl, wherein each (hetero)cycloaliphatic moiety may be substituted by 1, 2, 3, 4 or 5 substituents each independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, S—CH$_3$, —S—C$_2$H$_5$, —S—C(CH$_3$)$_3$, methyl, ethyl, n-propyl, isopropyl, n-butyl, sec-butyl, Isobutyl, tert-butyl, —C(=O)—H, —C(=O)—CH$_3$, —C(=O)—C$_2$H$_5$, —C(=O)—OH, —C(=O)—O—CH$_3$, —C(=O)—O—C$_2$H$_5$, —C(=O)—O—C(CH$_3$)$_3$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —(CH$_2$)-benzo[b]furanyl, —O-phenyl, —O-benzyl, phenyl, benzyl, naphthyl and —(CH$_2$)-naphthyl, wherein the cyclic moiety of each of —O-phenyl, —O-benzyl, phenyl, —(CH$_2$)-benzo[b]furanyl, benzyl, naphthyl and —(CH$_2$)-naphthyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, methyl, ethyl, n-propyl, isopropyl, n-butyl, sec-butyl, Isobutyl, tert-butyl, —O—CF$_3$, —S—CF$_3$, phenyl and —O-benzyl;

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl, chromanyl and (1,2,3,4)-tetrahydroquinolynyl, wherein each moiety may be substituted by 1, 2, 3, 4 or 5 substituents each independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CHisCH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, Isobutyl, tert-butyl, (1,1)-dimethylpropyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—CF$_3$, —C(=O)—NH$_2$, —C(=O)—NH—CH$_3$, —C(=O)—NH—C$_2$H$_5$, —S(=O)$_2$—NH$_2$, —S(=O)$_2$—NH—CH$_3$, —S(=O)$_2$—NH—C$_2$H$_5$, —S(=O)$_2$—NH-phenyl, —S(=O)$_2$—CH$_3$, —S(=O)$_2$—C$_2$H$_5$, —(CH$_2$)-benzo[b]furanyl, —O-phenyl, —S-phenyl, —S-benzyl, —O-benzyl, phenyl and benzyl, wherein the cyclic moiety of each of —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl, and benzyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, Isobutyl, tert-butyl, —O—CF$_3$, —S—CF$_3$, phenyl and —O-benzyl;

$R^{17}$ represents a moiety selected from the group consisting of methyl, ethyl, n-propyl, isopropyl, n-butyl, sec-butyl, Isobutyl, tert-butyl, n-pentyl, 2-pentyl, 3-pentyl, —(CH$_2$)—(C(CH$_3$)$_3$), n-hexyl, 3-hexyl, —(CH$_2$)—(CH$_2$)—(C(CH$_3$)$_3$), n-heptyl, 3-heptyl, 4-heptyl, n-octyl, —(CH$_2$)—(CH)(C$_2$H$_5$)—(CH$_2$)—(CH$_2$)—(CH$_2$)—(CH$_3$), vinyl, 1-propenyl, 2-propenyl, 1-butenyl, 2-butenyl, 3-butenyl, 1-propynyl, 2-propynyl, 1-butynyl, 2-butynyl and 3-butynyl, wherein each moiety may be substituted by 1, 2, 3, 4 or 5 substituents each independently selected from the group consisting of F, Cl, Br, I, —CN, —NO$_2$, —OH, —SH, —NH$_2$, —N(CH$_3$)$_2$, —N(C$_2$H$_5$)$_2$ and —N(CH$_3$)(C$_2$H$_5$); and $R^{18}$ represents a (hetero)cycloaliphatic moiety selected from the group consisting of cyclopropyl, cyclobutyl, cyclopentyl, cyclohexyl, cycloheptyl, cyclopentenyl, cyclohexenyl, cycloheptenyl, imidazolidynyl, tetrahydrofuranyl, tetrahydrothiophenyl, pyrrolidynyl, piperidynyl, morpholynyl, piperazynyl, thiomorpholynyl, tetrahydropyranyl, azepanyl, diazepanyl and dithiolanyl, wherein the (hetero)cycloaliphatic moiety may be substituted by 1, 2, 3, 4 or 5 substituents each independently selected from the group consisting of oxo (=O), thioxo (=S), F, Cl, Br, I, —CN, —CF$_3$, —SF$_5$, —OH, —O—CH$_3$, —O—C$_2$H$_5$, —O—C(CH$_3$)$_3$, —NH$_2$, —NO$_2$, —O—CF$_3$, —S—CF$_3$, —SH, S—CH$_3$, —S—C$_2$H$_5$, —S—C(CH$_3$)$_3$, methyl, ethyl, n-propyl, isopropyl, n-butyl, sec-butyl, Isobutyl, tert-butyl, —C(=O)—H, —C(=O)—CH$_3$, —C(=O)—C$_2$H$_5$, —C(=O)—OH, —C(=O)—O—CH$_3$, —C(=O)—O—C$_2$H$_5$, —C(=O)—O—C(CH$_3$)$_3$, —(CH$_2$)—C(=O)—OH, —(CH$_2$)—C(=O)—O—CH$_3$, —(CH$_2$)—C(=O)—O—C$_2$H$_5$, —N(CH$_3$)$_2$, —N(C$_2$H$_5$)$_2$, —N(H)(CH$_3$), —N(H)(C$_2$H$_5$), —(CH$_2$)-benzo[b]furanyl, —O-phenyl, —O-benzyl, phenyl, benzyl, naphthyl and —(CH$_2$)-naphthyl, wherein the cyclic moiety of each of —O-phenyl, —O-benzyl, phenyl, —(CH$_2$)-benzo[b]furanyl, benzyl, naphthyl and —(CH$_2$)-naphthyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, methyl, ethyl, n-propyl, isopropyl, n-butyl, sec-butyl, Isobutyl, tert-butyl, —O—CF$_3$, —S—CF$_3$, phenyl and —O-benzyl;

a moiety selected from the group consisting of phenyl, naphthyl, thiophenyl, furanyl, pyrrolyl, pyrazolyl, pyrazynyl, triazolyl, pyridynyl, imidazolyl, indolyl, isoindolyl, benzo[b]furanyl, benzo[b]thiophenyl, thiazolyl, thiadiazolyl, oxazolyl, isoxazolyl, pyridazynyl, pyrazynyl, pyrimidynyl, indazolyl, quinazolynyl, quinolynyl, isoquinolynyl, phenazynyl, phenothiazynyl, oxadiazolyl, benzo[1,2,5]oxadiazolyl, chromanyl and (1,2,3,4)-tetrahydroquinolynyl, wherein each moiety may be substituted by 1, 2, 3, 4 or 5 substituents each independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CH$_2$—CHisCH$_2$, —NH$_2$, —NO$_2$, —O—CF$_3$, —O—CHF$_2$, —O—CH$_2$F, —S—CF$_3$, —S—CHF$_2$, —S—CH$_2$F, —SH, —S—CH$_3$, —S—C$_2$H$_5$, —S—CH(CH$_3$)$_2$, —S—C(CH$_3$)$_3$, —S—CH$_2$—CH$_2$—CH$_2$—CH$_3$, methyl, ethyl, n-propyl, isopropyl, n-butyl, sec-butyl, Isobutyl, tert-butyl, (1,1)-dimethylpropyl, —C(=O)—OH, —C(=O)—O—CH$_3$, —C(=O)—O—C$_2$H$_5$, —C(=O)—O—C(CH$_3$)$_3$, —O—C(=O)—CH$_3$, —O—C(=O)—C$_2$H$_5$, —O—C(=O)-phenyl, —(CH$_2$)—O—C(=O)—CH$_3$, —(CH$_2$)—O—C(=O)—C$_2$H$_5$, —(CH$_2$)—O—C(=O)-phenyl, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$, —NH—C(=O)—CH$_3$, —NH—C(=O)—C$_2$H$_5$, —C(=O)—H, —C(=O)—CH$_3$, —C(=O)—C$_2$H$_5$, —C(=O)—CF$_3$, —C(=O)—NH$_2$, —C(=O)—NH—CH$_3$, —C(=O)—NH—C$_2$H$_5$, —S(=O)$_2$—NH$_2$, —S(=O)$_2$-NH—CH$_3$, —S(=O)$_2$—NH—C$_2$H$_5$, —S(=O)$_2$—NH-phenyl, —S(=O)$_2$—CH$_3$, —S(=O)$_2$-C$_2$H$_5$, —(CH$_2$)-benzo[b]furanyl, —O-phenyl, —S-phenyl, —S-benzyl, —O-benzyl, phenyl and benzyl, wherein the cyclic moiety of each of —O—C(=O)-phenyl, —(CH$_2$)—O—C(=O)-phenyl, —S(=O)$_2$—NH-phenyl, —O-phenyl, —S-phenyl, —S-benzyl, —O-benzyl, phenyl, —(CH$_2$)-benzo[b]furanyl and benzyl may be substituted by 1, 2, 3, 4 or 5 substituents each independently selected from the group consisting of F, Cl, Br, —OH, —CF$_3$, —SF$_5$, —CN, —NO$_2$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, Isobutyl, tert-butyl, —O—CF$_3$, —S—CF$_3$, phenyl and —O-benzyl.

12. The compound of claim 10, wherein $R^1$ represents hydrogen;

methyl, ethyl, n-propyl, isopropyl, n-butyl, sec-butyl, isobutyl, tert-butyl, n-pentyl, 1-propenyl, 2-propenyl, 1-propynyl or 2-propynyl;

—(CH$_2$)—C(=O)—O—R$^7$;

—(CH$_2$)—R$^{12}$, —(CH$_2$)—(CH$_2$)—R$^{12}$, —(CH$_2$)—O—R$^{12}$, —(CH$_2$)—S—R$^{12}$, —(CH$_2$)—N(CH$_3$)—R$^{12}$, —(CH$_2$)—(CH$_2$)—(CH$_2$)—R$^{12}$ or —(CH$_2$)—(CH$_2$)—O—R$^{12}$;

$R^2$ represents hydrogen;

methyl, ethyl, n-propyl, isopropyl, n-butyl, sec-butyl, isobutyl, tert-butyl and n-pentyl;

—(CH$_2$)—R$^{13}$, —(CH$_2$)—(CH$_2$)—R$^{13}$, —(CH$_2$)—O—R$^{13}$, —(CH$_2$)—S—R$^{13}$, —(CH$_2$)—N(CH$_3$)—R$^{13}$, —(CH$_2$)—(CH$_2$)—S—R$^{13}$ or —(CH$_2$)—(CH$_2$)—O—R$^{13}$;

$R^4$ represents

—NR$^{10}$R$^{11}$;

methyl, ethyl, n-propyl, isopropyl, n-butyl, sec-butyl, isobutyl, tert-butyl, n-pentyl, 2-pentyl, 3-pentyl, —(CH$_2$)—(C(CH$_3$)$_3$) or n-hexyl;

a moiety selected from the group consisting of phenyl, naphthyl, thiophenyl, furanyl und (1,2,3,4)-tetrahydroquinolynyl, wherein each moiety may be substituted by 1, 2, 3, 4 or 5 substituents independently selected from the group consisting of F, Cl, Br, —CF$_3$, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —NO$_2$, —O—CF$_3$, —O—CHF$_2$, —O—CH$_2$F, —S—CF$_3$, —S—CHF$_2$, —S—CH$_2$F, methyl, ethyl, n-propyl, isopropyl, n-butyl, sec-butyl, isobutyl, tert-butyl, (1,1)-dimethyl-propyl, —C(=O)—O—CH$_3$, —C(=O)—O—C$_2$H$_5$, —C(=O)—CH$_3$, —C(=O)—C$_2$H$_5$, —C(=O)—CF$_3$, —S(=O)$_2$—CH$_3$, and —S(=O)$_2$—C$_2$H$_5$;

—(CH$_2$)—R$^{14}$, —(CH$_2$)—(CH$_2$)—R$^{14}$ or —(CH$_2$)—(CH$_2$)—(CH$_2$)—R$^{14}$;

$R^5$ represents methyl, ethyl, n-propyl, isopropyl, 1-propenyl or 2-propenyl;

phenyl which may be substituted by 1, 2, 3, 4 or 5 substituents independently selected from the group consisting of F, Cl, Br, —CN, —CF$_3$, —O—CH$_3$, —O—C$_2$H$_5$, —O—CH(CH$_3$)$_2$, —O—C(CH$_3$)$_3$, —O—CH$_2$—CH$_2$—CH$_2$—CH$_3$, —O—CF$_3$, —O—CHF$_2$, —O—CH$_2$F, —S—CF$_3$, —S—CHF$_2$, —S—CH$_2$F, —SH, methyl, ethyl, n-propyl, isopropyl, n-butyl, sec-butyl, isobutyl, tert-butyl, (1,1)-dimethylpropyl, —C(=O)—O—CH$_3$, —C(=O)—O—C$_2$H$_5$ or —C(=O)—CH$_3$, —C(=)—$_2$H$_5$;

—(CHR$^{15}$)—R$^{16}$, —(CHR$^{15}$)—(CH$_2$)—R$^{16}$, —(CHR$^{15}$)—(CH$_2$)—(CH$_2$)—R$^{16}$, —(CHR$^{15}$)—(CH$_2$)—O—R$^{16}$ or —(CHR$^{15}$)—(CH$_2$)—S—R$^{16}$;

—C(=O)—OR$^8$;

—(CHR$^{17}$)—C(=O)—OR$^9$ or —(CHR$^{17}$)—(CH$_2$)—C(=O)—OR$^9$;

$R^6$ represents cyclopentyl, cyclohexyl or cycloheptyl;

phenyl, which may be substituted by 1, 2, 3, 4 or 5 substituents independently selected from the group consisting of F, Cl, Br, I, —CN, —CF$_3$, —O—CH$_3$, —O—C$_2$H$_5$, —O—CH(CH$_3$)$_2$, —O—C(CH$_3$)$_3$, —O—CF$_3$, —O—CHF$_2$, —O—CH$_2$F, —C(=O)—O—CH$_3$, —C(=O)—O—C$_2$H$_5$, —C(=O)—CH$_3$ or —C(=O)—C$_2$H$_5$;

—(CH$_2$)—R$^{18}$, —(CH$_2$)—(CH$_2$)—R$^{18}$ or —(CH$_2$)—(CH$_2$)—(CH$_2$)—R$^{18}$;

$R^7$, $R^8$, $R^9$, $R^{10}$ and $R^{11}$ each independently represent methyl or ethyl;

$R^{12}$ represents a phenyl or naphthyl group, wherein each group may be substituted by 1, 2, 3, 4 or 5 substituents independently selected from the group consisting of F, Cl, Br, —CN, —CF$_3$, —NO$_2$, methyl, ethyl, n-propyl, isopropyl, n-butyl, sec-butyl, isobutyl, tert-butyl, —C(=O)—O—CH$_3$, —C(=O)—O—C$_2$H$_5$, —C(=O)—CH$_3$ or —C(=O)—C$_2$H$_5$;

$R^{13}$ represents methyl or ethyl;

phenyl, which may be substituted by 1, 2, 3, 4 or 5 substituents independently selected from the group consisting of F, Cl, Br or —CN;

$R^{14}$ represents a 7,7-dimethyl-2-oxo-bicyclo[2.2.1]heptyl or phenyl group;

$R^{15}$ represents hydrogen, methyl or ethyl;

$R^{16}$ represents methyl or ethyl;

a (hetero)cycloaliphatic moiety selected from the group consisting of cyclopentyl, cyclohexyl, cycloheptyl, and tetrahydrofuranyl;

phenyl, which may be substituted by 1, 2, 3, 4 or 5 substituents independently selected from the group consisting of F, Cl, Br, —CN, —CF$_3$, —O—CH$_3$, —O—C$_2$H$_5$ and —O—CH(CH$_3$)$_2$, R$^{17}$ represents methyl or ethyl;

and

R$^{18}$ represents a (hetero)cycloaliphatic moiety selected from the group consisting of cyclopentyl, cyclohexyl and cycloheptyl;

phenyl, which may be substituted by 1, 2, 3, 4 or 5 substituents independently selected from the group consisting of F, Cl and Br.

13. The compound of claim 1, wherein said compound is selected from the group consisting of:

[1] 3-Isopropyl-8-(4-nitrobenzolsulfonyl)-1,4,8-triazaspiro[4,5]decan-2-one,

[2] 8-(2-Chlorobenzolsulfonyl)-3-isobutyl-1,4,8-triazaspiro[4,5]decan-2-one,

[3] 3-Benzyl-8-[2-(2,2,2-trifluoroacetyl)-1,2,3,4-tetrahydroisoquinolin-7-sulfonyl]-1,4,8-triazaspiro[4,5]decan-2-one,

[4] 3-Benzyl-8-(4-methoxy-2,3,6-trimethylbenzolsulfonyl)-1,4,8-triazaspiro[4,5]decan-2-one,

[5] 2-[8-(4-Butoxy-benzolsulfonyl)-2-oxo-1,4,8-triazaspiro[4,5]dec-1-ylmethyl]-benzonitrile,

[6] 2-{8-[4-(1,1-Dimethylpropyl)benzolesulfonyl]-2-oxo-1,4,8-triazaspiro[4,5]dec-1-ylmethyl}-benzonitrile,

[7] 3-Benzyl-8-(2-fluorobenzolsulfonyl)-1,4,8-triazaspiro[4,5]decan-2-one,

[8] 8-(2-Chlorobenzolsulfonyl)-3-isopropyl-1,4,8-triazaspiro[4,5]decan-2-one,

[9] 1-Benzyl-2-oxo-1,4,8-triazaspiro[4,5]decan-8-sulfonic acid dimethylamide,

[10] 3-[8-(4-Acetylbenzolsulfonyl)-3-(2-methylsulfanylethyl)-2-oxo-1,4,8-triazaspiro[4,5]dec-1-ylmethyl]-benzonitrile,

[11] 1-(2-Fluorobenzyl)-3-isopropyl-8-(4-methoxy-2,3,6-trimethylbenzolsulfonyl)-1,4,8-triazaspiro[4,5]decan-2-one,

[12] 1-Butyl-8-(5-chlorothiophen-2-sulfonyl)-3-(2-methylsulfanylethyl)-1,4,8-triazaspiro[4,5]decan-2-one,

[13] 8-(4-Acetylbenzolsulfonyl)-1-butyl-3-(2-methylsulfanylethyl)-1,4,8-triazaspiro[4,5]decan-2-one,

[14] 1-Benzyl-3-isopropyl-8-(2,4,6-trimethylbenzolsulfonyl)-1,4,8-triazaspiro[4,5]decan-2-one,

[15] Methyl 2-(1-butyl-3-isopropyl-2-oxo-1,4,8-triazaspiro[4,5]decan-8-sulfonyl)benzoate,

[16] 1,3-Dibenzyl-8-(thiophen-2-sulfonyl)-1,4,8-triazaspiro[4,5]decan-2-one,

[17] 8-(3-Chloro-4-fluorobenzolsulfonyl)-3-isopropyl-1-(2-phenoxy-ethyl)-1,4,8-triazaspiro[4,5]decan-2-one,

[18] 1-Butyl-3-(2-methylsulfanylethyl)-8-(toluol-3-sulfonyl)-1,4,8-triazaspiro[4,5]decan-2-one,

[19] 1-Butyl-8-(2,4-difluorobenzolsulfonyl)-3-isopropyl-1,4,8-triazaspiro[4,5]decan-2-one,

[20] 1,3-Dibenzyl-8-(2,5-dichlorothiophen-3-sulfonyl)-1,4,8-triazaspiro[4,5]decan-2-one,

[21] 3-Isopropyl-1-(2-phenoxy-ethyl)-8-(toluol-4-sulfonyl)-1,4,8-triazaspiro[4,5]decan-2-one,

[22] 3-Benzyl-1-butyl-8-(2-trifluoromethylbenzolsulfonyl)-1,4,8-triazaspiro[4,5]decan-2-one,

[23] Methyl 2-[1-(4-fluorobenzyl)-3-(2-methylsulfanylethyl)-2-oxo-1,4,8-triazaspiro[4,5]decan-8-sulfonyl]-benzoate,

[24] 1,3-Dibenzyl-8-(2,3,5,6-tetramethylbenzolsulfonyl)-1,4,8-triazaspiro[4,5]decan-2-one,

[25] 1-(4-Fluorobenzyl)-3-(2-methylsulfanylethyl)-8-(2-trifluoromethylbenzolsulfonyl)-1,4,8-triazaspiro[4,5]decan-2-one,

[26] 8-(4-Chloro-2,5-dimethylbenzolsulfonyl)-1-(4-fluorobenzyl)-3-(2-methylsulfanylethyl)-1,4,8-triazaspiro[4,5]decan-2-one,

[27] 1-Benzyl-8-(4-chloro-2,5-dimethylbenzolsulfonyl)-3-isobutyl-1,4,8-triazaspiro[4,5]decan-2-one,

[28] 3-Benzyl-1-butyl-8-[4-(1,1-dimethylpropyl)benzolesulfonyl]-1,4,8-triazaspiro[4,5]decan-2-one,

[29] 1,3-Dibenzyl-8-(3,4-dimethoxy-benzolsulfonyl)-1,4,8-triazaspiro[4,5]decan-2-one,

[30] 1-Butyl-8-(3,4-dimethoxy-benzolsulfonyl)-3-(2-methylsulfanylethyl)-1,4,8-triazaspiro[4,5]decan-2-one,

[31] 1,3-Dibenzyl-8-(4-methoxy-2,3,6-trimethylbenzolsulfonyl)-1,4,8-triazaspiro[4,5]decan-2-one,

[32] 1-Benzyl-8-ethanesulfonyl-3-(2-methylsulfanylethyl)-1,4,8-triazaspiro[4,5]decan-2-one,

[33] 3-Benzyl-1-butyl-8-(4-ethylbenzolsulfonyl)-1,4,8-triazaspiro[4,5]decan-2-one,

[34] 3-(2-Methylsulfanylethyl)-1-prop-2-ynyl-8-(3-trifluoromethylbenzolsulfonyl)-1,4,8-triazaspiro[4,5]decan-2-one,

[35] 1,3-Dibenzyl-8-(4-ethylbenzolsulfonyl)-1,4,8-triazaspiro[4,5]decan-2-one,

[36] 3-Benzyl-1-butyl-8-(3-chlorobenzolsulfonyl)-1,4,8-triazaspiro[4,5]decan-2-one,

[37] 1,3-Dibenzyl-8-(2-fluorobenzolsulfonyl)-1,4,8-triazaspiro[4,5]decan-2-one,

[38] Methyl 2-[1-(2-cyanobenzyl)-3-(2-methylsulfanylethyl)-2-oxo-1,4,8-triazaspiro[4,5]decan-8-sulfonyl]-benzoate,

[39] 3-Benzyl-1-prop-2-ynyl-8-(2-trifluoromethylbenzolsulfonyl)-1,4,8-triazaspiro[4,5]decan-2-one,

[40] 3-Benzyl-8-(3-chlorobenzolsulfonyl)-1-methyl-1,4,8-triazaspiro[4,5]decan-2-one,

[41] 1-Benzyl-8-[4-(1,1-dimethylpropyl)benzolesulfonyl]-3-(2-methylsulfanylethyl)-1,4,8-triazaspiro[4,5]decan-2-one,

[42] 8-(2,4-Difluorobenzolsulfonyl)-1-(3,5-dimethylbenzyl)-3-(2-methylsulfanylethyl)-1,4,8-triazaspiro[4,5]decan-2-one,

[43] 1,3-Dibenzyl-8-(4-nitrobenzolsulfonyl)-1,4,8-triazaspiro[4,5]decan-2-one,

[44] 1-(4-Fluorobenzyl)-3-(2-methylsulfanylethyl)-8-(toluol-4-sulfonyl)-1,4,8-triazaspiro[4,5]decan-2-one,

[45] 1,3-Dibenzyl-8-(toluol-4-sulfonyl)-1,4,8-triazaspiro[4,5]decan-2-one,

[46] Ethyl[3-benzyl-8-(2-methyl-5-nitrobenzolsulfonyl)-2-oxo-1,4,8-triazaspiro[4,5]dec-1-yl]-acetate,

[47] Ethyl[3-benzyl-8-(2-methansulfonylbenzolsulfonyl)-2-oxo-1,4,8-triazaspiro[4,5]dec-1-yl]-acetate,

[48] 3 Ethyl-benzyl-2-oxo-8-(thiophen-2-sulfonyl)-1,4,8-triazaspiro[4,5]dec-1-yl]-acetate,

[49] Methyl 4-(8-ethanesulfonyl-2-oxo-1,4,8-triazaspiro[4,5]dec-1-ylmethyl)benzoate,

[50] Ethyl[3-benzyl-8-(4-methoxy-benzolsulfonyl)-2-oxo-1,4,8-triazaspiro[4,5]dec-1-yl]-acetate,

[51] Methyl 4-(2-Oxo-8-benzolmethansulfonyl-1,4,8-triazaspiro[4,5]dec-1-ylmethyl)benzoate,

[52] 3-[3-Isopropyl-8-(4-nitrobenzolsulfonyl)-2-oxo-1,4,8-triazaspiro[4,5]dec-1-ylmethyl]-benzonitrile,

[53] Methyl 4-[8-(butan-1-sulfonyl)-2-oxo-1,4,8-triazaspiro[4,5]dec-1-ylmethyl]-benzoate,

[54] 1-Allyl-8-(2-methansulfonylbenzolsulfonyl)-3-(2-methylsulfanylethyl)-1,4,8-triazaspiro[4,5]decan-2-one,

[55] 1-(2-Fluorobenzyl)-2-oxo-1,4,8-triazaspiro[4,5]decan-8-sulfonic acid dimethylamide,

[56] 8-(7,7-Dimethyl-2-oxobicyclo[2.2.1]hept-1-yl-methansulfonyl)-1-(2-fluorobenzyl)-1,4,8-triazaspiro[4,5]decan-2-one,
[57] Ethyl[3-(2-methylsulfanylethyl)-2-oxo-8-benzolmethansulfonyl-1,4,8-triazaspiro[4,5]dec-1-yl]-acetate,
[58] 1-Allyl-3-(2-methylsulfanylethyl)-8-benzolmethansulfonyl-1,4,8-triazaspiro[4,5]decan-2-one,
[59] 3-[2-Oxo-8-(2,4,6-trimethylbenzolsulfonyl)-1,4,8-triazaspiro[4,5]dec-1-ylmethyl]-benzonitril,
[60] Methyl 4-[2-oxo-8-(2,4,6-trimethylbenzolsulfonyl)-1,4,8-triazaspiro[4,5]dec-1-ylmethyl]-benzoate,
[61] Ethyl[3-benzyl-8-(5-chlorothiophen-2-sulfonyl)-2-oxo-1,4,8-triazaspiro[4,5]dec-1-yl]-acetate,
[62] Ethyl[3-benzyl-8-(butan-1-sulfonyl)-2-oxo-1,4,8-triazaspiro[4,5]dec-1-yl]-acetate,
[63] Ethyl[3-benzyl-2-oxo-8-(toluol-3-sulfonyl)-1,4,8-triazaspiro[4,5]dec-1-yl]-acetate,
[64] 1-(2-Fluorobenzyl)-8-(4-methoxy-benzolsulfonyl)-1,4,8-triazaspiro[4,5]decan-2-one,
[65] Ethyl[3-benzyl-2-oxo-8-(2-trifluoromethylbenzolsulfonyl)-1,4,8-triazaspiro[4,5]dec-1-yl]-acetate,
[66] Ethyl (8-benzolsulfonyl-3-benzyl-2-oxo-1,4,8-triazaspiro[4,5]dec-1-yl)acetate,
[67] Ethyl[3-benzyl-2-oxo-8-(4-propylbenzolsulfonyl)-1,4,8-triazaspiro[4,5]dec-1-yl]-acetate,
[68] Ethyl (3-benzyl-2-oxo-8-benzolmethansulfonyl-1,4,8-triazaspiro[4,5]dec-1-yl)acetate,
[69] Ethyl[3-benzyl-8-(3-chloro-4-fluorobenzolsulfonyl)-2-oxo-1,4,8-triazaspiro[4,5]dec-1-yl]-acetate,
[70] 1-Allyl-3-isopropyl-8-(2,4,6-trimethylbenzolsulfonyl)-1,4,8-triazaspiro[4,5]decan-2-one,
[71] 8-Benzolsulfonyl-3-benzyl-1-(2-fluorobenzyl)-1,4,8-triazaspiro[4,5]decan-2-one,
[72] Ethyl[3-benzyl-2-oxo-8-(2,4,6-trimethylbenzolsulfonyl)-1,4,8-triazaspiro[4,5]dec-1-yl]-acetate,
[73] Ethyl[3-benzyl-8-(4-butoxy-benzolsulfonyl)-2-oxo-1,4,8-triazaspiro[4,5]dec-1-yl]-acetate,
[74] Ethyl[3-benzyl-8-(2,5-dimethoxy-benzolsulfonyl)-2-oxo-1,4,8-triazaspiro[4,5]dec-1-yl]-acetate,
[75] 3-(2-Methylsulfanylethyl)-1-naphthalin-2-ylmethyl-2-oxo-1,4,8-triazaspiro[4,5]decan-8-sulfonic acid dimethylamide,
[76] 1-(3-Cyanobenzyl)-3-isopropyl-2-oxo-1,4,8-triazaspiro[4,5]decan-8-sulfonic acid dimethylamide,
[77] 3-{3-Isopropyl-2-oxo-8-[2-(2,2,2-trifluoroacetyl)-1,2,3,4-tetrahydroisoquinolin-7-sulfonyl]-1,4,8-triazaspiro[4,5]dec-1-ylmethyl}-benzonitril,
[78] 1-Allyl-3-(2-methylsulfanylethyl)-8-[2-(2,2,2-trifluoroacetyl)-1,2,3,4-tetrahydroisoquinolin-7-sulfonyl]-1,4,8-triazaspiro[4,5]decan-2-one,
[79] 1-Allyl-8-(4-methoxy-2,3,6-trimethylbenzolsulfonyl)-3-(2-methylsulfanylethyl)-1,4,8-triazaspiro[4,5]decan-2-one,
[80] Methyl 2-(3-benzyl-1-ethoxycarbonylmethyl-2-oxo-1,4,8-triazaspiro[4,5]decan-8-sulfonyl)benzoate,
[81] 3-Benzyl-1-(2-fluorobenzyl)-8-(2-trifluoromethylbenzolsulfonyl)-1,4,8-triazaspiro[4,5]decan-2-one,
[82] 8-(2-Chlorobenzolsulfonyl)-3-(2-methylsulfanylethyl)-1-(2-nitrobenzyl)-1,4,8-triazaspiro[4,5]decan-2-one,
[83] 1-Allyl-3-(2-methylsulfanylethyl)-8-(toluol-3-sulfonyl)-1,4,8-triazaspiro[4,5]decan-2-one,
[84] Ethyl[8-(2-chlorobenzolsulfonyl)-3-(2-methylsulfanylethyl)-2-oxo-1,4,8-triazaspiro[4,5]dec-1-yl]-acetate,
[85] 3-benzyl-1-(2-fluorobenzyl)-8-(toluol-4-sulfonyl)-1,4,8-triazaspiro[4,5]decan-2-one,
[86] Methyl 4-[8-(2,5-dichlorothiophen-3-sulfonyl)-2-oxo-1,4,8-triazaspiro[4,5]dec-1-ylmethyl]-benzoate,
[87] 3-[8-(4-Fluorobenzolsulfonyl)-3-isopropyl-2-oxo-1,4,8-triazaspiro[4,5]dec-1-ylmethyl]-benzonitril,
[88] 8-(2,5-Dimethoxy-benzolsulfonyl)-3-(2-methylsulfanylethyl)-1-(2-nitrobenzyl)-1,4,8-triazaspiro[4,5]decan-2-one,
[89] 8-(3-Chloro-4-fluorobenzolsulfonyl)-1-(2-fluorobenzyl)-1,4,8-triazaspiro[4,5]decan-2-one,
[90] 1-(2-Fluorobenzyl)-8-(toluol-3-sulfonyl)-1,4,8-triazaspiro[4,5]decan-2-one,
[91] 1-(2,6-Dichlorobenzyl)-8-(4,5-dichlorothiophen-2-sulfonyl)-3-isobutyl-1,4,8-triazaspiro[4,5]decan-2-one,
[92] 8-(5-Chlorothiophen-2-sulfonyl)-1-(2-fluorobenzyl)-1,4,8-triazaspiro[4,5]decan-2-one,
[93] 3-Benzyl-1-(2-fluorobenzyl)-8-(4-propylbenzolsulfonyl)-1,4,8-triazaspiro[4,5]decan-2-one,
[94] 3-[8-(Butan-1-sulfonyl)-3-isopropyl-2-oxo-1,4,8-triazaspiro[4,5]dec-1-ylmethyl]-benzonitril,
[95] 3-[8-(2-Methansulfonylbenzolsulfonyl)-2-oxo-1,4,8-triazaspiro[4,5]dec-1-ylmethyl]-benzonitril,
[96] 8-(2-Fluorobenzolsulfonyl)-1-(2-fluorobenzyl)-1,4,8-triazaspiro[4,5]decan-2-one,
[97] Methyl 2-[1-(3-cyanobenzyl)-3-isopropyl-2-oxo-1,4,8-triazaspiro[4,5]decan-8-sulfonyl]-benzoate,
[98] 3-Benzyl-1-(2-fluorobenzyl)-8-(5-fluoro-2-methyl-benzolsulfonyl)-1,4,8-triazaspiro[4,5]decan-2-one,
[99] 1-Allyl-8-(4-methoxy-benzolsulfonyl)-3-(2-methylsulfanylethyl)-1,4,8-triazaspiro[4,5]decan-2-one,
[100] 1-(3,5-Dimethylbenzyl)-3-isobutyl-8-(thiophen-2-sulfonyl)-1,4,8-triazaspiro[4,5]decan-2-one,
[101] 3-(2-Methylsulfanylethyl)-8-(4-nitrobenzolsulfonyl)-1-(2-nitrobenzyl)-1,4,8-triazaspiro[4,5]decan-2-one,
[102] 2-Isobutyl-3-oxo-1,4,8-triazaspiro[4,5]decan-8-thiocarboxylic acid o-tolylamide,
[103] 2-Benzyl-3-oxo-1,4,8-triazaspiro[4,5]decan-8-thiocarboxylic acid isopropylamide,
[104] 1-Butyl-3-isopropyl-2-oxo-1,4,8-triazaspiro[4,5]decan-8-thiocarboxylic acid (tetrahydrofuran-2-ylmethyl) amide,
[105] Ethyl 3-{[1-methyl-3-(2-methylsulfanylethyl)-2-oxo-1,4,8-triazaspiro[4,5]decan-8-carbothioyl]-amino}-butyrate,
[106] 1-Allyl-3-isopropyl-2-oxo-1,4,8-triazaspiro[4,5]decan-8-thiocarboxylic acid isopropylamide,
[107] 1-Butyl-3-isopropyl-2-oxo-1,4,8-triazaspiro[4,5]decan-8-thiocarboxylic acid isopropylamide,
[108] 3-Benzyl-1-(2-fluorobenzyl)-2-oxo-1,4,8-triazaspiro[4,5]decan-8-thiocarboxylic acid (2-methoxy-benzol)amide,
[109] Ethyl[8-Isopropylthiocarbamoyl-3-(2-methylsulfanylethyl)-2-oxo-1,4,8-triazaspiro[4,5]dec-1-yl]-4acetate,
[110] 1-Methyl-3-(2-methylsulfanylethyl)-2-oxo-1,4,8-triazaspiro[4,5]decan-8-thiocarboxylic acid m-tolylamide,
[111] 1-Methyl-3-(2-methylsulfanylethyl)-2-oxo-1,4,8-triazaspiro[4,5]decan-8-thiocarboxylic acid 4-methoxy-benzylamide,
[112] 2-Isobutyl-3-oxo-1,4,8-triazaspiro[4,5]decan-8-thiocarboxylic acid (4-fluorobenzol)amide,
[113] Ethyl[8-ethoxycarbonylaminocarbothioyl-3-(2-methylsulfanylethyl)-2-oxo-1,4,8-triazaspiro[4,5]dec-1-yl]-acetate,

[114] Ethyl 3-{[1-ethoxycarbonylmethyl-3-(2-methylsulfanylethyl)-2-oxo-1,4,8-triazaspiro[4,5]decan-8-carbothioyl]-amino}-butyrate,

[115] 1-Allyl-3-isopropyl-2-oxo-1,4,8-triazaspiro[4,5]decan-8-thiocarboxylic acid (2-methoxy-benzol)amide,

[116] 1-Butyl-3-isopropyl-2-oxo-1,4,8-triazaspiro[4,5]decan-8-thiocarboxylic acid benzolamide,

[117] 1-Butyl-3-isopropyl-2-oxo-1,4,8-triazaspiro[4,5]decan-8-thiocarboxylic acid (2,5-dichlorobenzol)amide,

[118] 3-Benzyl-1-methyl-2-oxo-1,4,8-triazaspiro[4,5]decan-8-thiocarboxylic acid (2,5-difluorobenzol)amide,

[119] 1-Methyl-3-(2-methylsulfanylethyl)-2-oxo-1,4,8-triazaspiro[4,5]decan-8-thiocarboxylic acid (2-bromobenzol)amide,

[120] 1-Butyl-3-(2-methylsulfanylethyl)-2-oxo-1,4,8-triazaspiro[4,5]decan-8-thiocarboxylic acid (2,5-dichlorobenzol)amide,

[121] 3-(2-Methylsulfanylethyl)-1-naphthalin-2-ylmethyl-2-oxo-1,4,8-triazaspiro[4,5]decan-8-thiocarboxylic acid (2-methoxy-ethyl)amide,

[122] 1-Butyl-3-isopropyl-2-oxo-1,4,8-triazaspiro[4,5]decan-8-thiocarboxylic acid (2-fluorobenzol)amide,

[123] 3-Isobutyl-2-oxo-1-prop-2-ynyl-1,4,8-triazaspiro[4,5]decan-8-thiocarboxylic acid allylamide,

[124] 1-Butyl-3-isopropyl-2-oxo-1,4,8-triazaspiro[4,5]decan-8-thiocarboxylic acid m-tolylamide,

[125] 1-Allyl-3-isopropyl-2-oxo-1,4,8-triazaspiro[4,5]decan-8-thiocarboxylic acid (4-fluorobenzol)amide,

[126] Methyl 4-(8-allylthiocarbamoyl-3-isopropyl-2-oxo-1,4,8-triazaspiro[4,5]dec-1-ylmethyl)benzoate,

[127] 1-Butyl-3-(2-methylsulfanylethyl)-2-oxo-1,4,8-triazaspiro[4,5]decan-8-thiocarboxylic acid (2-methoxy-benzol)amide,

[128] 1-Allyl-3-isopropyl-2-oxo-1,4,8-triazaspiro[4,5]decan-8-thiocarboxylic acid (2,5-difluorobenzol)amide,

[129] 1-(2-Cyanobenzyl)-3-(2-methylsulfanylethyl)-2-oxo-1,4,8-triazaspiro[4,5]decan-8-thiocarboxylic acid allylamide,

[130] 1-(3-Cyanobenzyl)-3-(2-methylsulfanylethyl)-2-oxo-1,4,8-triazaspiro[4,5]decan-8-thiocarboxylic acid allylamide,

[131] Ethyl 3-[(3-benzyl-1-methyl-2-oxo-1,4,8-triazaspiro[4,5]decan-8-carbothioyl) amino]-butyrate,

[132] 1-Butyl-3-(2-methylsulfanylethyl)-2-oxo-1,4,8-triazaspiro[4,5]decan-8-thiocarboxylic acid cyclohexylmethylamide,

[133] 1-Methyl-3-(2-methylsulfanylethyl)-2-oxo-1,4,8-triazaspiro[4,5]decan-8-thiocarboxylic acid (4-chlorobenzol)amide,

[134] 1-Methyl-3-(2-methylsulfanylethyl)-2-oxo-1,4,8-triazaspiro[4,5]decan-8-thiocarboxylic acid 4-fluorobenzylamide,

[135] Methyl 4-[8-(2,6-dichlorobenzolthiocarbamoyl)-3-isopropyl-2-oxo-1,4,8-triazaspiro[4,5]dec-1-ylmethyl]-benzoate,

[136] 1-Benzyl-3-isopropyl-2-oxo-1,4,8-triazaspiro[4,5]decan-8-thiocarboxylic acid (2,5-dichlorobenzol)amide,

[137] Methyl 4-{3-isopropyl-2-oxo-8-[(tetrahydrofuran-2-ylmethyl)thiocarbamoyl]-1,4,8-triazaspiro[4,5]dec-1-ylmethyl}-benzoate,

[138] 1-Methyl-3-(2-methylsulfanylethyl)-2-oxo-1,4,8-triazaspiro[4,5]decan-8-thiocarboxylic acid (2,5-difluorobenzol)amide,

[139] 1-Benzyl-3-(2-methylsulfanylethyl)-2-oxo-1,4,8-triazaspiro[4,5]decan-8-thiocarboxylic acid (4-isopropylbenzol)amide,

[140] 1-Benzyl-3-(2-methylsulfanylethyl)-2-oxo-1,4,8-triazaspiro[4,5]decan-8-thiocarboxylic acid (2,5-difluorobenzol)amide,

[141] 1-(2-Cyanobenzyl)-3-isobutyl-2-oxo-1,4,8-triazaspiro[4,5]decan-8-thiocarboxylic acid (3-acetylbenzol)amide,

[142] 1-Butyl-3-isopropyl-2-oxo-1,4,8-triazaspiro[4,5]decan-8-thiocarboxylic acid (3-chlorobenzol)amide,

[143] Methyl 2-[(1-butyl-3-isopropyl-2-oxo-1,4,8-triazaspiro[4,5]decan-8-carbothioyl)amino]-benzoate,

[144] Ethyl (3-benzyl-8-ethoxycarbonylaminocarbothioyl-2-oxo-1,4,8-triazaspiro[4,5]dec-1-yl) acetate,

[145] Methyl 2-[(3-benzyl-1-ethoxycarbonylmethyl-2-oxo-1,4,8-triazaspiro[4,5]decan-8-carbothioyl)amino]-benzoate,

[146] Ethyl[1-(2-cyanobenzyl)-3-(2-methylsulfanylethyl)-2-oxo-1,4,8-triazaspiro[4,5]decan-8-carbothioyl]-carbamate,

[147] 1-(2-Cyanobenzyl)-3-(2-methylsulfanylethyl)-2-oxo-1,4,8-triazaspiro[4,5]decan-8-thiocarboxylic acid (2-chloro-5-trifluoromethylbenzol)amide,

[148] 3-(2-Methylsulfanylethyl)-1-naphthalin-2-ylmethyl-2-oxo-1,4,8-triazaspiro[4,5]decan-8-thiocarboxylic acid (1-benzol-ethyl)amide,

[149] 1-Allyl-3-isopropyl-2-oxo-1,4,8-triazaspiro[4,5]decan-8-thiocarboxylic acid pentafluorobenzolamide,

[150] 1-Butyl-3-isopropyl-2-oxo-1,4,8-triazaspiro[4,5]decan-8-thiocarboxylic acid 4-chlorobenzylamide,

[151] 3-(2-Methylsulfanylethyl)-1-naphthalin-2-ylmethyl-2-oxo-1,4,8-triazaspiro[4,5]decan-8-thiocarboxylic acid o-tolylamide,

[152] 1-Butyl-3-isopropyl-2-oxo-1,4,8-triazaspiro[4,5]decan-8-thiocarboxylic acid pentafluorobenzolamide,

[153] Methyl 2-{[1-(2-cyanobenzyl)-3-(2-methylsulfanylethyl)-2-oxo-1,4,8-triazaspiro[4,5]decan-8-carbothioyl]-amino}-benzoate,

[154] 1-Benzyl-3-isopropyl-2-oxo-1,4,8-triazaspiro[4,5]decan-8-thiocarboxylic acid pentafluorobenzolamide,

[155] 1-Benzyl-3-isopropyl-2-oxo-1,4,8-triazaspiro[4,5]decan-8-thiocarboxylic acid (2-methoxy-benzol)amide,

[156] 1-Benzyl-3-isopropyl-2-oxo-1,4,8-triazaspiro[4,5]decan-8-thiocarboxylic acid benzolamide,

[157] 1-Benzyl-3-isopropyl-2-oxo-1,4,8-triazaspiro[4,5]decan-8-thiocarboxylic acid (2,5-difluorobenzol)amide,

[158] 1-Butyl-3-(2-methylsulfanylethyl)-2-oxo-1,4,8-triazaspiro[4,5]decan-8-thiocarboxylic acid (4-ethoxy-benzol)amide,

[159] Ethyl[3-benzyl-8-(cyclohexylmethylthiocarbamoyl)-2-oxo-1,4,8-triazaspiro[4,5]dec-1-yl]-acetate,

[160] 1-Butyl-3-(2-methylsulfanylethyl)-2-oxo-1,4,8-triazaspiro[4,5]decan-8-thiocarboxylic acid benzylamide,

[161] 1-(2-Cyanobenzyl)-3-(2-methylsulfanylethyl)-2-oxo-1,4,8-triazaspiro[4,5]decan-8-thiocarboxylic acid m-tolylamide,

[162] 1-Allyl-3-isopropyl-2-oxo-1,4,8-triazaspiro[4,5]decan-8-thiocarboxylic acid 4-fluorobenzylamide,

[163] 3-Isobutyl-2-oxo-1-prop -2-ynyl-1,4,8-triazaspiro[4,5]decan-8-thiocarboxylic acid (3-acetylbenzol)amide,

[164] Methyl 4-(3-isopropyl-2-oxo-8-pentafluorobenzolthiocarbamoyl-1,4,8-triazaspiro[4,5]dec-1-ylmethyl)benzoate,

[165] 3-(2-Methylsulfanylethyl)-1-naphthalin-2-ylmethyl-2-oxo-1,4,8-triazaspiro[4,5]decan-8-thiocarboxylic acid (3-acetylbenzol) amide,
[166] 3-Benzyl-1-(2-fluorobenzyl)-2-oxo-1,4,8-triazaspiro[4,5]decan-8-thiocarboxylic acid m-tolylamide,
[167] Methyl 4-(8-ethoxycarbonylaminocarbothioyl-3-isopropyl-2-oxo-1,4,8-triazaspiro[4,5]dec-1-ylmethyl) benzoate,
[168] 1-(4-Fluorobenzyl)-3-(2-methylsulfanylethyl)-2-oxo-1,4,8-triazaspiro[4,5]decan-8-thiocarboxylic acid (tetrahydrofuran-2-ylmethyl)amide,
[169] 1-(2-Cyanobenzyl)-3-isobutyl-2-oxo-1,4,8-triazaspiro[4,5]decan-8-thiocarboxylic acid (3,5-bis-trifluoromethylbenzol)amide,
[170] 1-(2-Cyanobenzyl)-3-isobutyl-2-oxo-1,4,8-triazaspiro[4,5]decan-8-thiocarboxylic acid benzylamide,
[171] 3-Benzyl-1-(2-fluorobenzyl)-2-oxo-1,4,8-triazaspiro[4,5]decan-8-thiocarboxylic acid cyclohexylmethylamide,
[172] 1-(3-Cyanobenzyl)-3-(2-methylsulfanylethyl)-2-oxo-1,4,8-triazaspiro[4,5]decan-8-thiocarboxylic acid (4-chlorobenzol)amide,
[173] 1-Butyl-3-(2-methylsulfanylethyl)-2-oxo-1,4,8-triazaspiro[4,5]decan-8-thiocarboxylic acid pentafluorobenzolamide,
[174] Ethyl[3-benzyl-1-(2-fluorobenzyl)-2-oxo-1,4,8-triazaspiro[4,5]decan-8-carbothioyl]-carbamate,
[175] 3-Benzyl-1-methyl-2-oxo-1,4,8-triazaspiro[4,5]decan-8-thiocarboxylic acid 4-chlorobenzylamide,
[176] 1-(4-Fluorobenzyl)-3-(2-methylsulfanylethyl)-2-oxo-1,4,8-triazaspiro[4,5]decan-8-thiocarboxylic acid isopropylamide,
[177] 1-Benzyl-3-isopropyl-2-oxo-1,4,8-triazaspiro[4,5]decan-8-thiocarboxylic acid (3,5-dichlorobenzol) amide,
[178] Ethyl[1-(3-cyanobenzyl)-3-(2-methylsulfanylethyl)-2-oxo-1,4,8-triazaspiro[4,5]decan-8-carbothioyl]-carbamate,
[179] 1-Benzyl-3-isopropyl-2-oxo-1,4,8-triazaspiro[4,5] decan-8-thiocarboxylic acid 4-fluorobenzylamide,
[180] 1-Allyl-3-isopropyl-2-oxo-1,4,8-triazaspiro[4,5]decan-8-thiocarboxylic acid (3,5-dichlorobenzol)amide,
[181] 1-(3-Cyanobenzyl)-3-(2-methylsulfanylethyl)-2-oxo-1,4,8-triazaspiro[4,5]decan-8-thiocarboxylic acid (1-benzol-ethyl)amide,
[182] 1-(4-Fluorobenzyl)-3-(2-methylsulfanylethyl)-2-oxo-1,4,8-triazaspiro[4,5]decan-8-thiocarboxylic acid 4-fluorobenzylamide,
[183] 1-(2-Cyanobenzyl)-3-(2-methylsulfanylethyl)-2-oxo-1,4,8-triazaspiro[4,5]decan-8-thiocarboxylic acid (2-methoxy-benzol)amide,
[184] 1-(3-Cyanobenzyl)-3-(2-methylsulfanylethyl)-2-oxo-1,4,8-triazaspiro[4,5]decan-8-thiocarboxylic acid (2-methoxy-benzol)amide,
[185] 1-(3-Cyanobenzyl)-3-(2-methylsulfanylethyl)-2-oxo-1,4,8-triazaspiro[4,5]decan-8-thiocarboxylic acid 4-chlorobenzylamide,
[186] 1-(4-Fluorobenzyl)-3-(2-methylsulfanylethyl)-2-oxo-1,4,8-triazaspiro[4,5]decan-8-thiocarboxylic acid o-tolylamide,
[187] 3-Benzyl-1-(2-fluorobenzyl)-2-oxo-1,4,8-triazaspiro[4,5]decan-8-thiocarboxylic acid (2,6-dichlorobenzol)amide,
[188] 3-Benzyl-1-(2-fluorobenzyl)-2-oxo-1,4,8-triazaspiro[4,5]decan-8-thiocarboxylic acid (2-chloro-5-trifluoromethylbenzol)amide,
[189] 1-Butyl-3-(2-methylsulfanylethyl)-2-oxo-1,4,8-triazaspiro[4,5]decan-8-thiocarboxylic acid (4-fluorobenzol)amide,
[190] 3-Isobutyl-2-oxo-1-prop-2-ynyl-1,4,8-triazaspiro[4,5]decan-8-thiocarboxylic acid (2,6-dichlorobenzol) amide,
[191] Methyl 4-[8-(4-chlorobenzylthiocarbamoyl)-3-isopropyl-2-oxo-1,4,8-triazaspiro[4,5]dec-1-ylmethyl]-benzoate,
[192] 1-(4-Fluorobenzyl)-3-(2-methylsulfanylethyl)-2-oxo-1,4,8-triazaspiro[4,5]decan-8-thiocarboxylic acid (3-cyanobenzol)amide,
[193] 1-(2-Cyanobenzyl)-3-(2-methylsulfanylethyl)-2-oxo-1,4,8-triazaspiro[4,5]decan-8-thiocarboxylic acid 4-chlorobenzylamide,
[194] 1-Methyl-3-(2-methylsulfanylethyl)-2-oxo-1,4,8-triazaspiro[4,5]decan-8-thiocarboxylic acid (3-trifluoromethylbenzol)amide,
[195] 3-Isobutyl-2-oxo-1-prop-2-ynyl-1,4,8-triazaspiro[4,5]decan-8-thiocarboxylic acid (3,5-dichlorobenzol) amide,
[196] 1-(4-Fluorobenzyl)-3-(2-methylsulfanylethyl)-2-oxo-1,4,8-triazaspiro[4,5]decan-8-thiocarboxylic acid (1-benzol-ethyl)amide,
[197] 3-Benzyl-1-(2-fluorobenzyl)-2-oxo-1,4,8-triazaspiro[4,5]decan-8-thiocarboxylic acid 4-chlorobenzylamide,
[198] 2-Isopropyl-3-oxo-1,4,8-triazaspiro[4,5]decan-8-thiocarboxylic acid (4-fluorobenzol)amide,
[199] 1-Benzyl-3-isopropyl-2-oxo-1,4,8-triazaspiro[4,5] decan-8-thiocarboxylic acid benzylamide,
[200] 1-(4-Fluorobenzyl)-3-(2-methylsulfanylethyl)-2-oxo-1,4,8-triazaspiro[4,5]decan-8-thiocarboxylic acid (4-ethoxy-benzol)amide,
[201] 3-Benzyl-1-(2-fluorobenzyl)-2-oxo-1,4,8-triazaspiro[4,5]decan-8-thiocarboxylic acid (3-acetylbenzol) amide,
[202] 3-Benzyl-1-methyl-2-oxo-1,4,8-triazaspiro[4,5]decan-8-carboxylic acid cyclohexylamide,
[203] Ethyl[3-(2-methylsulfanylethyl)-2-oxo-8-benzolcarbamoyl-1,4,8-triazaspiro[4,5]dec-1-yl]-acetate,
[204] 1-Allyl-3-isopropyl-2-oxo-1,4,8-triazaspiro[4,5]decan-8-carboxylic acid (2,5-dimethoxy-benzol)amide,
[205] 1-Methyl-3-(2-methylsulfanylethyl)-2-oxo-1,4,8-triazaspiro[4,5]decan-8-carboxylic acid (3-fluorobenzol)amide,
[206] Methyl 4-(8-cyclohexylcarbamoyl-3-isopropyl-2-oxo-1,4,8-triazaspiro[4,5]dec-1-ylmethyl)benzoate,
[207] 1-Butyl-3-(2-methylsulfanylethyl)-2-oxo-1,4,8-triazaspiro[4,5]decan-8-carboxylic acid benzolamide,
[208] 1-Benzyl-3-(2-methylsulfanylethyl)-2-oxo-1,4,8-triazaspiro[4,5]decan-8-carboxylic acid (3-cyanobenzol)amide,
[209] 1-Allyl-3-isopropyl-2-oxo-1,4,8-triazaspiro[4,5]decan-8-carboxylic acid (2,5-difluorobenzol)amide,
[210] 1-Butyl-3-(2-methylsulfanylethyl)-2-oxo-1,4,8-triazaspiro[4,5]decan-8-carboxylic acid (3,4,5-trimethoxy-benzol)amide,
[211] 1-Benzyl-3-(2-methylsulfanylethyl)-2-oxo-1,4,8-triazaspiro[4,5]decan-8-carboxylic acid (4-chloro-3-trifluoromethylbenzol)amide,
[212] 1-Methyl-3-(2-methylsulfanylethyl)-2-oxo-1,4,8-triazaspiro[4,5]decan-8-carboxylic acid (5-chloro-2-methoxy)amide,
[213] 1-Benzyl-3-(2-methylsulfanylethyl)-2-oxo-1,4,8-triazaspiro[4,5]decan-8-carboxylic acid (4-ethoxy-benzol)amide,

[214] 1-Benzyl-3-(2-methylsulfanylethyl)-2-oxo-1,4,8-triazaspiro[4,5]decan-8-carboxylic acid (3-acetylbenzol)amide,
[215] Ethyl 3-[(1-butyl-3-isopropyl-2-oxo-1,4,8-triazaspiro[4,5]decan-8-carbonyl)amino]-benzoate,
[216] 1-Butyl-3-isopropyl-2-oxo-1,4,8-triazaspiro[4,5]decan-8-carboxylic acid (2,5-dimethoxy-benzol)amide,
[217] 1-(2-Cyanobenzyl)-3-isobutyl-2-oxo-1,4,8-triazaspiro[4,5]decan-8-carboxylic acid 3,4-dichlorobenzylamide,
[218] 1-(2-Cyanobenzyl)-3-isobutyl-2-oxo-1,4,8-triazaspiro[4,5]decan-8-carboxylic acid (2,5-difluorobenzol)amide,
[219] 1-Butyl-3-(2-methylsulfanylethyl)-2-oxo-1,4,8-triazaspiro[4,5]decan-8-carboxylic acid 3,4-dichlorobenzylamide,
[220] 1-Allyl-3-isopropyl-2-oxo-1,4,8-triazaspiro[4,5]decan-8-carboxylic acid (4-trifluoromethoxy-benzol)amide,
[221] 1-Butyl-3-(2-methylsulfanylethyl)-2-oxo-1,4,8-triazaspiro[4,5]decan-8-carboxylic acid (4-ethoxy-benzol)amide,
[222] 1-Methyl-3-(2-methylsulfanylethyl)-2-oxo-1,4,8-triazaspiro[4,5]decan-8-carboxylic acid (4-trifluoromethoxy-benzol)amide,
[223] Methyl 4-[3-isopropyl-8-(3-methoxy-benzolcarbamoyl)-2-oxo-1,4,8-triazaspiro[4,5]dec-1-ylmethyl]-benzoate,
[224] 1-(2-Cyanobenzyl)-3-(2-methylsulfanylethyl)-2-oxo-1,4,8-triazaspiro[4,5]decan-8-carboxylic acid benzolamide,
[225] Ethyl[3-benzyl-8-(3,4-dichlorobenzylcarbamoyl)-2-oxo-1,4,8-triazaspiro[4,5]dec-1-yl]-acetate,
[226] 1-(2-Cyanobenzyl)-3-(2-methylsulfanylethyl)-2-oxo-1,4,8-triazaspiro[4,5]decan-8-carboxylic acid (3-fluorobenzol)amide,
[227] 1-Butyl-3-(2-methylsulfanylethyl)-2-oxo-1,4,8-triazaspiro[4,5]decan-8-carboxylic acid (4-chloro-3-trifluoromethylbenzol) amide,
[228] 1-(4-Fluorobenzyl)-3-(2-methylsulfanylethyl)-2-oxo-1,4,8-triazaspiro[4,5]decan-8-carboxylic acid 3,4-dichlorobenzylamide,
[229] 1-(2-Cyanobenzyl)-3-(2-methylsulfanylethyl)-2-oxo-1,4,8-triazaspiro[4,5]decan-8-carboxylic acid 3,4-dichlorobenzylamide,
[230] 3-Benzyl-1-(2-fluorobenzyl)-2-oxo-1,4,8-triazaspiro[4,5]decan-8-carboxylic acid (2,5-difluorobenzol)amide,
[231] 3-(2-Methylsulfanylethyl)-1-naphthalin-2-ylmethyl-2-oxo-1,4,8-triazaspiro[4,5]decan-8-carboxylic acid (4-ethoxy-benzol)amide,
[232] Methyl 4-[8-(3,4-dichlorobenzylcarbamoyl)-3-isopropyl-2-oxo-1,4,8-triazaspiro[4,5]dec-1-ylmethyl]-benzoate,
[233] 3-Benzyl-1-(2-fluorobenzyl)-2-oxo-1,4,8-triazaspiro[4,5]decan-8-carboxylic acid 3,4-dichlorobenzylamide,
[234] 1-(2-Cyanobenzyl)-3-(2-methylsulfanylethyl)-2-oxo-1,4,8-triazaspiro[4,5]decan-8-carboxylic acid (3-acetylbenzol)amide,
[235] Ethyl 4-{[3-benzyl-1-(2-fluorobenzyl)-2-oxo-1,4,8-triazaspiro[4,5]decan-8-carbonyl]-amino}-benzoate,
[236] 1-(3-Cyanobenzyl)-3-(2-methylsulfanylethyl)-2-oxo-1,4,8-triazaspiro[4,5]decan-8-carboxylic acid (3-methoxy-benzol)amide,
[237] 1-(4-Fluorobenzyl)-3-(2-methylsulfanylethyl)-2-oxo-1,4,8-triazaspiro[4,5]decan-8-carboxylic acid (4-trifluoromethoxy-benzol)amide,
[238] 3-Benzyl-1-(2-fluorobenzyl)-2-oxo-1,4,8-triazaspiro[4,5]decan-8-carboxylic acid cyclohexylamide,
[239] 1-(4-Fluorobenzyl)-3-(2-methylsulfanylethyl)-2-oxo-1,4,8-triazaspiro[4,5]decan-8-carboxylic acid phenethylamide,
[240] 3-(2-Methylsulfanylethyl)-1-naphthalin-2-ylmethyl-2-oxo-1,4,8-triazaspiro[4,5]decan-8-carboxylic acid (3-fluorobenzol)amide,
[241] Methyl 4-[8-(4-chloro-3-trifluoromethylbenzolcarbamoyl)-3-isopropyl-2-oxo-1,4,8-triazaspiro[4,5]dec-1-ylmethyl]-benzoate,
[242] 1-(3-Cyanobenzyl)-3-(2-methylsulfanylethyl)-2-oxo-1,4,8-triazaspiro[4,5]decan-8-carboxylic acid (2,5-dimethoxy-benzol)amide,
[243] 1-(4-Fluorobenzyl)-3-(2-methylsulfanylethyl)-2-oxo-1,4,8-triazaspiro[4,5]decan-8-carboxylic acid (4-ethoxy-benzol)amide,
[244] 1-(4-Fluorobenzyl)-3-(2-methylsulfanylethyl)-2-oxo-1,4,8-triazaspiro[4,5]decan-8-carboxylic acid (3-cyanobenzol)amide, and
[245] Ethyl[3-b-8-(3-fluorobenzolcarbamoyl)-2-oxo-1,4,8-triazaspiro[4,5]dec-1-yl]-acetate,
[246] 1,3-Dibenzyl-8-methansulfonyl-1,4,8-triazaspiro[4,5]decan-2-one,
[247] 8-Benzolsulfonyl-1,3-dibenzyl-1,4,8-triazaspiro[4,5]decan-2-one,
[248] 1,3-Dibenzyl-8-(4-chlorobenzolsulfonyl)-1,4,8-triazaspiro[4,5]decan-2-one,
[249] 1,3-Dibenzyl-8-(4-methoxy-benzolsulfonyl)-1,4,8-triazaspiro[4,5]decan-2-one,
[250] 1,3-Dibenzyl-2-oxo-1,4,8-triazaspiro[4,5]decan-8-carboxylic acid phenylamide,
[251] 1,3-Dibenzyl-2-oxo-1,4,8-triazaspiro[4,5]decan-8-carboxylic acid (4-methoxy-phenyl)amide,
[252] 1,3-Dibenzyl-2-oxo-1,4,8-triazaspiro[4,5]decan-8-thiocarboxylic acid phenylamide, and
[253] 1,3-Dibenzyl-2-oxo-1,4,8-triazaspiro[4,5]decan-8-thiocarboxylic acid (2,4-difluorophenyl)amide.

14. A process for producing a 1,4,8-triazaspiro[4,5]decan-2-one compound corresponding to formula 1,

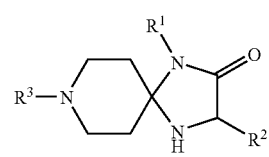

wherein
R¹ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group which may comprise at least one heteroatom as a link; or a —C(=O)OR⁷ group which may be bonded via a linear or branched alkylene group;

R² represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl group may be bonded via a linear or branched alkylene group which may comprise at least one heteroatom as a link;

R³ represents a —S(=O)₂—R⁴ group; a —C(=S)NH—R⁵ group; or a —C(=O)NH—R⁶ group;

R⁴ represents a —NR¹⁰R¹¹ group; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group, which may comprise at least one heteroatom as a ring member and which may be bonded via a linear or branched unsubstituted or at least monosubstituted alkylene group which may comprise at least one heteroatom as a link and which may be bridged by a linear or branched unsubstituted or at least monosubstituted alkylene group;

R⁵ represents a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group which may comprise at least one heteroatom as a link; an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link; a —C(=O)OR⁸ group or a —C(=O)OR⁹ group, which may, in either case, be bonded via a linear or branched alkylene group;

R⁶ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group which may comprise at least one heteroatom as a link; or for an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link;

R⁷, R⁸, R⁹, R¹⁰, and R¹¹, each independently represent a linear or branched alkyl group, a linear or branched alkenyl group, or a linear or branched alkynyl group, comprising the steps of:

converting a protected piperidin-4-one compound corresponding to formula II,

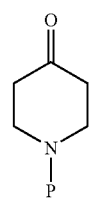

II in which P stands for a protective group, by reacting said compound corresponding to formula II with at least one amino-acid amide compound corresponding to formula III,

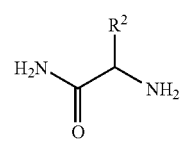

III to form least one compound corresponding to formula IV,

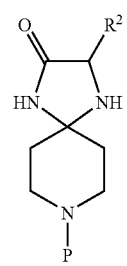

IV and optionally reacting said compound corresponding to formula IV with at least one compound corresponding to formula

R¹—X¹, wherein X¹ represents a suitable leaving group, which may be a halogen, to form at least one compound of corresponding to formula V,

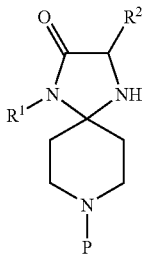

and, optionally, splitting-off the protective group P, to yield at least one compound corresponding to formula VI,

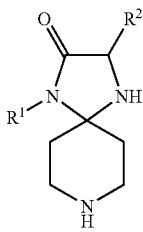

and converting at least one compound corresponding to formula IV, V or VI, by reacting said at least one compound with a sulfonyl compound corresponding to formula $R^4$—$SO_2$—$X^2$, or by reacting said at least one compound with an isothiocyanate compound corresponding to formula $R^5$—NCS or by reacting said at least one compound with an isocyanate compound corresponding to formula $R^6$—NCO wherein $X^2$ stands for a suitable leaving group, which may be a halogen radical, to form at least one compound corresponding to formula I.

15. A pharmaceutical formulation comprising at least one substituted 1,4,8-triazaspiro[4,5]decan-2-one compound corresponding to claim 1 and a pharmaceutically acceptable carrier or adjuvant.

16. A method of preparing a pharmaceutical formulation, said method comprising:
combining at least one 1,4,8-triazaspiro[4,5]decan-2-one compound according to claim 1 with a pharmaceutically acceptable carrier or adjuvant.

17. A method of treating a disease or condition selected from the group consisting of depression, pain disorders, and combined conditions of depression and pain, comprising the step of administering to a patient in need thereof a pharmaceutically effective amount of a compound corresponding to formula I:

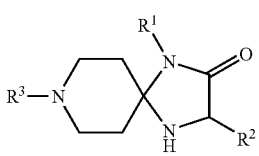

wherein
$R^1$ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group which may comprise at least one heteroatom as a link; or a —C(═O)$OR^7$ group which may be bonded via a linear or branched alkylene group;

$R^2$ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl group may be bonded via a linear or branched alkylene group which may comprise at least one heteroatom as a link;

$R^3$ represents a —S(═O)$_2$—$R^4$ group; a —C(═S)NH—$R^5$ group; or a —C(═O)NH—$R^6$ group;

$R^4$ represents a —$NR^{10}R^{11}$ group; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group, which may comprise at least one heteroatom as a ring member and which may be bonded via a linear or branched unsubstituted or at least monosubstituted alkylene group which may comprise at least one heteroatom as a link and which may be bridged by a linear or branched unsubstituted or at least monosubstituted alkylene group;

$R^5$ represents a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group which may comprise at least one heteroatom as a link; an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link; a —C(=O)OR⁸ group or a —C(=O)OR⁹ group, which may, in either case, be bonded via a linear or branched alkylene group;

R⁶ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group which may comprise at least one heteroatom as a link; or for an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link;

$R^7$, $R^8$, $R^9$, $R^{10}$, and $R^{11}$, each independently represent a linear or branched alkyl group, a linear or branched alkenyl group, or a linear or branched alkynyl group.

18. A method of treating pain in a mammal, said method comprising administering to said mammal an effective pain treating amount of a compound corresponding to formula I:

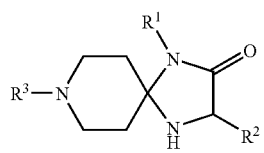

wherein $R^1$ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group which may comprise at least one heteroatom as a link; or a —C(=O)OR⁷ group which may be bonded via a linear or branched alkylene group;

$R^2$ represents hydrogen; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which aryl and heteroaryl group may be bonded via a linear or branched alkylene group which may comprise at least one heteroatom as a link;

$R^3$ represents a —S(=O)₂—R⁴ group; a —C(=S)NH—R⁵ group; or a —C(=O)NH—R⁶ group;

$R^4$ represents a —NR¹⁰R¹¹ group; a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group which may comprise at least one heteroatom as a link and may be condensed with an unsubstituted or at least monosubstituted monocyclic ring system; an unsubstituted or at least monosubstituted cycloaliphatic group, which may comprise at least one heteroatom as a ring member and which may be bonded via a linear or branched unsubstituted or at least monosubstituted alkylene group which may comprise at least one heteroatom as a link and which may be bridged by a linear or branched unsubstituted or at least monosubstituted alkylene group;

$R^5$ represents a linear or branched unsubstituted or at least monosubstituted alkyl group which may comprise at least one heteroatom as a link; a linear or branched unsubstituted or at least monosubstituted alkenyl group which may comprise at least one heteroatom as a link; a linear or branched unsubstituted or at least monosubstituted alkynyl group which may comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group which may comprise at least one heteroatom as a link; an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link; a —C(=O)OR⁸ group or a —C(=O)OR⁹ group, which may, in either case, be bonded via a linear or branched alkylene group;

$R^6$ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group which may comprise at least one heteroatom as a link; or for an unsubstituted or at least monosubstituted cycloaliphatic group, which may comprise at least one heteroatom as a ring member or which may be bonded via a linear or branched unsubstituted or at least monosubstituted alkylene group which may comprise at least one heteroatom as a link;

$R^7$, $R^8$, $R^9$, $R^{10}$, and $R^{11}$, each independently represent a linear or branched alkyl group, a linear or branched alkenyl group, or a linear or branched alkynyl group.

19. The method of claim 18, wherein said pain is acute pain, chronic pain, and/or neuropathic pain.

* * * * *